US006335312B1

(12) United States Patent
Coffindaffer et al.

(10) Patent No.: US 6,335,312 B1
(45) Date of Patent: Jan. 1, 2002

(54) PERSONAL CLEANSING COMPOSITIONS COMPRISING MID-CHAIN BRANCHED SURFACTANTS

(75) Inventors: Timothy Woodrow Coffindaffer, Loveland; Phillip Kyle Vinson, Fairfield; Thomas Anthony Cripe, Loveland; Anthony Charles Lanzalaco, Fairfield, all of OH (US); Robert Emerson Stidham, Lawrenceburg, IN (US); Daniel Stedman Connor, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/542,684

(22) Filed: Apr. 4, 2000

Related U.S. Application Data

(63) Continuation of application No. PCT/IB98/01585, filed on Oct. 12, 1998.
(60) Provisional application No. 60/061,916, filed on Oct. 14, 1997.

(51) Int. Cl.$^7$ .................................................. A61K 7/00
(52) U.S. Cl. ....................... 510/159; 510/119; 510/127; 510/130; 510/1
(58) Field of Search ............................. 510/119, 127, 510/130, 159, 426

(56) References Cited

U.S. PATENT DOCUMENTS

| | | | |
|---|---|---|---|
| 2,695,327 A | 11/1954 | Ziegler et al. | 260/683.15 |
| 2,934,568 A | 4/1960 | Baker et al. | 260/615 |
| 3,480,556 A | 11/1969 | DeWitt et al. | 252/152 |
| 3,647,906 A | 3/1972 | Farley | 260/683 |
| 3,775,349 A | 11/1973 | Turvell et al. | 252/547 |
| 3,887,624 A | 6/1975 | Gibson et al. | 260/615 B |
| 3,922,332 A | 11/1975 | Schenk | 423/268 |
| 4,075,129 A | 2/1978 | Murata et al. | 252/527 |
| 4,102,823 A | 7/1978 | Matheson | 252/533 |
| 4,111,855 A | 9/1978 | Barrat et al. | 252/545 |
| 4,732,707 A | 3/1988 | Naik et al. | 252/548 |
| 4,870,038 A | 9/1989 | Page et al. | 502/62 |
| 5,026,933 A | 6/1991 | Blain et al. | 585/7 |
| 5,030,774 A | 7/1991 | Oswald et al. | 568/882 |
| 5,245,072 A | 9/1993 | Giacobbe et al. | 560/99 |
| 5,284,989 A | 2/1994 | Apelian et al. | 585/533 |
| 5,446,213 A | 8/1995 | Sato et al. | 568/883 |
| 5,562,866 A | 10/1996 | Hu et al. | 510/432 |
| 5,780,694 A | 7/1998 | Singleton | 568/909 |
| 6,008,181 A | 12/1999 | Cripe et al. | 510/426 |
| 6,015,781 A | 1/2000 | Vinson et al. | 510/302 |
| 6,020,303 A | 2/2000 | Cripe et al. | 510/503 |
| 6,046,152 A | 4/2000 | Vinson et al. | 510/428 |
| 6,060,443 A | 5/2000 | Cripe et al. | 510/426 |

FOREIGN PATENT DOCUMENTS

| | | | |
|---|---|---|---|
| CA | 1086178 | 9/1980 | 134/3.11 |
| DE | 2243307 | 9/1972 | |
| EP | 0342917 | 11/1989 | |
| EP | 0357496 | 3/1990 | |
| EP | 0401642 | 12/1990 | |
| EP | 0439316 | 7/1991 | |
| EP | 0684300 | 11/1995 | |
| EP | 0728475 | 8/1996 | |
| EP | 0839898 | 5/1998 | |
| EP | 0859045 | 8/1998 | |
| FR | 1151630 | 2/1958 | |
| FR | 2176794 | 11/1973 | |
| FR | 2267369 | 7/1975 | |
| FR | 2424316 | 11/1979 | |
| FR | 2486821 | 7/1981 | |
| GB | 719445 | 12/1954 | |
| GB | 1399966 | 7/1975 | |
| GB | 2303144 | 2/1997 | |
| JP | 46-2666 | 1/1971 | C08F/26/141 |
| JP | 102099 | of 1973 | |
| JP | 49-2962 | 1/1974 | C11D/1/14 |
| JP | 7-62387 | 3/1995 | C11D/1/72 |
| WO | WO 85/02175 | 5/1959 | |
| WO | WO 94/11488 | 5/1994 | |
| WO | WO 95/00117 | 1/1995 | |
| WO | WO 96/04358 | 2/1996 | |
| WO | WO 96/18711 | 6/1996 | |
| WO | WO 97/01521 | 1/1997 | |
| WO | WO 97/29084 | 8/1997 | C07C/309/17 |
| WO | WO 97/38956 | 10/1997 | |
| WO | WO 97/38957 | 10/1997 | |
| WO | WO 97/38972 | 10/1997 | |
| WO | WO 97/39087 | 10/1997 | |
| WO | WO 97/39088 | 10/1997 | |
| WO | WO 97/39089 | 10/1997 | |
| WO | WO 97/39090 | 10/1997 | |
| WO | WO 97/39091 | 10/1997 | |
| WO | WO 98/11813 | 3/1998 | A47L/13/16 |
| WO | WO 98/23566 | 6/1998 | |
| WO | WO 98/23712 | 6/1998 | |
| WO | WO 98/35553 | 8/1998 | |

OTHER PUBLICATIONS

Findlay, J. W., et al. "Novel Sulfated Hydrocarbons from the Sea Cucumber *Cucumario Frondosa*", *Journal of Natural Products*, vol. 54, No. 1 (Jan.–Feb. 1991), pp. 302–304.
U.S. application No. 09/542,795, Vinson et al., filed Apr. 4, 2000.
U.S. application No. 09/543,087, Vinson et al., filed Apr. 4, 2000.
U.S. application No. 09/426,594, Cripe et al., filed Oct. 26, 1999.
U.S. application No. 09/170,424, Cripe et al., filed Oct. 13, 1998.
U.S. application No. 09/170,423, Connor et al., filed Oct. 13, 1999.

(List continued on next page.)

*Primary Examiner*—Necholus Ogden
(74) *Attorney, Agent, or Firm*—Ian S. Robinson; C. Brant Cook; Kim William Zerby

(57) ABSTRACT

This invention relates to personal cleansing products which include mid-chain branched surfactants.

28 Claims, No Drawings

OTHER PUBLICATIONS

U.S. application No. 09/434,181, Vinson et al., filed Nov. 4, 1999.

U.S. application No. 09/433,853, Vinson et al., filed Nov. 5, 1999.

U.S. application No. 09/170,694, Connor et al., filed Oct. 13, 1998.

U.S. application No. 09/170,711, Connor et al., filed Oct. 13, 1998.

R. G. Laughlin, "The Aqueous Phase Behavior of Surfactants", *Academic Presss*, N.Y. (1980), p. 347.

Finger, et al., "Detergent Alcohols—the effect of alcohol structure and molecular weight on surfactant properties", *J. Amer. Oil Chemists' Society*, vol. 44, (1967), p. 525.

Technical Bulletin, Shell Chemical Company, SC:364–80, No month available.

K. R. Wormuth, et al., "Phase Behavior of Branched Surfactants in Oil and Water", *Langmuir*, vol. 7, (1991), pp. 2048–2053.

R. Varadaraj, et al., "Fundamental Interfacial Properties of Alkyl–Branched Sulfate and Ethoxy Sulfate Surfactants Derived form Guerbet Alcohols. 1. Surface and Instantaneous Interfacial Tensions", *J. Phys. Chem.*, vol. 95 (1991), pp. 1671–1676.

R. Varadaraj, et al., "Relationship between Fundamental Interfacial Properties and Foaming in Linear and Branched Sulfate, Ethoxysulfate, and Ethoxylate Surfactants", *Journal of Colloid and Interface Science*, vol. 140, No. 1 (Nov. 1990), pp. 31–34.

R. Varadaraj, et al., "Micropolarity and Water Penetration in Micellar Aggregates of Linear and Branched Hydrocarbon Surfactants", *Langmuir*, vol. 6 (1990), pp. 1376–1378.

R. Varadaraj, et al., "Relationship between Dynamic Contact Angie and Dynamic Surface Tension Properties for Linear and Branched Ethoxylate, Ethoxysulfate, and Sulfate Surfactants", *Journal of Colloid and Interface Science*, vol. 147, No. 2 (Dec. 1991), pp. 403–406.

R. D. Swisher, "Surfactant Biodegradation", *Surfactant Science Series*, $2^{nd}$ Ed., Marcel Dekker, Inc., vol. 18, pp. 20–29 and 34–36, No month available.

CEH Marketing Research Report "Detergent Alcohols" by R.F. Modler, et al., *Chemical Economics Handbook*, (1993), pp. 609.5000–609.5002.

"Alcohols, Higher Aliphatic", *Kirk Othmer's Encyclopedia of Chemical Technology*, $4^{th}$ Ed., Wiley, N.Y., (1991), vol. 1, pp. 865–913.

"Liquid Fuels", *Kirk Othmer's Encyclopedia of Chemical Technology*, Wiley, N.Y., (1989), vol. 11, pp. 447–489.

"Oxo Process", *Kirk Othmer's Encyclopedia of Chemical Technology*, Wiley, N.Y., (1989), vol. 16, pp. 637–653.

"Sasol Detergent Alcohols", R&D Technical Bulletin, Sasol Alpha Olefins, (Oct. 1, 1996), pp. 1–12.

PERSONAL CLEANSING COMPOSITIONS COMPRISING MID-CHAIN BRANCHED SURFACTANTS

CROSS REFERENCE

This is a continuation under 35 U.S.C. §120 of PCT International Application Serial No. PCT/IB98/01585, filed Oct. 12, 1998; which claims priority to Provisional Application Serial No. 60/061,916, filed Oct. 14, 1997.

FIELD OF THE INVENTION

This invention relates to personal cleansing products which include mid-chain branched surfactants.

BACKGROUND OF THE INVENTION

The developer and formulator of surfactants for personal cleansing detergents must consider a wide variety of possibilities with limited (sometimes inconsistent) information, and then strive to provide overall improvements in one or more of a whole array of criteria, including performance in the presence of free calcium, in complex mixtures of surfactants and polymers, formulation changes including silicone conditioners, enzyme, various changes in consumer habits and practices, and the need for biodegradability. Furthermore, personal cleansing detergents should also employ materials that enhance product phase stability at low temperatures. Lack of phase stability can lead to unacceptable Theological and aesthetic properties as well as to performance issues. Such low temperatures can be encountered in warehouses, in the consumer's garage, in the consumer's automobile, during street vending, on a cold bathroom window sill, and the like.

Further, personal cleansing compositions should employ materials that enhance the dissolution, or rate of product mixing, with water. Further, personal cleansing detergents should employ materials that enhance the tolerance of the system to hardness, especially to avoid the precipitation of the calcium salts of anionic surfactants. Precipitation of the calcium salts of anionic surfactants is known to cause suppression of suds, irritation to the skin, and can lead to an undesirable hair feel. The lack of tolerance to low temperature and hardness prevents widespread use of personal cleansing products in which sodium alkyl sulfate is the only anionic surfactant.

The development of improved surfactants for use in personal cleansing compositions is clearly a complex challenge.

It is an aspect of the present invention to provide mixtures of the mid-chain branched primary alkyl surfactants which are formulatable with other surfactants to provide personal cleansing compositions having one or more advantages, including greater product stability at low temperatures, increased resistance to water hardness, greater efficacy in surfactant systems, improved removal of greasy or particulate body soils, lower deposition levels on the hair and skin with subsequent improvement in feel and mildness, and the like.

BACKGROUND ART

U.S. Pat. No. 3,480,556, EP 439,316, EP 684,300, EP 439,316, U.S. Pat. No. 3,480,556, R. G. Laughlin in "The Aqueous Phase Behavior of Surfactants", Academic Press, N.Y. (1994), Finger et al., "Detergent alcohols—the effect of alcohol structure and molecular weight on surfactant properties", J Amer. Oil Chemists' Society, Vol. 44, Technical Bulletin, Shell Chemical Co., SC: 364–80, EP 342,917 A, U.S. Pat. No. 4,102,823, GB 1,399,966, G.B. Patent 1,299,966, EP 401,462 A, K. R. Wormuth and S. Zushma, Langmuir, Vol. 7, (1991), pp 2048–2053, R. Varadaraj et al., J. Phys. Chem., Vol. 95, (1991), pp 1671–1676, Varadtraj et al., J. Colloid and terface Sci., Vol. 140, (1990), pp 31–34, Varadaraj7 et al., Langmuir, Vol. 6 (1990), pp 1376–1378, U.S. Pat. No. 5,284,989, U.S. Pat. No. 5,026,933, U.S. Pat. No. 4,870,038, Surfactant Science Series, Marcel Dekker, N.Y., CEH Marketing Research Report "Detergent Alcohols" by R. F. Modler et al., Chemical Economics Handbook, 1993, 609.5000–609.5002; Kirk Qtllmer's Encyclopedia of Chemical Technology, 4th Edition, Wiley, New York, 1991, "Alcohols, Higher Aliphatic" in Vol. 1, pp 865–913 and references therein.

SUMMARY OF THE INVENTION

The present invention provides a personal cleansing compositions comprising a mid-chain branched surfactants and a conventional personal cleansing adjutant.

Specifically, the present invention comprises a personal cleansing composition comprising:

i) from about 0.001% to about 49.9% by weight of a conventional personal cleansing additive;

ii) from a bout 0.1% to about 49.999% by weight of a surfactant system comprising a branched surfactant mixture, said branched surfactant mixture comprising mid-chain branched and linear surfactant compounds, said linear compounds less than about 25% by weight of the branched surfactant., mixture;

wherein the mid-chain branched surfactant compounds are of the formula:

$A^b$–B 

wherein:

$A^b$ is a hydrophobic moiety having from about 10 to about 18 total carbons divided between a longest chain and at least one short chain, the longest chain being in the range of from about 9 to about 17 carbon atoms, there being one or more $C_1$–$C_3$ alkyl moieties branching from the longest chain, provided that at least one of the branching alkyl moieties is attached directly to a carbon of the longest linear carbon chain at a position within the range of position 3 carbon, counting from carbon #1 which is attached to the —B moiety, to position ω—2 carbon, wherein co is the terminal carbon;

B is a hydrophilic moiety selected from the group consisting of $OSO_3M$, $(EO/PO)mOH$, $EO/PO)mOSO_3M$ and mixtures thereof, wherein EO/PO are alkoxy moieties selected from the group consisting of ethoxy, propoxy, and mixtures thereof, wherein m is at least about 1 to about 30 and M is hydrogen or a salt forming cation;

provided that the average total number of carbon atoms in the $A^b$ moiety in the branched surfactant mixture is within the range of about 12 to 14.5; and (iii) from about 50% to about 99.899%, by weight of an aqueous liquid carrier.

In a second embodiment the present invention also includes an antidandruff shampoo comprising a branched surfactant system, hereinbefore defined; from about 0.1% to about 5% by weight of an antidandruff agent selected from the group consisting of type (a), type (b), both of are defined hereinafter, and mixtures thereof; and from about 50% to about 99.89%, by weight of an aqueous liquid carrier;

In a third embodiment the present invention also includes a personal cleansing composition comprising a branched surfactant system, hereinbefore defined; from about 0.005% to about 20% by weight of a conditioning agent selected from the group consisting of nonvolatile hydrocarbon conditioning agents. nonvolatile silicone conditioning agents and mixtures thereof; from about 50% to about 99.89%, by weight of an aqueous liquid carrier; and from about 0.1% to about 10%, by weight of a suspending agent.

In a fourth embodiment the present invention also includes a personal cleansing composition comprising a branched surfactant system, hereinbefore defined; from about 0.1% to about 10% by weight of a water insoluble hair styling polymer; from about 50% to about 99.849%, by weight of an aqueous liquid carrier; and from about 0.1% to about 10%, by weight of a volatile water insoluble solvent.

In a fifth embodiment the present invention also includes a personal cleansing composition comprising a branched surfactant system, hereinbefore defined; from about 0.01% to about 5% by weight of a deposition polymer; and from about 50% to about 99.89%, by weight of an aqueous liquid carrier;

In a sixth embodiment the present invention also includes a personal cleansing composition comprising a branched surfactant system, hereinbefore defined; from about 0.1% to about 10% by weight of a dispersed phase polymer; and from about 50% to about 99.89%, by weight of an aqueous liquid carrier;

In a seventh embodiment the present invention also includes a method of treating hair by administering a safe and effective amount of a personal cleansing composition as hereinbefore defined.

In an eight embodiment the present invention also includes a method of treating skin by administering a safe and effective amount of a personal cleansing composition as hereinbefore defined.

In a ninth embodiment the present invention also includes a method of cleaning hair and skin by administering a safe and effective amount of a personal cleansing composition as hereinbefore defined.

These and other aspects, features and advantages will be apparent from the following description and the appended claims.

All percentages, ratios and proportions herein are on a weight basis unless otherwise indicated. All documents cited herein are hereby incorporated herein by reference.

DETAILED DESCRIPTION OF THE INVENTION

The personal cleansing compositions of this invention comprise a surfactant-containing, preferably surfactant-structured liquid phase which comprises a branched surfactant mixture comprising linear and mid-chain branched surfactants. The essential and optional components of the surfactant mixture and other optional materials of the detergent compositions herein, as well as composition form, preparation and use, are described in greater detail as follows: (All concentrations and ratios are on a weight basis unless otherwise specified.)

Specifically, the present invention comprises a personal cleansing composition The personal cleansing composition comprises:

i) from about 0.001% to about 49.9%, by weight of a conventional personal cleansing additive;
ii) from about 0.1% to about 49.999% by weight of a surfactant system comprising a branched surfactant mixture, said branched surfactant mixture comprising mid-chain branched and linear surfactant compounds, said linear compounds comprising 25% or less by weight of the branched surfactant mixture;
wherein the mid-chain branched surfactant compounds are of the formmula:

$A^b$-B wherein:

$A^b$ is a hydrophobic moiety having from about 10 to about 18 total carbons divided between a longest chain and at least one short chain, the longest chain being in the range of from about 9 to about 17 carbon atoms, there being one or more $C_1$–$C_3$ alkyl moieties branching from the longest chain, provided that at least one of the branching alkyl moieties is attached directly to a carbon of the longest linear carbon chain at a position within the range of position 3 carbon, counting from carbon #1 which is attached to the—B moiety, to position ω—2 carbon, wherein ω is the terminal carbon;

B is a hydrophilic moiety selected from the group consisting of $OSO_3M$, (EO/PO)mOH, (EO/PO)m$OSO_3M$ and mixtures thereof, wherein EO/PO are alkoxy moieties selected from the group consisting of ethoxy, propoxy, and mixtures thereof, wherein m is at least about 1 to about 30 and M is hydrogen or a salt forming cation;

provided that the average total number of carbon atoms in the $A^b$ moiety in the branched surfactant mixture is within the range of about 12 to 14.5; and (iii) from about 50% to about 99.899%, by weight of an aqueous liquid carrier.

The detergent compositions defined herein comprises from about 0.01% to about 49.999% by weight of the surfactant system. The surfactant system will be present in the personal cleansing composition at preferably at least about 0.5%, more preferably, at least about 1%, even more preferably at least about 2%, even more preferably still at least about 5%, even more preferably still at least about 8%, most preferably at least about 10%, by weight. Furthermore, the surfactant system will be; present in the personal cleansing composition at preferably at less than about 45%, more preferably less than about 45%, even more preferably less than about 40%, even more preferably less than about 35%, even more preferably less than about 30%, by weight.

$A^b$ moiety has from about 10 to about 18, preferably from about 11 to about 17, most preferably from about 11 to about 15 carbon atoms. The average total number of carbon atoms in the $A^b$ moiety in the branched surfactant mixture defined above should be within the range of from about 12 to 14.5, preferably from about 12 to about 14 and most preferably from about 12 to about 13.5. The "total" number of carbon atoms as used herein is intended to mean the number of carbon atoms in the longest chain, i.e. the backbone of the molecule, plus the number of carbon atoms in all of the short chains, i.e. the branches.

The detergent compositions defined herein also comprise from about 0.001% to about 49.9% by weight of the composition of a conventional personal cleansing additive. The conventional personal cleansing additive will be present in the personal cleansing composition at preferably at least about 0.5%, more preferably, at least about 1%, even more preferably at least about 2%, even more preferably still at least about 5%, even more preferably still at least about 8%, most preferably at least about 10%, by weight. Furthermore, the conventional personal cleansing additive will be present in the personal cleansing composition at preferably at less than about 45%, more preferably less than about 40%, even more preferably less than about 35%, even more preferably less than about 30%, even more preferably less than about 20%, most preferably less than about 15%, by weight. This conventional personal cleansing additive is selected from the group comprising conditioning agents, conventional personal care polymers, antidandruff agents co-surfactants and mixtures thereof, all of which are hereinafter defined.

The aqueous liquid carrier is present in the personal cleansing composition from about 50% to about 99.899%, preferably about 60% to about 95%, more preferably about 70% to about 85% by weight.

The linear surfactant compounds present in the branched surfactant mixture comprise 25% or less preferably about 20% or less, more preferably about 15% or less even more preferably about 10% or less and even more preferably still about 5% or less by weight of the surfactant mixture.

The personal cleansing composition of the present invention is in the form of a liquid or a liquid gel. It can contain for example, suspended ingredients, more than one phase etc. Effectively the personal cleansing compositions of the present invention can be in the form of any type of liquid or liquid gel and contain any additive conventionally added to personal cleansing compositions, such as shampoos, body wash gels, bath gels etc.

The branched surfactants for use in the personal cleansing compositions of the present invention can preferably comprise compounds of the above formula wherein the $A^b$ moiety is a branched alkyl moiety having the formula:

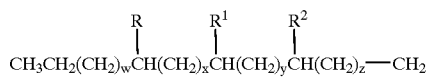

wherein the total number of carbon atoms in the branched alkyl moiety of this formula, including the R, $R^1$, and $R^2$ branching, is from 8 to 18; R, $R^1$, and $R^2$ are each independently selected from hydrogen and $C_1$–$C_3$ alkyl, preferably methyl, provided R, $R^1$, and $R^2$ are not all hydrogen and, when z is 0, at least R or $R^1$ is not lhydrogen; w is an integer from 0 to 10; x is an integer from 0 to 10; y is an integer from 0 to 10; z is an integer from 0 to 10 land w+x+y+z is from 2 to 10.

Moreover, an especially preferred branched surfactant for use in the personal cleansing compositions of the present invention comprises an $A^b$ moiety which is characterized as having one of the two formulas below and mixtures thereof:

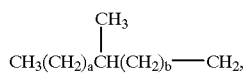
(I)

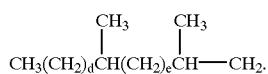
(II)

or mixtures thereof; wherein a, b, d, and e are integers, a+b is from 6 to 13, d+e is from 4 to 11 and wherein further when a+b=6, a is an integer from 2 to 5 and b is an integer from 1 to 4;

when a+b=7, a is an integer from 2 to 6 and b is an integer from 1 to 5;

when a+b=8, a is an integer from 2 to 7 and b is an integer from 1 to 6;

when a+b=9, a is an integer from 2 to 8 and b is an integer from 1 to 7;

when a+b=10, a is an integer from 2 to 9 and b is an integer from 1 to 8;

when a+b=11, a is an integer from 2 to 10 and b is an integer from 1 to 9;

when a+b=12, a is an integer from 2 to 11 and b is an integer from 1 to 10;

when a+b=13, a is an integer from 2 to 12 and b is an integer from 1 to 11;

when d+e=4, d is an integer from 2 to 3 and e is an integer from 1 to 2;

when d+e=5, d is an integer from 2 to 4 and e is an integer from 1 to 3;

when d+e=6, d is an integer from 2 to 5 and e is an integer from 1 to 4;

when d+e=7, d is an integer from 2 to 6 and e is an integer from 1 to 5;

when d+e=8, d is an integer from 2 to 7 and e is an integer from 1 to 6;

when d+e=9, d is an integer from 2 to 8 and e is an integer from 1 to 7;

when d+e=10, d is an integer from 2 to 9 and e is an integer from 1 to 8.

when d+e=11, d is an integer from 2 to 10 and e is an integer from 1 to 9.

(1) Midhain Branched Primary Alkyl Sulfate Surfactants

The mid-chain branched surfactant system for use in the personal cleansing compositions of the present invention may comprise one or more mid-chain branched primary alkyl sulfate surfactants having the formula:

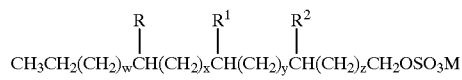

More specifically, the branched surfactant mixtures of the present invention comprise molecules having a linear primary alkyl sulfate chain backbone (i.e., the longest linear carbon chain which includes the sulfated carbon atom). These alkyl chain backbones comprise from about 10 to about 18 carbon atoms; and further the molecules comprise a branched primary alkyl moiety or moieties having at least about 1, but not more than 3, carbon atoms. In addition, the surfactant mixture has an average total number of carbon atoms for the branched primary alkyl moieties of less than 14.5, preferably within the range of from about 12 to 14.5. Thus, the present invention mixtures comprise at least one branched primary alkyl sulfate surfactant compound having a longest linear carbon chain of not less than 9 carbon atoms or more than 17 carbon atoms, and the average total number of carbon atoms for the branched primary alkyl chains is within the range of about 12 to 14.5, preferably from about 12 to about 14 and most preferably from about 12 to about 13.5.

For example, a C14 total carbon primary alkyl sulfate surfactant having 11 carbon atoms in the backbone must have 1, 2, or 3 branching units (i.e., R, $R^1$ and/or $R^2$) whereby total number of carbon atoms in the molecule is 14. In this example, the C14 total carbon requirement may be satisfied equally by having, for example, one propyl branching unit or three methyl branching units.

R, $R^1$, and $R^2$ are each independently selected from hydrogen and $C_1$–$C_3$ alkyl (preferably hydrogen or $C_1$–$C_2$ alkyl, more preferably hydrogen or methyl, and most preferably methyl), provided R, $R^1$, and $R^2$ are not all hydrogen. Further, when z is 0, at least R or $R^1$ is not hydrogen.

Although for the purposes of the present invention the surfactant systems of the above formula do not include molecules wherein the units R, $R^1$, and $R^2$ are all hydrogen (i.e., linear non-branched primary alkyl sulfates), it is to be recognized that the present surfactant systems may still further comprise some amount of linear, non-branched primary alkyl sulfate. Further, this linear non-branched primary alkyl sulfate surfactant may be present as the result of the process used to manufacture the surfactant mixture having the requisite one or more mid-chain branched primary alkyl sulfates according to the present invention, or for purposes of formulating personal cleansing compositions some amount of linear non-branched primary alkyl sulfate may be admixed into the final product formulation.

Further it is to be similarly recognized that non-sulfated mid-chain branched alcohol may comprise some amount of the present surfactant system. Such materials may be present as the result of incomplete sulfation of the alcohol used to prepare the alkyl sulfate surfactant, or these alcohols may be separately added to the present personal cleansing compositions along with a mid-chain branched alkyl sulfate surfactant according to the present invention.

M is hydrogen or a salt forming cation depending upon the method of synthesis. Examples of salt forming cations are lithium, sodium, potassium, calcium, magnesium, quaternary alkyl amines having the formula

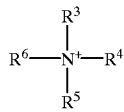

wherein $R^3$, $R^4$, $R^5$ and $R^6$ are independently hydrogen, $C_1$–$C_{22}$ alkylene, $C_4$–$C_{22}$ branched alkylene, $C_1$–$C_6$ alkanol, $C_1$–$C_{22}$ alkenylene, $C_4$–$C_{22}$ branched alkenylene, and mixtures thereof. Preferred cations are ammonium ($R^3$, $R^4$, $R^5$ and $R^6$ equal hydrogen), sodium, potassium, mono-, di-, and trialkanol ammonium, and mixtures thereof. The monoalkanol ammonium compounds of the present invention have $R^3$ equal to $C_1$–$C_6$ alkanol, $R^4$, $R^5$ and $R^6$ equal to hydrogen; dialkanol ammonium compounds of the present invention have $R^3$ and $R^4$ equal to $C_1$–$C_6$ alkanol, $R^5$ and $R^6$ equal to hydrogen; trialkanol ammonium compounds of the present invention have $R^3$, $R^4$ and $R^5$ equal to $C_1$–$C_6$ alkanol, $R^6$ equal to hydrogen. Preferred alkanol ammonium salts of the present invention are the mono-, di- and tri-quaternary ammonium compounds having the formulas: $H_3N^+CH_2CH_2OH$, $H_2N^+(CH_2CH_2OH)_2$, $HN^+(CH_2CH_2OH)_3$. Preferred M is sodium, potassium and the $C_2$ alkanol ammonium salts listed above; the most M preferred is sodium.

Further regarding the above formula, w is an integer from 0 to 10; x is an integer from 0 to 10; y is an integer from 0 to 10; z is an integer from 0 to 10; and w+x+y+z is an integer from 3 to 11.

The preferred surfactant system will be present in the personal cleansing composition at preferably at least about 0.5%, more preferably, at least about 1%, even more preferably at least about 2%, even more preferably still at least about 5%, even more preferably still at least about 8%, most preferably at least about 10%, by weight. Furthermore, the preferred surfactant mixture will be present in the personal cleansing composition at preferably at less than about 45%, more preferably less than about 40%, even more preferably less than about 35%, even more preferably less than about 30%, by weight.

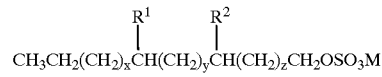

wherein the total number of carbon atoms, including branching, is from 10 to 16, and wherein further for this surfactant mixture the average total number of carbon atoms in the branched primary alkyl moieties having the above formula is within the range of from about 12 to about 14; $R^1$ and $R^2$ are each independently hydrogen or A $C_1$–$C_3$ alkyl; M is a water soluble cation; x is from 0 to 10; y is from 0 to 10; z is from 0 to 10 and x+y+z is from 4 to 10; provided $R^1$ and $R^2$ are not both hydrogen. More preferred are compositions having at least 5% of the mixture comprising one or more mid-chain branched primary alkyl sulfates wherein x+y is equal to 6 and z is at least 1.

Preferably, the mixtures of surfactant comprise at least 5% of a mid chain branched primary alkyl sulfate having $R^1$ and $R^2$ independently hydrogen, methyl, provided $R^1$ and $R^2$ are not both hydrogen; x+y is equal to 5, 6 or 7 and z is at least 1. More preferably the mixtures of surfactant comprise at least 20% of a mid chain branched primary alkyl sulfate having $R^1$ and $R^2$ independently hydrogen or methyl, provided $R^1$ and $R^2$ are not both hydrogen; x+y is equal to 5, 6 or 7 and z is at least 1.

Preferred mid-chain branched primary alkyl sulfate surfactants for use in the personal cleansing compositions defined herein are selected from the group of compounds having the formula:

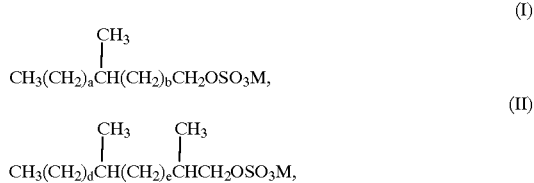

and mixtures thereof; wherein M represents one or more cations; and mixtures thereof, wherein a, b, d, and e are integers, a+b is from 6 to 13, d+e is from 4 to 11 and wherein further when a+b=6, a is an integer from 2 to 5 and b is an integer from 1 to 4;

when a+b=7, a is an integer from 2 to 6 and b is an integer from 1 to 5;

when a+b=8, a is an integer from 2 to 7 and b is an integer from 1 to 6;

when a+b=9, a is an integer from 2 to 8 and b is an integer from 1 to 7;

when a+b=10, a is an integer from 2 to 9 and b is an integer from 1 to 8;

when a+b=11, a is an integer from 2 to 10 and b is an integer from 1 to 9;

when a+b=12, a is an integer from 2 to 11 and b is an integer from 1 to 10;

when a+b=13, a is an integer from 2 to 12 and b is an integer from 1 to 11;

when d+e=4, d is an integer from 2 to 3 and e is an integer from 1 to 2;

when d+e=5, d is an integer from 2 to 4 and e is an integer from 1 to 3;

when d+e=6, d is an integer from 2 to 5 and e is an integer from 1 to 4;

when d+e=7, d is an integer from 2 to 6 and e is an integer from 1 to 5;

when d+e=8, d is an integer from 2 to 7 and e is an integer from 1 to 6;

when d+e=9, d is an integer from 2 to 8 and e is an integer from 1 to 7;

when d+e=10, d is an integer from 2 to 9 and e is an integer from 1 to 8.

when d+e=11, d is an integer from 2 to 10 and e is an integer from 1 to 9.

Wherein the average total number of carbon atoms in the branched primary alkyl moieties having the above formulas is within the range of about 12 to 14.5. Especially preferred mid-chain branched surfactants are those comprising a mixture of compounds having the general formulas from Groups I and II, wherein the molar ratio of compounds according to Group I to Group II is greater than about 4:1, preferably greater than about 9:1 and most preferably greater than about 20:1.

Further, the present surfactant systems may comprise a mixture of linear and branched surfactants wherein the branched primary alkyl sulfates have the formula

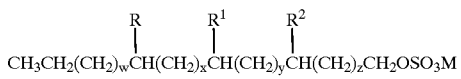

wherein the total number of carbon atoms per molecule, including branching, is from 10 to 17, and wherein further for this surfactant mixture the average total number of carbon atoms in the branched primary alkyl moieties having the above formula is within the range of about 12 to 14.5; R, $R^1$, and $R^2$ are each, independently selected from hydrogen and $C_1$–$C_3$ alkyl, provided R, $R^1$, and $R^2$ are not all hydrogen; M is a water soluble cation; w is an integer from 0 to 10; x is an integer from 0 to 10; y is an integer from 0 to 10; z is an integer from 0 to 10; and w+x+y+z is from 3 to 10; provided that when $R^2$ is a $C_1$–$C_3$ alkyl the ratio of surfactants having z equal to 1 or greater to surfactants having z of 0 is at least about 1:1, preferably at least about 5:1, more preferably at least about 10:1, and most preferably at least about 20:1. Also preferred are surfactant compositions, when $R^2$ is a $C_1$–$C_3$ alkyl, comprising less than about 20%, preferably less than 10%, more preferably less than 5%, most preferably less than 1%, of branched primary alkyl sulfates having the above formula wherein z equals 0.

Preferred mono methyl branched primary alkyl sulfates selected from the group consisting of: 3-methyl undecanol sulfate, 4-methyl undecanol sulfate, 5-methyl undecanol sulfate, 6-methyl undecanol sulfate, 7-methyl undecanol sulfate, 8-methyl undecanol sulfate, 9-methyl undecanol sulfate, 3-methyl dodecanol sulfate, 4-methyl dodecanol sulfate, 5-methyl dodecanol sulfate, 6-methyl dodecanol sulfate, 7-methyl dodecanol sulfate, 8-methyl dodecanol sulfate, 9-methyl dodecanol sulfate, 10-methyl dodecanol sulfate, 3-methyl tridecanol sulfate, 4-methyl tridecanol sulfate, 5-methyl tridecanol sulfate, 6-methyl tridecanol sulfate, 7-methyl tridecanol sulfate, 8-methyl tridecanol sulfate, 9-methyl tridecanol sulfate, 10-methyl tridecanol sulfate, 11-methyl tridecanol sulfate, and mixtures thereof.

Preferred dimethyl branched primary alkyl sulfates are selected from the group consisting of: 2,3-dimethyl undecanol sulfate, 2,4-dimethyl undecanol sulfate, 2,5-dimethyl undecanol sulfate, 2,6-dimethyl undecanol sulfate, 2,7-dimethyl undecanol sulfate, 2,8-dimethyl undecanol sulfate, 2,9-dimethyl undecanol sulfate, 2,3-dimethyl dodecanol sulfate, 2,4-dimethyl dodecanol sulfate, 2,5-dimethyl dodecanol sulfate, 2,6dimethyl dodecanol sulfate, 2,7-dimethyl dodecanol sulfate, 2,8-dimethyl dodecanol sulfate, 2,9-dimethyl dodecanol sulfate, 2,10-dimethyl dodecanol sulfate, and mixtures thereof.

The following branched primary alkyl sulfates comprising 13 carbon atoms and having one branching unit are examples of preferred branched surfactants useful in the present invention compositions:

5-methyldodecylsulfate having the formula:

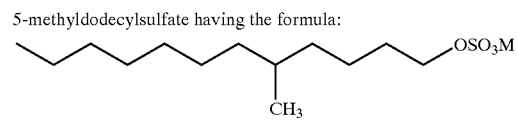

6-methyldodecylsulfate having the formula

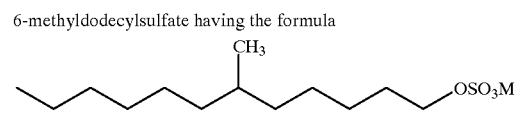

7-methyldodecylsulfate having the formula

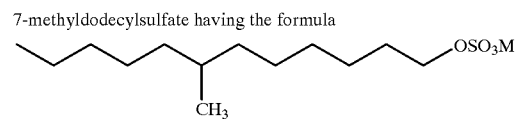

8-methyldodecylsulfate having the formula

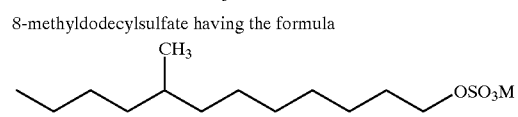

9-methyldodecylsulfate having the formula

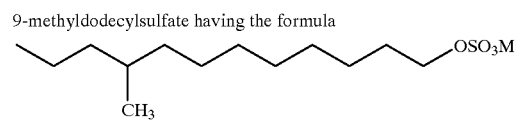

10-methyldodecylsulfate having the formula

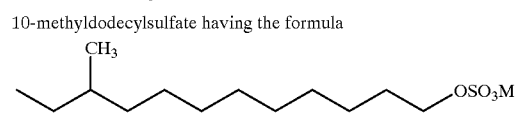

wherein M is preferably sodium.

The following branched primary alkyl sulfates comprising 14 carbon atoms and having two branching units are examples of preferred branched surfactants according to the present invention:

2,5-dimethyldodecylsulfate having the formula:

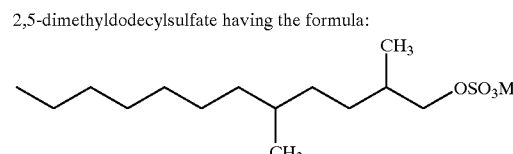

2,6-dimethyldodecylsulfate having the formula

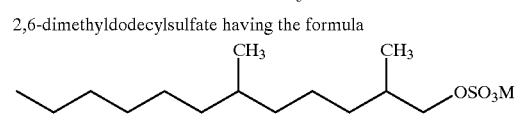

2,7-dimethyldodecylsulfate having the formula

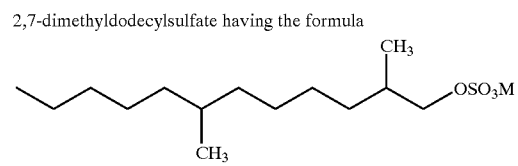

-continued 2,8-dimethyldodecylsulfate having the formula 2,9-dimethyldodecylsulfate having the formula 2,10-dimethyldodecylsulfate having the formula

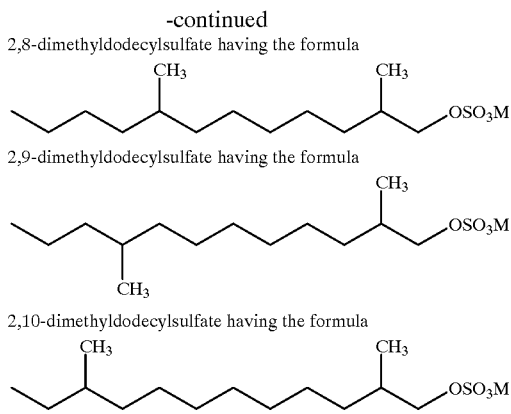

wherein M is preferably sodium.

(2) Mid-chain Branched Primary Alkly Alkoxylated Sulfate Surfactants

The mid-chain branched surfactant system for use in the personal cleansing compositions of the present invention may comprise one or more (preferably a mixture of two or more) mid-chain branched primary alkyl alkoxylated sulfates having the formula:

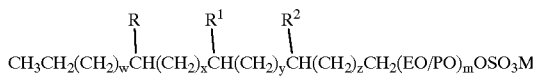

The surfactant mixtures of the present invention comprise molecules having a linear primary alkoxylated sulfate chain backbone (i.e., the longest linear carbon chain which includes the alkoxy-sulfated carbon atom). These alkyl chain backbones comprise from about 10 to about 18 carbon atoms; and further the molecules comprise a branched primary alkyl moiety or moieties having at least about 1, but not more than 3, carbon atoms. In addition, the surfactant mixture has an average total number of carbon atoms for the branched primary alkyl moieties of less than 14.5, preferably within the range of from about 12 to 14.5. Thus, the present invention mixtures comprise at least one branched primary alkyl sulfate surfactant compound having a longest linear carbon chain of not less than 9 carbon atoms or more than 17 carbon atoms, and the average total number of carbon atoms for the branched primary alkyl chains is within the range of from about 12 to 14.5, preferably from about 12 to about 14 and most preferably from about 12 to about 13.5.

For example, a C14 total carbon primary alkyl sulfate surfactant having 11 carbon atoms in the backbone must have 1, 2, or 3 branching units (i.e., R, $R^1$ and/or $R^2$) whereby total number of carbon atoms in the alkyl moiety is 14. In this example, the C14 total carbon requirement may be satisfied equally by having, for example, one propyl branching unit or three methyl branching units.

R, $R^1$, and $R^2$ are each independently selected from hydrogen and $C_1$–$C_3$ alkyl (preferably hydrogen or $C_1$–$C_2$ alkyl, more preferably hydrogen or methyl, and most preferably methyl), provided R, $R^1$, and $R^2$ are not all hydrogen. Further, when z is 0, at least R or $R^1$ is not hydrogen.

Although for the purposes of the present invention the surfactant systems according to the above formula do not include molecules wherein the units R, $R^1$, and $R^2$ are all hydrogen (i.e., linear non-branched primary alkoxylated sulfates), it is to be recognized that the present surfactant system may still further comprise some amount of linear, non-branched primary alkoxylated sulfate. Further, this linear non-branched primary alkoxylated sulfate surfactant may be present as the result of the process used to manufacture the surfactant mixture having the requisite mid-chain branched primary alkoxylated sulfates according to the present invention, or for purposes of formulating personal cleansing compositions some amount of linear to non-branched primary alkoxylated sulfate may be admixed into the final product formulation.

It is also to be recognized that some amount of mid-chain branched alkyl sulfate may be present in the surfactant system. This is typically the result of sulfation of non-alkoxylated alcohol remaining following incomplete alkoxylation of the mid-chain branched alcohol used to prepare the alkoxylated sulfate useful herein. It is to be recognized, however, that separate addition of such mid-chain branched alkyl sulfates is also contemplated by the present personal cleansing compositions.

Further it is to be similarly recognized that non-sulfated mid-chain branched alcohol (including polyoxyalkylene alcohols) may comprise some amount of the present invention alkoxylated sulfate-containing surfactant systems. Such materials may be present as the result of incomplete sulfation of the alcohol (alkoxylated or non-alkoxylated) used to prepare the alkoxylated sulfate surfactant, or these alcohols may be separately added to the present personal cleansing compositions along with a mid-chain branched alkoxylated sulfate surfactant according to the present invention.

M is as described hereinbefore.

Further regarding the above formula, w is an integer from 0 to 10; x is an integer from 0 to 10; y is an integer from 0 to 10; z is an integer from 0 to 10; and w+x+y+z is an integer from 3 to 10.

EO/PO are alkoxy moieties, preferably selected from ethoxy, propoxy, and mixed ethoxy/propoxy groups, wherein m is at least about 0.01, preferably within the range of from about 0.1 to about 30, more preferably from about 0.5 to about 10, and most preferably from about 1 to about 5. The $(EO/PO)_m$ moiety may be either a distribution with average degree of alkoxylation (e.g., ethoxylation and/or propoxylation) corresponding to m, or it may be a single specific chain with alkoxylation (e.g., ethoxylation and/or propoxylation) of exactly the number of units corresponding to m.

The preferred surfactant system will be present in the personal cleansing composition at preferably at least about 0.5%, more preferably, at least about 1%, even more preferably at least about 2%, even more preferably still at least about 5%, even more preferably still at least about 8%, most preferably at least about 10%, by weight. Furthermore, the preferred surfactant mixture will be present in the personal cleansing composition at preferably at less than about 45%, more preferably less than about 40%, even more preferably less than about 35%, even more preferably less than about 30%, by weight of the mixture one or more branched primary alkyl alkoxylated sulfates having the formula

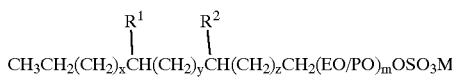

wherein the total number of carbon atoms, including branching, is from 10 to 16, and wherein further for this surfactant mixture the average total number of carbon atoms in the branched primary alkyl moieties having the above formula is within the range of from about 12 to about 14; $R^1$ and $R^2$ are each independently hydrogen or $C_1$–$C_3$ alkyl; M is a water soluble cation; x is from 0 to 10; y is from 0 to 10;

z is from 0 to 10 and x+y+z is from 4 to 10; provided $R^1$ and $R^2$ are not both hydrogen and EO/PO are alkoxy moieties selected from ethoxy, propoxy, and mixed ethoxy/propoxy groups, wherein m is at least about 0.01, preferably within the range of from about 0.1 to about 30, more preferably from about 0.5 to about 10, and most preferably from about 1 to about 5. More preferred are compositions having at least 5% of the mixture comprising one or more mid-chain branched primary alkyl alkoxy sulfates wherein x+y is equal to 6 and z is at least 1.

Preferably, the mixtures of surfactant comprise at least 5% of a mid chain branched primary alkyl sulfate having $R^1$ and $R^2$ independently hydrogen, methyl, provided $R^1$ and $R^2$ are not both hydrogen; x+y is equal to 5, 6 or 7 and z is at least 1. More preferably the mixtures of surfactant comprise at least 20% of a mid chain branched primary alkyl sulfate having $R^1$ and $R^2$ independently hydrogen or methyl, provided $R^1$ and $R^2$ are not both hydrogen; x+y is equal to 5, 6 or 7 and z is at least 1.

Preferred mixtures of mid-chain branched primary alkyl alkoxylated sulfate and linear alkyl alkoxylated sulfate surfactants comprise at least about 5% by weight of one or more mid-chain branched alkyl alkoxylated sulfates having the formula:

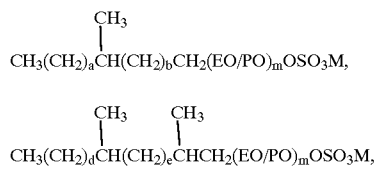

(I)

(II)

and mixtures thereof M represents one or more cations. a, b, d, and e are integers, a+b is from 6 to 13, d+e is from 4 to 11 and wherein further when a+b=6, a is an integer from 2 to 5 and b is an integer from 1 to 4;

when a+b=7, a is an integer from 2 to 6 and b is an integer from 1 to 5;

when a+b=8, a is an integer from 2 to 7 and b is an integer from 1 to 6;

when a+b=9, a is an integer from 2 to 8 and b is an integer from 1 to 7;

when a+b=10, a is an integer from 2 to 9 and b is an integer from 1 to 8;

when a+b=11, a is an integer from 2 to 10 and b is an integer from 1 to 9;

when a+b=12, a is an integer from 2 to 11 and b is an integer from 1 to 10;

when a+b=13, a is an integer from 2 to 12 and b is an integer from 1 to 11;

when d+e=4, d is an integer from 2 to 3 and e is an integer from 1 to 2;

when d+e=5, d is an integer from 2 to 4 and e is an integer from 1 to 3;

when d+e=6, d is an integer from 2 to 5 and e is an integer from 1 to 4;

when d+e=7, d is an integer from 2 to 6 and e is an integer from 1 to 5;

when d+e=8, d is an integer from 2 to 7 and e is an integer from 1 to 6;

when d+e=9, d is an integer from 2 to 8 and e is an integer from 1 to 7;

when d+e=10, d is an integer from 2 to 9 and e is an integer from 1 to 8.

when d+e=11, d is an integer from 2 to 10 and e is an integer from 1 to 9.

The average total number of carbon atoms in the branched primary alkyl moieties having the above formulas is within the range of about 12 to 14.5 and EO/PO are alkoxy moieties selected from ethoxy, propoxy, and mixed ethoxy/propoxy groups, wherein m is at least about 0.01, preferably within the range of from about 0.1 to about 30, more preferably from about 0.5 to about 10, and most preferably from about 1 to about 5. Especially preferred mid-chain branched surfactants are those comprising a mixture of compounds having the general formulas from Groups I and II, wherein the molar ratio of compounds according to Group I to Group II is greater than about 4:1, preferably greater than about 9:1 and most preferably greater than about 20:1.

Further, the present surfactant systems may comprise a mixture of linear and branched surfactants wherein the branched primary alkoxylated sulfates has the formula:

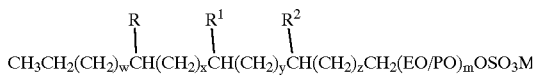

wherein the total number of carbon atoms per molecule, including branching, is from 10 to 17, and wherein further for th is surfactant mixture the average total number of carbon atoms in the branched primary alkyl moieties having the above formula is within the range of about 12 to 14.5; R, $R^1$, and $R^2$ are each independently selected from hydrogen and $C_1$–$C_3$ alkyl, provided R, $R^1$, and $R^2$ are not all hydrogen; M is a water soluble cation; w is an integer from 0 to 10; x is an integer from 0 to 10; y is an integer from 0 to 10; z is an integer from 0 to 10; and w+x+y+z is from 3 to 10; EO/PO are alkoxy moieties, preferably selected from ethoxy, propoxy, and mixed ethoxy/propoxy groups, wherein m is at least about 0.01, preferably within the range of from about 0.1 to about 30, more preferably from about 0.5 to about 10, and most preferably from about 1 to about 5; provided that when $R^2$ is a $C_1$–$C_3$ alkyl the ratio of surfactants having z equal to 1 or greater to surfactants having z of 0 is at least about 1:1, preferably at least about 5:1, more preferably at least about 10:1, and most preferably at least about 20:1. Also preferred are surfactant compositions, when $R^2$ is a $C_1$–$C_3$ alkyl, comprising less than about 20%, preferably less than 10%, more preferably less than 5%, most preferably less than 1%, of branched primary alkyl alkoxylated sulfate having the above formula wherein z equals 0.

Preferred mono-methyl branched primary alkyl ethoxylated sulfates are selected from the group consisting of: 3-methyl dodecanol ethoxylated sulfate, 4-methyl dodecanol ethoxylated sulfate, 5-methyl dodecanol ethoxylated sulfate, 6-methyl dodecanol ethoxylated sulfate, 7-methyl dodecanol ethoxylated sulfate, 8-methyl dodecanol ethoxylated sulfate, 9-methyl dodecanol ethoxylated sulfate, 10-methyl dodecanol ethoxylated sulfate, 3-methyl tridecanol ethoxylated sulfate, 4-methyl tridecanol ethoxylated sulfate, 5-methyl tridecanol ethoxylated sulfate, 6-methyl tridecanol ethoxylated sulfate, 7-methyl tridecanol ethoxylated sulfate, 8-methyl tridecanol ethoxylated sulfate, 9-methyl tridecanol ethoxylated sulfate, 10-methyl tridecanol ethoxylated sulfate, 11-methyl tridecanol ethoxylated sulfate, and mixtures thereof, wherein the compounds are ethoxylated with an average degree of ethoxylation of from about 0.1 to about 10.

Preferred dimethyl branched primary alkyl ethoxylated sulfates selected from the group consisting of: 2,3-dimethyl undecanol ethoxylated sulfate, 2,4-dimethyl undecanol ethoxylated sulfate, 2,5-dimethyl undecanol ethoxylated sulfate, 2,6-dimethyl undecanol ethoxylated sulfate, 2,7-dimethyl undecanol ethoxylated sulfate, 2,8-dimethyl undecanol ethoxylated sulfate, 2,9-dimethyl undecanol ethoxylated sulfate, 2,3-dimethyl dodecanol ethoxylated sulfate, 2,4-dimethyl dodecanol ethoxylated sulfate, 2,5-dimethyl dodecanol ethoxylated sulfate, 2,6-dimethyl dodecanol ethoxylated sulfate, 2,7-dimethyl dodecanol ethoxylated sulfate, 2,8-dimethyl dodecanol ethoxylated sulfate, 2,9-dimethyl dodecanol ethoxylated sulfate, 2,10-dimethyl dodecanol ethoxylated sulfate, and mixtures thereof, wherein the compounds are ethoxylated with an average degree of ethoxylation of from about 0.1 to about 10.

(3) Mid-chain Branched Primary Alkyl Polyoxyalkylene Surfactants

The present branched surfactant system for use in the personal cleansing compositions may comprise one or more mid-chain branched primary alkyl polyoxyalkylene surfactants having the formula

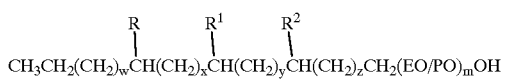

The surfactant mixtures of the present invention comprise molecules having a linear primary polyoxyalkylene chain backbone (i.e., the longest linear carbon chain which includes the alkoxylated carbon atom). These alkyl chain backbones comprise from 10 to 18 carbon atoms; and further the molecules comprise a branched primary alkyl moiety or moieties having at least about 1, but not more than 3, carbon atoms. In addition, the surfactant mixture has an average total number of carbon atoms for the branched primary alkyl moieties within the range of from about 12 to 14.5. Thus, the present invention mixtures comprise at least one polyoxyalkylene compound having a longest linear carbon chain of not less than 9 carbon atoms or more than 17 carbon atoms, and the total number of carbon atoms including branching must be at least 10, and further the average total number of carbon atoms for the branched primary alkyl chains is within the range of from about 12 to 14.5.

For example, a C14 total carbon (in the alkyl chain) primary polyoxyalkylene surfactant having 13 carbon atoms in the backbone must have a methyl branching unit (either R, $R^1$ or $R^2$ is methyl) whereby the total number of carbon atoms in the alkyl moiety is 14.

R, $R^1$, and $R^2$ are each independently selected from hydrogen and $C_1$–$C_3$ alkyl (preferably hydrogen or $C_1$–$C_2$ alkyl, more preferably hydrogen or methyl, and most preferably methyl), provided R, $R^1$, and $R^2$ are not all hydrogen. Further, when z is 0, at least R or $R^1$ is not hydrogen.

Although for the purposes of the present invention the surfactant systems of the above formula do not include molecules wherein the units R, $R^1$, and $R^2$ are all hydrogen (i.e., linear non-branched primary polyoxyalkylenes), it is to be recognized that the present surfactant systems may still further comprise some amount of linear, non-branched primary polyoxyalkylene. Further, this linear non-branched primary polyoxyalkylene surfactant may be present as the result of the process used to manufacture the surfactant mixture having the requisite mid-chain branched primary polyoxyalkylenes according to the present invention, or for purposes of formulating personal cleansing compositions some amount of linear non-branched primary polyoxyalkylene may be admixed into the final product formulation.

The preferred surfactant system will be present in the personal cleansing composition at preferably at least about 0.5%, more preferably, at least about 1%, even more preferably at least about 2%, even more preferably still at least about 5%, even more preferably still at least about 8%, most preferably at least about 10%, by weight. Furthermore, the preferred surfactant mixture will be present in the personal cleansing composition at preferably at less than about 45%, more preferably less than about 40%, even more preferably less than about 35%, even more preferably less than about 30%, by weight of the mixture one or more branched primary alkyl polyoxyalkylenes having the formula

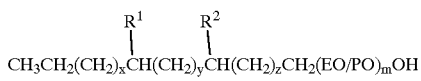

wherein the total number of carbon atoms, including branching, is from 10 to 16, and wherein further for this surfactant mixture the average total number of carbon atoms in the branched primary alkyl moieties having the above formula is within the range of from about 12 to about 14; $R^1$ and $R^2$ are each independently hydrogen or $C_1$–$C_3$ alkyl; x is from 0 to 10; y is from 0 to 10; z is at least 1; and x+y+z is from 4 to 10; provided $R^1$ and $R^2$ are not both hydrogen; and EO/PO are alkoxy moieties selected from ethoxy, propoxy, and mixed ethoxyipropoxy groups, more preferably ethoxy, wherein m is at least about 1, preferably within the range of from about 3 to about 30, more preferably from about 5 to about 20, and most preferably from about 5 to about 15. More preferred are compositions having at least 5% of the mixture comprising one or more mid-chain branched primary polyoxyalkylenes wherein z is at least 2.

Preferably, the mixtures of surfactant comprise at least 0.1%, preferably at least about 0.5%, of a mid chain branched primary alkyl polyoxyalkylene having $R^1$ and $R^2$ independently hydrogen or methyl, provided $R^1$ and $R^2$ are not both hydrogen; x+y is equal to 5, 6 or 7 and z is at least 1.

Preferred mixtures of mid-chain branched primary alkyl polyoxyalkylene surfactants comprise at least about 5% by weight of one or more mid-chain branched alkyl polyoxyalkylenes having the formula:

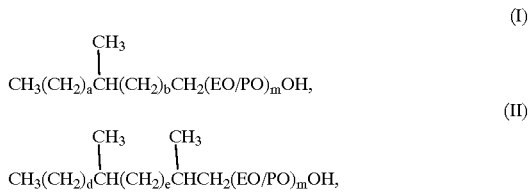

or mixtures thereof; wherein a, b, d, and e are integers, a+b is from 6 to 13, d+e is from 4 to 11 and wherein further
when a+b=6, a is an integer from 2 to 5 and b is an integer from 1 to 4;
when a+b=7, a is an integer from 2 to 6 and b is an integer from 1 to 5;
when a+b=8, a is an integer from 2 to 7 and b is an integer from 1 to 6;
when a+b=9, a is an integer from 2 to 8 and b is an integer from 1 to 7;
when a+b=10, a is an integer from 2 to 9 and b is an integer from 1 to 8;
when a+b=11, a is an integer from 2 to 10 and b is an integer from 1 to 9;

when a+b=12, a is an integer from 2 to 11 and b is an integer from 1 to 10;

when a+b=13, a is an integer from 2 to 12 and b is an integer from 1 to 11;

when d+e=4, d is an integer from 2 to 3 and e is an integer from 1 to 2;

when d+e=5, d is an integer from 2 to 4 and e is an integer from 1 to 3;

when d+e=6, d is an integer from 2 to 5 and e is an integer from 1 to 4;

when d+e=7, d is an integer from 2 to 6 and e is an integer from 1 to 5;

when d+e=8, d is an integer from 2 to 7 and e is an integer from 1 to 6;

when d+e=9, d is an integer from 2 to 8 and e is an integer from 1 to 7;

when d+e=10, d is an integer from 2 to 9 and e is an integer from 1 to 8.

when d+e=11, d is an integer from 2 to 10 and e is an integer from 1 to 9.

and wherein further for this surfactant mixture the average total number of carbon atoms in the branched primary all moieties having the above formulas is within the range of from about 12 to 14.5; and EO/PO are alkoxy moieties selected from ethoxy, propoxy, and mixed ethoxy/propoxy groups, wherein m is at least about 1, preferably within the range of from about 3 to about 30, more preferably from about 5 to about 20, and most preferably from about 5 to about 15.

Further, the present surfactant system may comprise a mixture of linear and branched surfactants wherein the branched primary alkyl polyoxyalkylene has the formula:

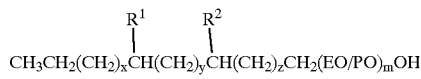

wherein the total number of carbon atoms per molecule, including branching, is from 10 to 17, and wherein further for this surfactant mixture the average total number of carbon atoms in the branched primary alkyl moieties having the above formula is within the range of about 12 to 14.5; R, $R^1$, and $R^2$ are each independently selected from hydrogen and $C_1$–$C_3$ alkyl, provided R, $R^1$, and $R^2$ are not all hydrogen; M is a water soluble cation; w is an integer from 0 to 10; x is an integer from 0 to 10; y is an integer from 0 to 10; z is an integer from 0 to 10; and w+x+y+z is from 3 to 10; EO/PO are alkoxy moieties, preferably selected from ethoxy, propoxy, and mixed ethoxy/propoxy groups, wherein m is at least about 1, preferably within the range of from about 3 to about 30, more preferably from about 5 to about 20, and most preferably from about 5 to about 15; provided that when $R^2$ is a $C_1$–$C_3$ alkyl the ratio of surfactants having z equal to 1 or greater to surfactants having z of 0 is at least about 1:1, preferably at least about 5:1, more preferably at least about 10:1, and most preferably at least about 20:1. Also preferred are surfactant compositions, when $R^2$ is a $C_1$–$C_3$ alkyl, comprising less than about 20%, preferably less than 10%, more preferably less than 5%, most preferably less than 1%, of branched primary alkyl polyoxyalkylene having the above formula wherein z equals 0.

Preferred mono-methyl branched primary alkyl ethoxylates are selected from the group consisting of: 3-methyl dodecanol ethoxylate, 4-methyl dodecanol ethoxylate, 5-methyl dodecanol ethoxylate, 6-methyl dodecanol ethoxylate, 7-methyl dodecanol ethoxylate, 8-methyl dodecanol ethoxylate, 9-methyl dodecanol ethoxylate, 10-methyl dodecanol ethoxylate, 3-methyl tridecanol ethoxylate, 4-methyl tridecanol ethoxylate, 5-methyl tridecanol ethoxylate, 6-methyl tridecanol ethoxylate, 7-methyl tridecanol ethoxylate, 8-methyl tridecanol ethoxylate, 9-methyl tridecanol ethoxylate, 10-methyl tridecanol ethoxylate, 11-methyl tridecanol ethoxylate, and mixtures thereof, wherein the compounds are ethoxylated with an average degree of ethoxylation of from about 5 to about 15.

Preferred dimethyl branched primary alkyl ethoxylates selected from the group consisting of: 2,3-dimethyl undecanol ethoxylate, 2,4-dimethyl undecanol ethoxylate, 2,5-dimethyl undecanol ethoxylate, 2,6-dimethyl undecanol ethoxylate, 2,7-dimethyl undecanol ethoxylate, 2,8-dimethyl undecanol ethoxylate, 2,9-dimethyl undecanol ethoxylate, 2,3-dimethyl dodecanol ethoxylate, 2,4-dimethyl dodecanol ethoxylate, 2,5-dimethyl dodecanol ethoxylate, 2,6-dimethyl dodecanol ethoxylate, 2,7-dimethyl dodecanol ethoxylate, 2,8-dimethyl dodecanol ethoxylate, 2,9-dimethyl dodecanol ethoxylate, 2,10-dimethyl dodecanol ethoxylate and mixtures thereof, wherein the compounds are ethoxylated with an average degree of ethoxylation of from about 5 to about 15.

Preparation of Mid-chain Branched Surfactants

The following reaction scheme outlines a general approach to the preparation of the mid-chain branched primary alcohol useful for alkoxylating and/or sulfating to prepare the mid-chain branched primary alkyl surfactants of the present invention.

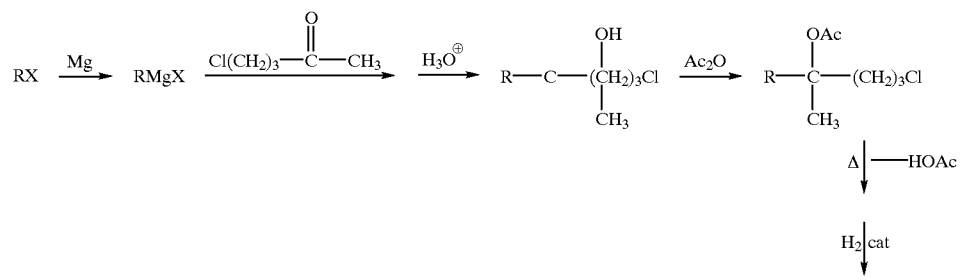

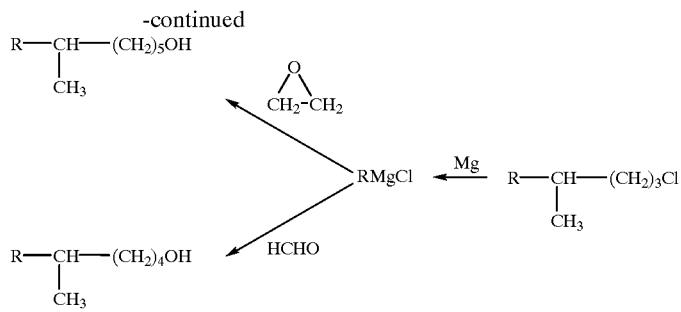

An alkyl halide is converted to a Grignard reagent and the Grignard is reacted with a haloketone. After conventional acid hydrolysis, acetylation and thermal elimination of acetic acid, an intermediate olefin is produced (not shown in the scheme) which is hydrogenated forthwith using any convenient hydrogenation catalyst such as Pd/C.

This route is favorable over others in that the branch, in this illustration a 5-methyl branch, is introduced early in the reaction sequence.

of the alcohol from formulation or ethoxylation can be used to accomplish an iterative chain extension.

The preferred mid-chained branched primary alkyl alkoxylated sulfates (as well as the polyoxyalkylenes and alkyl sulfates, by choosing to only alkoxylate or sulfate the intermediate alcohol produced) of the present invention can also be readily prepared as follows:

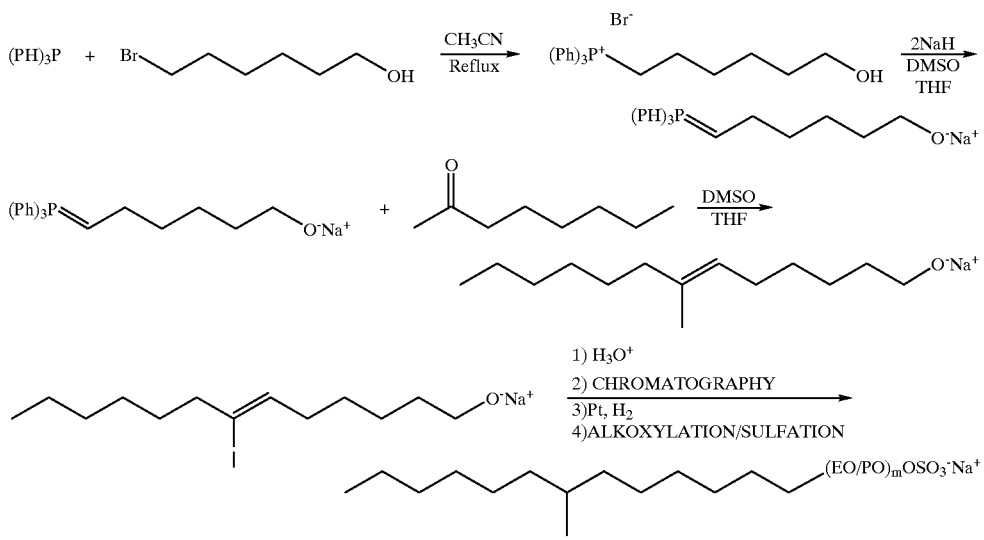

Formulation of the alkyl halide resulting from the first hydrogenation step yields alcohol product, as shown in the scheme. This can be alkoxylated using standard techniques and/or sulfated using any convenient sulfating agent, e.g., chlorosulfonic acid, $SO_3$/air, or oleum, to yield the final branched primary alkyl surfactant. There is flexibility to extend the branching one additional carbon beyond that which is achieved by a single formulation. Such extension can, for example, be accomplished by reaction with ethylene oxide. See "Orignard Reactions of Nonumetallic Substances", M. S. Kharasch and O. Reinmuth, Prentice-Hall, N.Y., 1954; J. Org. Chem., J. Cason and W. R. Winans, Vol. 15 (1950), pp 139–147; J. Org. Chem., J. Cason et al., Vol. 13 (1948), pp 239–248; J. Org Chem., J. Cason et al., Vol. 14 (1949), pp 147–154; and J. Org. Chem., J. Cason et al., Vol. 15 (1950), pp 135–138 all of which are incorporated herein by reference.

In variations of the above procedure, alternate haloketones or Grignard reagents may be used. PBr3 halogenation A conventional bromoalcohol is reacted with triphenylphosphine followed by sodiumn hydride, suitably in dimethylsulfoxide/tetrahydrofainr, to form a Wittig adduct. The Wittig adduct is reacted with an alpha methyl ketone, forming an internally unsaturated methyl-branched alcoholate. Hydrogenation followed by alkoxylation and/or sulfation yields the desired mid-chain branched primary alkyl surfactant. Although the Wittig approach does not allow the practitioner to extend the hydrocarbon chain, as in the Grignard sequence, the Wittig typically affords higher yields. See Agricultural and Biological Chemistry, M. Horiike et al., vol. 42 (1978), pp 1963–1965 included herein by reference.

Any alternative synthetic procedure in accordance with the invention may be used to prepare the branched primary alkyl surfactants. The mid-chain branched primary alkyl surfactants may, in addition be synthesized or formulated in the presence of the conventional homologs, for example any of those which may be formed in an industrial process which produces 2-alkyl branching as a result of hydroformylation.

In certain preferred embodiments of the surfactant mixtures of the present invention, especially those derived from fossil fuel sources involving commercial processes, said surfactant mixtures comprise at least 1 mid-chain branched primary alkyl surfactant, preferably at least 2, more preferably at least 5, most preferably at least 8. Particularly suitable for preparation of certain surfactant mixtures of the present invention are "oxo" reactions wherein a branched chain olefin is subjected to catalytic isomerization and hydroformylation prior to alkoxylation and/or sulfation. The preferred processes resulting in such mixtures utilize fossil fuels as the starting material feedstock. Preferred processes utilize Oxo reaction on olefins (alpha or internal) with a limited amount of branching. Suitable olefins may be made by dimerization of linear alpha or internal olefins, by controlled oligomerization of low molecular weight linear olefins, by skeletal rearrangement of detergent range olefins, by dehydrogenation/skeletal rearrangement of detergent range paraffins, or by Fischer-Tropsch reaction These reactions will in general be controlled to:

1) give a large proportion of olefins in the desired detergent range (while allowing for the addition of a carbon atom in the subsequent Oxo reaction),
2) produce a limited number of branches, preferably mid-chain,
3) produce $C_1$–$C_3$ branches, more preferably ethyl, most preferably methyl,
4) limit or eliminate gem dialkyl branching i.e. to avoid formation of quaternary carbon atoms.

The suitable olefins can undergo Oxo reaction to give primary alcohols either directly or indirectly through the corresponding aldehydes. When an internal olefin is used, an Oxo catalyst is normally used which is capable of prior pre-isomerization of internal olefins primarily to alpha olefins. While a separately catalyzed (i.e. non-Oxo) internal to alpha isomerization could be effected, this is optional. On the other hand, if the olefin-forming step itself results directly in an alpha olefin (e.g. with high pressure Fischer-Tropsch olefins of detergent range), then use of a non-isomerizing Oxo catalyst is not only possible, but preferred.

The process described herein above, with tridecene, gives the more preferred 5-methyl-tridecyl alcohol and therefore surfactants in higher yield than the less preferred 2,4-dimethyldodecyl materials. This mixture is desirable under the metes and bounds of the present invention in that each product comprises a total of 14 carbon atoms with linear alkyl chains having at least 12 carbon atoms.

The following examples provide methods for synthesizing various compounds useful in the present invention compositions. The linear content of these surfactant mixtures exemplified are less than about 5% unless the amount is specified in the specific example, by weight of surfactant mixture.

Example I

Preparation of Sodium 7-methyltridcyl Ethoxylated (E2) and Sulfate

Synthesis of (6-hydroxyhexyl) Triphenylphoshonium Bromide

Into a 5 L, 3 neck round bottom flask fitted with nitrogen inlet , condenser, thermometer, mechanical stirring and nitrogen outlet is added 6-bromo-1-hexanol (500 g, 2.76 mol), triphenylphosphine (768 g, 2.9 mol) and acetonitrile (1800 ml) under nitrogen. The reaction mixture is heated to reflux for 72 hrs. The reaction mixture is cooled to room temperature and transferred into a 5 L beaker. The product is recrystallized from anhydro us ethyl ether (1.5 L) at 10° C. Vacuum filtration followed by washing with ethyl ether and drying in a vacuum oven at 50° C. for 2 hrs. gives 1140 g of the desired product as white crystals.

Synthesis of 7-methyltridecene-1-ol

Into a dried 5 L, 3 neck round bottom flask fitted with mech anical stirring, nitrogen inlet, dropping funnel, thermometer and nitrogen outlet is added 70.2 g of 60% sodium hydride (1.76 mol) in mineral oil. The mineral oil i s removed by washing with hexanes. Anhydrous dimethyl sulfoxide (500 ml) is added to the flask and the mixture is heated to 70° C. until evolution of hydrogen stops. The reaction mixture is cooled to room temperature followed by addition of 1 L of anhydrous tetrahydrofuran. (6-hydroxyhexyl) triphenyiphosp honium bromide (443A4 g, 1 mol) is slurried with warm anhydrous dimethyl sulfoxide (50° C., 500 ml) and slowly added to the reaction mixture through the dropping funnel while keeping it at 25–30°0 C. The mixture is stirred for 30 minutes at room temperature at which time 2-octanone (140.8 g, 1.1 mol) is slowly added through a dropping funnel. Reaction is slightly exothermic and cooling is needed to maintain 25–30° C. The mixture is stirred for 18 hr. and then poured into a 5 L beaker containing 1 L purified water with stirring. The oil phase (top) is allowed to separate out in a separatory funnel and the water phase is removed. The water phase is washed with hexanes (500 ml) and the organic phase is separated and combined with the oil phase from the water wash. The organic mixture is then extracted with water 3 times (500 ml each) followed by vacuum distillation to collect the clear, oily product (100 g) at 140C and 1 mm Hg.

Hydrogenation of 7- methyltridecene-1-ol

Into a 3 L rocking autoclave liner is added 7-methyltridecene-1-ol (108 g, 0.508 mol), methanol (300 ml) and platinum on carbon (10% by weight, 35 g). The mixture is hydrogenated at 180° C. under 1200 psig of hydrogen for 13 hrs., cooled and vacuum filtered through Celite 545 with washing of the Celite 545, suitably with methylene chloride. If needed, the filtration can be repeated to eliminate traces of Pt catalyst, and magnesium sulfate can be used to dry the product. The solution of product is concentrated on a rotary evaporator to obtain a clear oil (104 g).

Alkoxylation of 7-methyltridecanol

Into a dried 1 L 3 neck round bottom flask fitted with a nitrogen inlet, mechanical stirrer, and a y-tube fitted with a thermometer and a gas outlet is added the alcohol from the preceding step. For purposes of removing trace amounts of moisture, the alcohol is sparged with nitrogen for about 30 minutes at 80–100° C. Continuing with a nitrogen sweep, sodium metal is added as the catalyst and allowed to melt with stirring at 120–140° C. With vigorous stirring, ethylene oxide gas is added in 140 minutes while keeping the reaction temperature at 120–140° C. After the correct weight (equal to two equivalents of ethylene oxide) has been added, nitrogen is swept through the apparatus for 20–30 minutes as the sample is allowed to cool. The desired 7-methyltridecyl ethoxylate (average of 2 ethoxylates per molecule) product is then collected.

Sulfation of 7-methyltridecyl Ethoxylate (E2)

Into a dried 1 L 3 neck round bottom flask fitted with a nitrogen inlet, dropping funnel, thermometer, mechanical stirring and nitrogen outlet is added chloroform and 7-methyltridecyl ethoxylate (E2) from the preceding step. Chlorosulfonic acid is slowly added to the stirred mixture while maintaining 25–30° C. temperature with an ice bath. Once HCl evolution has stopped slowly add sodium methoxide (25% in methanol) while keeping temperature at 25–30° C. until a aliquot at 5% concentration in water maintains a pH of 10.5. To the mixture is added hot ethanol (55° C.) and vacuum filtered immediately. The filtrate is concentrated to a slurry on a rotary evaporator, cooled and then poured into ethyl ether. The mixture is chilled to 5° C. and vacuum filtered to provide the desired 7-methyltridecyl ethoxylate (average of 2 ethoxylates per molecule) sulfate, sodium salt, product.

Example II

Preparation of Mid-chain Branched C12,13 and C14,15 Sodium Alcohol Sulfate, Alcohol Ethoxylate, and Sodium Alcohol EthoxY (E1) sulfate from Experimental Clathrated Sasol Alcohol Samples Experimental test mid-branched alcohol samples are derived by urea clathration of C12,13 and C14,15 detergent range alcohol samples from Sasol. Alcohol sulfates, alcohol ethoxylates, and alcohol ethoxy sulfates are prepared from the experimental alcohols. The urea clathration is used to separate the mid-chain branched alcohols from the high levels (35–45% by weight) of conventional linear alcohols present in Sasol's alcohol samples. A 10:1 to 20:1 molar ratio of urea to alcohol is used in the separation. Urea clathration is described in Advanced Organic Chemistry by J. March, 4th ed., Wiley and Sons, 1992, pp. 87–88 and by Takemoto; Sonoda, in Atwood; Davies; MacNicol treatise titled *Inclusion Compounds*, vol. 2, pp. 47–67. The original Sasol alcohol samples are prepared by hydroformylation of alpha olefins produced by Fischer Tropsch process as described in Patent WO 97/01521 and according to the Sasol R&D technical product bulletin dated Oct. 1, 1996 entitled SASOL DETERGENT ALCOHOLS. The clathration procedure reduces the linear content from 35–45%, depending on the sample, down to about 5% by weight, leaving C12,13 and C14,15 alcohols that comprised about 95% branched alcohols. Of the branched alcohols, about 70% are mid-chain branched alcohols according to the present invention and the other 30% are alcohols branched at the 2-carbon position, counting from the oxygen in the alcohol. The sodium forms of alkyl sulfates and alkyl ethoxy (1) sulfates are synthesized for both the experimental mid-branched C12,13 and C14,15 alcohols. Further, alcohol ethoxylates are prepared in the range of 5 to 9 moles of ethoxylation.

Urea Clathration of Sasol C12,13 Alcohol

Into a dry 12 L 3 neck round bottom flask fitted with a mechanical stirrer is added Sasol C12,13 Alcohol (399.8 g, 2.05 mol) and urea (2398.8 g, 39.98 mol) and methanol (7 L). The reagents are allowed to stir at room temperature for about 20 hours. During this time, the urea forms a complex with the linear components of the Sasol alcohol but not with the branched components. After about 20 hours the suspension is filtered through a medium fritted funnel. Vacuum evaporation of the methanol followed by a hexane wash of the urea and vacuum evaporation of the hexane gives 189 g of almost colorless liquid. The GC analysis shows that the recovered alcohol is 5.4% linear and 94.6% branched. Of the branched alcohols, 67.4% are mid-chain branched and 32.6% are branched at the 2-carbon position counting from the oxygen in the alcohol.

Sulfation of Sasol C12.13 Clathrated Alcohol

Into a dried 500 ml 3 neck round bottom flask fitted with a gas inlet, dropping funnel, mechanical stirrer, and a y-tube fitted with a thermometer and a gas outlet is added Sasol C12,13 Clathrated Alcohol (76.8 g, 0.4 mol) and diethyl ether (75 ml). Chlorosulfonic acid (48.9 g, 0.42 mol) is slowly added to the stirred mixture while maintaining a reaction temperature of 5–15° C. with an ice water bath. After the chlorosulfonic acid is added a slow nitrogen sweep and a vacuum (10–15 inches Hg) is begun to remove HCl. Also the reaction is warmed to 30–40° C. with the addition of a warm water bath. After about 45 minutes the vacuum in increased to 25–30 inches Hg and maintained for an additional 45 minutes. The acidic reaction mixture is slowly poured into a vigorously stirred beaker of 25% sodium methoxide (97.2 g, 0.45 mol) and methanol (300 ml) that is cooled in an ice water bath. After pH>12 is confirmed the solution is allowed to stir about 30 minutes then poured into a stainless pan. Most of the solvent is allowed to evaporate overnight in the fume hood. The next morning the sample is transferred to a glass dish and placed in a vacuum drying oven. The sample is allowed to dry all day and overnight at 40–60° C. with 25–30 inches Hg vacuum. After bottling 120 g of yellow tacky solid, the cat SO3 analysis shows the sample is about 94% active. The pH of the sample is about 11.9.

Ethoxylation of Sasol C12,13 Clathrated Alcohol to E1

Into a dried 500 ml 3 neck round bottom flask fitted with a gas inlet, mechanical stirrer, and a y-tube fitted with a thermometer and a gas outlet is added Sasol C12,13 Clathrated Alcohol (134.4 g, 0.7 mol). For the purpose of removing trace amounts of moisture, the alcohol is sparged with nitrogen for about 30 minutes at 60–80° C. Continuing with a nitrogen sweep, sodium metal (0.8 g, 0.04 mol) is added as the catalyst and allowed to melt with stirring at 120–140° C. With vigorous stirring, ethylene oxide gas (30.8 g, 0.7 mol) is added in 60 minutes while keeping the reaction temperature 120–140° C. After the correct weight of ethylene oxide is added, nitrogen is swept through the apparatus for 20–30 minutes as the sample is allowed to cool. The gold liquid product (164.0 g, 0.69 mol) is bottled under nitrogen.

Sulfation of Sasol C12,13 Clathrated Alcohol Ethoxylate (E1)

Into a dried 2 L 3 neck round bottom flask fitted with a gas inlet, dropping funnel, mechanical stirrer, and a y-tube fitted with a thermometer and a gas outlet is added Sasol C12,13 Clathrated Ethoxylate (E1) (160.5 g, 0.68 mol) and diethyl ether (150 ml). Chlorosulfonic acid (82.7 g, 0.71 mol) is slowly added to the stirred mixture while maintaining a reaction temperature of 5–15° C. with an ice water bath. After the chlorosulfonic acid is added a slow nitrogen sweep and a vacuum (10–15 inches Hg) is begun to remove HCl. Also the reaction is warmed to 30–40° C. with the addition of a warm water bath. After about 45 minutes the vacuum in increased to 25–30 inches Hg and maintained for an additional 45 minutes. The acidic reaction mixture is slowly poured into a vigorously stirred beaker of 25% sodium methoxide (164.2 g, 0.76 mol) and methanol (500 ml) that is cooled in an ice water bath. After pH>12 is confirmed the solution is allowed to stir about 30 minutes then poured into a stainless pan. Most of the solvent is allowed to evaporate overnight in the fume hood. The next morning the sample is transferred to a glass dish and placed in a vacuum drying oven. The sample is allowed to dry all day and overnight at 40–60° C. with 25–30 inches Hg vacuum. After bottling 239 g of yellow tacky solid, the cat SO3 analysis shows the sample is about 87% active. The pH of the sample is about 12.6.

Urea Clathration of Sasol C14,15 Alcohol

Into a dry 12 L 3 neck round bottom flask fitted with a mechanical stirrer is added Sasol C14,15 Alcohol (414.0 g, 1.90 mol) and urea (2220.0 g, 37.0 mol) and methanol (3.5

L). The reagents are allowed to stir at room temperature for about 48 hours. During this time, the urea forms a complex with the linear components of the Sasol alcohol but not with the branched components. After about 48 hours the suspension is filtered through a medium fritted funnel. Vacuum evaporation of the methanol followed by a hexane wash of the urea and vacuum evaporation of the hexane gives 220 g of almost colorless liquid. The GC analysis shows that the recovered alcohol is 2.9% linear and 97.1% branched. Of the branched alcohols, 70.4% are mid-chain branched and 29.6% are branched at the 2-carbon position counting from the oxygen in the alcohol.

Sulfation of Sasol C14,15 Clathrated Alcohol

Into a dried 250 ml 3 neck round bottom flask fitted with a gas inlet, dropping funnel, mechanical stirrer, and a y-tube fitted with a thermometer and a gas outlet is added Sasol C14,15 Clathrated Alcohol (43.6 g, 0.2 mol) and diethyl ether (50 ml). Chlorosulfonic acid (24.5 g, 0.21 mol) is slowly added to the stirred mixture while maintaining a reaction temperature of 5–15° C. with an ice water bath. After the chlorosulfonic acid is added a slow nitrogen sweep and a vacuun (10–15 inches Hg) is begun to remove HCl. Also the reaction is warmed to 30–40° C. with the addition of a warm water bath. After about 45 minutes the vacuum in increased to 25–30 inches Hg and maintained for an additional 45 minutes. The acidic reaction mixture is slowly poured into a vigorously stirred beaker of 25% sodium methoxide (49.7 g, 0.23 mol) and methanol (200 ml) that is cooled in an ice water bath. After pH>12 is confirmed the solution is allowed to stir about 30 minutes then poured into a stainless pan. Most of the solvent is allowed to evaporate overnight in the fume hood. The next morning the sample is transferred to a glass dish and placed in a vacuum drying oven. The sample is allowed to dry all day and overnight at 40–60° C. with 25–30 inches Hg vacuum. After bottling 70 g of gold tacky solid, the cat SO3 analysis shows the sample is about 79% active. The pH of the sample is about 13.1.

Ethoxylation of Sasol C14,15 Clathrated Alcohol to E1

Into a dried 500 ml 3 neck round bottom flask fitted with a gas inlet, mechanical stirrer, and a y-tube fitted with a thermometer and a gas outlet is added Sasol C14,15 Clathrated Alcohol (76.3 g, 0.35 mol). For the purpose of removing trace amounts of moisture, the alcohol is sparged with nitrogen for about 30 minutes at 60–80° C. Continuing with a nitrogen sweep, sodium metal (0.4 g, 0.02 mol) is added as the catalyst and allowed to melt with stirring at 120–140° C. With vigorous stirring, ethylene oxide gas (15.4 g, 0.35 mol) is added in 35 minutes while keeping the reaction temperature 120–140° C. After the correct weight of ethylene oxide is added, nitrogen is swept through the apparatus for 20–30 minutes as the sample is allowed to cool. The gold liquid product (90 g, 0.34 mol) is bottled under nitrogen.

Sulfation of Sasol C14,15 Clathrated Alcohol Ethoxylate (E1)

Into a dried 500 ml 3 neck round bottom flask fitted with a gas inlet, dropping funnel, mechanical stirrer, and a y-tube fitted with a thermometer and a gas outlet is added Sasol C14,15 Clathrated Ethoxylate (E1) (86.5 g, 0.33 mol) and diethyl ether (100 ml). Chlorosulfonic acid (40.8 g, 0.35 mol) is slowly added to the stirred mixture while maintaining a reaction temperature of 5–15° C. with an ice water bath. After the chlorosulfonic acid is added a slow nitrogen sweep and a vacuum (10–15 inches Hg) is begun to remove HCl. Also the reaction is warmed to 30–40° C. with the addition of a warm water bath. After about 45 minutes the vacuum in increased to 25–30 inches Hg and maintained for an additional 45 minutes. The acidic reaction mixture is slowly poured into a vigorously stirred beaker of 25% sodium metoxide (82.1 g, 0.38 mol) and methanol (300 ml) that is cooled in an ice water bath. After pH>12 is confirmed the solution is allowed to stir about 30 minutes then poured into a stainless pan. Most of the solvent is allowed to evaporate overnight in the fume hood. The next morning the sample is transferred to a glass dish and placed in a vacuum drying oven. The sample is allowed to dry all day and overnight at 40–60° C. with 25–30 inches Hg vacuum. After bottling 125 g of gold tacky solid, the cat SO3 analysis shows the sample is about 85% active. The pH of the sample is about 11.9.

Example III

Preparation of Sodium 7-methylundecyl Sulfate
Synthesis of 7-methylundecene-1-ol Into a dried 5 L, 3 neck round bottom flask fitted with mechanical stirring, nitrogen inlet, dropping funnel, thermometer and nitrogen outlet is added 70.2 g of 60% sodium hydride (1.76 mol) in mineral oil. The mineral oil is removed by washing with hexanes. Anhydrous dimethyl sulfoxide (500 ml) is added to the flask and the mixture is heated to 70° C. until evolution of hydrogen stops. The reaction mixture is cooled to room temperature followed by addition of 1 L of anhydrous tetrahydrofuran. (6-hydroxyhexyl) triphenylphosphonium bromide (443.4 g, 1 mol, prepared as described previously) is slurried with warm anhydrous dimethyl sulfoxide (50° C., 500 ml) and slowly added to the reaction mixture through the dropping funnel while keeping it at 25–30° C. The mixture is stirred for 30 minutes at room temperature at which time 2-hexanone (110 g, 1.1 mol) is slowly added through a dropping funnel. Reaction is slightly exothermic and cooling is needed to maintain 25–30° C. The mixture is stirred for 18 hr. and then poured into a 5 L beaker containing 1 L purified water with stirring. The oil phase (top) is allowed to separate out in a separatory funnel and the water phase is removed. The water phase is washed with hexanes (500 ml) and the organic phase is separated and combined with the oil phase from the water wash. The organic mixture is then extracted with water 3 times (500 ml each) followed by vacuum distillation to collect the clear, oily product at 140° C. and 1 mm Hg.

Hydrogenation of 7-methylundecene-1-ol

Into a 3 L rocking autoclave liner is added 7-methylundecene-1-ol (93.5 g, 0.508 mol), methanol (300 ml) and platinum on carbon (10% by weight, 35 g). The mixture is hydrogenated at 180° C. under 1200 psig of hydrogen for 13 hrs., cooled and vacuum filtered through Celite 545 with washing of the Celite 545, suitably with methylene chloride. If needed, the filtration can be repeated to eliminate traces of Pt catalyst, and magnesium sulfate can be used to dry the product. The solution of product is concentrated on a rotary evaporator to obtain a clear oil.

Sulfation of 7-methylundecanol

Into a dried 1 L 3 neck round bottom flask fitted with a nitrogen inlet, dropping funnel, thermometer, mechanical stirring and nitrogen outlet is added chloroform (300 ml) and 7-methylundecanol (93 g, 0.5 mol). Chlorosulfonic acid (60 g, 0.509 mol) is slowly added to the stirred mixture while maintaining 25–30° C. temperature with a ice bath. Once HCl evolution has stopped (1 hr.) slowly add sodium methoxide (25% in methanol) while keeping temperature at 25–30° C. until an aliquot at 5% concentration in water maintains a pH of 10.5. To the mixture is added hot ethanol (55° C., 2 L). The mixture is vacuum filtered immediately. The filtrate is concentrated to a slurry on a rotary evaporator, cooled and then poured into 2 L of ethyl ether. The mixture is chilled to 5° C., at which point crystallization occurs, and vacuum filtered. The crystals are dried in a vacuum oven at 50C for 3 hrs. to obtain a white solid.

Example IV

Preparation of Sodium 7-methyldodecyl Sulfate
Synthesis of 7-methyldodecene-1-ol Into a dried 5 L, 3 neck round bottom flask fitted with mechanical stirring, nitrogen inlet, dropping funnel, thermometer and nitrogen outlet is added 70.2 g of 60% sodium hydride (1.76 mol) in mineral oil. The mineral oil is removed by washing with hexanes. Anhydrous dimethyl sulfoxide (500 ml) is added to the flask and the mixture is heated to 70° C. until evolution of hydrogen stops. The reaction mixture is cooled to room temperature followed by addition of 1 L of anhydrous tetrahydrofimin. (6-hydroxyhexyl) triphenylphosphonium bromide (443.4 g, 1 mol, prepared as described previously) is slurried with warm anhydrous dimethyl sulfoxide (50° C., 500 ml) and slowly added to the reaction mixture through the dropping funnel while keeping it at 25–30° C. The mixture is stirred for 30 minutes at room temperature at which time 2-heptanone (125.4 g, 1.1 mol) is slowly added through a dropping funnel. Reaction is slightly exothermic and cooling is needed to maintain 25–30° C. The mixture is stirred for 18 hr. and then poured into a 5 L beaker containing 1 L purified water with stirring. The oil phase (top) is allowed to separate out in a separatory funnel and the water phase is removed. The water phase is washed with hexanes (500 ml) and the organic phase is separated and combined with the oil phase from the water wash. The organic mixture is then extracted with water 3 times (500 ml each) followed by vacuum distillation to collect the clear, oily product at 140C and 1 mm Hg.

Hydrogenation of 7-methyldodecene-1-ol

Into a 3 L rocking autoclave liner is added 7-methyldodecene-1-ol (100.6 g, 0.508 mol), methanol (300 ml) and platinum on carbon (10% by weight, 35 g). The mixture is hydrogenated at 180° C. under 1200 psig of hydrogen for 13 hrs., cooled and vacuum filtered through Celite 545 with washing of the Celite 545, suitably with methylene chloride. If needed, the filtration can be repeated to eliminate traces of Pt catalyst, and magnesium sulfate can be used to dry the product. The solution of product is concentrated on a rotary evaporator to obtain a clear oil.

Sulfation of 7-methyldodecanol

Into a dried 1 L 3 neck round bottom flask fitted with a nitrogen inlet, dropping funnel, thermometer, mechanical siring and nitrogen outlet is added chloroform (300 ml) and 7-methyldodecanol (100 g, 0.5 mol). Chlorosulfonic acid (60 g, 0.509 mol) is slowly added to the stirred mixture while maintaining 25–30° C. temperature with a ice bath. Once HCl evolution has stopped (1 hr.) slowly add sodium methoxide (25% in methanol) while keeping temperature at 25–30° C. until an aliquot at 5% concentration in water maintains a pH of 10.5. To the mixture is added hot ethanol (55° C., 2 L). The mixture is vacuum filtered immediately. The filtrate is concentrated to a slurry on a rotary evaporator, cooled and then poured into 2 L of ethyl ether. The mixture is chilled to 5° C., at which point crystallization occurs, and vacuum filtered. The crystals are dried in a vacuum oven at 50C for 3 hrs. to obtain a white solid (119 g, 92% active by cat $SO_3$ titration).

Example V

Synthesis of Sodium 7-methyltridecyl Sulfate
Sulfation of 7-methyltridecanol

Into a dried 1 L 3 neck round bottom flask fitted with a nitrogen inlet, dropping funnel, thermometer, mechanical stirring and nitrogen outlet is added chloroform (300 ml) and 7-methyltridecanol (107 g, 0.5 mol), prepared as an intermediate in Example I. Chlorosulfonic acid (61.3 g, 0.52 mol) is slowly added to the stirred mixture while maintaining 25–30° C. temperature with an ice bath. Once HCl evolution has stopped (1 hr.) slowly add sodium methoxide (25% in methanol) while keeping temperature at 25–30° C. until a aliquot at 5% concentration in water maintains a pH of 10.5. To the mixture is added methanol (1 L) and 300 ml of 1-butanol. Vacuum filter off the inorganic salt precipitate and remove methanol from the filtrate on a rotary evaporator. Cool to room temperature, add 1 L of ethyl ether and let stand for 1 hour. The precipitate is collected by vacuum filtration. The product is dried in a vacuum oven at 50C for 3 hrs. to obtain a white solid (76 g, 90% active by cat $SO_3$ titration).

Example VI

Synthesis of Sodium 7-methlydodecyl Ethoxylated (E5)

Alkoxylation of 7-methyldodecanol

Into a dried 1 L 3 neck round bottom flask fitted with a nitrogen inlet, mechanical stirrer, and a y-tube fitted with a thermometer and a gas outlet is added 7-methyldodecanol, synthesized as described in Example IV. For purposes of removing trace amounts of moisture, the alcohol is sparged with nitrogen for about 30 minutes at 80–100° C. Continuing with a nitrogen sweep, sodium metal is added as the catalyst and allowed to melt with stirring at 120–140° C. With vigorous stirring, ethylene oxide gas is added in 140 minutes while keeping the reaction temperature at 120–140° C. After the correct weight (equal to five equivalents of ethylene oxide) has been added, nitrogen is swept through the apparatus for 20–30 minutes as the sample is allowed to cool. The desired 7-methyldodecyl ethoxylate (average of 5 ethoxylates per molecule) product is then collected.

Example VII

Preparation of Mid-chain Branched C13 Sodium Alcohol Sulfate, Alcohol Ethoxylate, and Sodium Alcohol Ethoxy (E1) Sulfate from Experimental Shell Research Alcohol Samples Shell Research experimental test C13 alcohol samples are used to make alcohol sulfates, alcohol ethoxylates, and alcohol ethoxy sulfates. These experimental alcohols are ethoxylated and/or sulfated according to the following procedures. The experimental alcohols are made from C12 alpha olefins in this case. The C12 alpha olefins are skeletally rearranged to produce branched chain olefins. The skeletal rearrangement produces a limited number of branches, preferably mid-chain. The rearrangement produces C1–C3 branches, more, preferably ethyl, most preferably methyl. The branched chain olefin mixture is subjected to catalytic hydroformylation to produce the desired branched chain alcohol mixture.

Sulfation of Shell C13 Experimental Alcohol

Into a dried 100 ml 3 neck round bottom flask fitted with a gas inlet, dropping funnel, mechanical stirrer, and a y-tuhe fitted with a thermometer and a gas outlet is added Shell C13 Experimental Alcohol (14.0 g, 0.07 mol) and diethyl ether (20 ml). Chlorosulfonic acid (8.6 g, 0.07 mol) is slowly added to the stirred mixture while maintaining a reaction temperature of 5–15° C. with an ice water bath. After the chlorosulfonic acid is added a slow nitrogen sweep and a vacuum (10–15 inches Hg) is begun to remove HCl. Also the reaction is warmed to 30–40° C. with the addition of a warm water bath. After about 45 minutes the vacuum in increased to 25–30 inches Hg and maintained for an additional 45 minutes. The acidic reaction mixture is slowly poured into a vigorously stirred beaker of 25% sodium methoxide (16.8 g, 0.8 mol) and methanol (50 ml) that is cooled in an ice water bath. After pH>12 is confirmed the solution is allowed to stir about 30 minutes then poured into a stainless pan. Most of the solvent is allowed to evaporate overnight in the fume hood. The next morning the sample is transferred to a glass dish and placed in a vacuum drying oven. The sample is allowed to dry all day and overnight at 40–60° C. with 25–30 inches Hg vacuum. After bottling 21 g of ivory tacky solid, the cat SO3 analysis shows the sample is about 86% active. The pH of the sample is about 11.5.

Ethoxylation of Shell C13 Experimental Alcohol to E1

Into a dried 250 ml 3 neck round bottom flask fitted with a gas inlet, mechanical stirrer, and a y-tube fitted with a thermometer and a gas outlet is added Shell C13 Experimental Alcohol (50.0 g, 0.25 mol). For the purpose of removing trace amounts of moisture, the alcohol is sparged with nitrogen for about 30 minutes at 60–80° C. Continuing with a nitrogen sweep, sodium metal (0.3 g, 0.01 mol) is added as the catalyst and allowed to melt with stirring at 120–140° C. With vigorous stirring, ethylene oxide gas (11.0 g, 0.25 mol) is added in 35 minutes while keeping the reaction temperature 120–140° C. After the correct weight of ethylene oxide is added, nitrogen is swept through the apparatus for 20–30 minutes as the sample is allowed to cool. The yellow liquid product (59.4 g, 0.24 mol) is bottled under nitrogen.

Sulfation of Shell C13 Experimental Alcohol Ethoxylate (E1)

Into a dried 250 ml 3 neck round bottom flask fitted with a gas inlet, dropping funnel, mechanical stirrer, and a y-tube fitted with a thermometer and a gas outlet is added Shell C13 Experimental Ethoxylate (E1) (48.8 g, 0.20 mol) and diethyl ether (50 ml). Chlorosulfonic acid (24.5 g, 0.21 mol) is slowly added to the stirred mixture while maintaining a reaction temperature of 5–15° C. with an ice water bath. After the chlorosulfonic acid is added a slow nitrogen sweep and a vacuum (10–15 inches Hg) is begun to remove HCl. Also the reaction is warmed to 30–40° C. with the addition of a warm water bath. After about 45 minutes the vacuum in increased to 25–30 inches Hg and maintained for an additional 45 minutes. The lo acidic reaction mixture is slowly poured into a vigorously stirred beaker of 25% sodium methoxide (48.8 g, 0.23 mol) and methanol (100 ml) that is cooled in an ice water bath. After pH>12 is confirmed the solution is allowed to stir about 30 minutes then poured into a stainless pan. Most of the solvent is allowed to evaporate overnight in the fume hood. The next morning the sample is transferred to a glass dish and placed in a vacuum drying oven. The sample is allowed to dry all day and overnight at 40–60° C. with 25–30 inches Hg vacuum. After bottling 64.3 g of ivory tacky solid, the cat SO3 analysis shows the sample is about 92% active. The pH of the sample is about 10.8.

The following two analytical methods for characterizing branching in the present invention surfactant compositions are useful:

1) Separation and Identification of Components in Fatty Alcohols (prior to alkoxylation or after hydrolysis of alcohol sulfate for analytical purposes). The position and length of branching found in the precursor fatty alcohol materials is determined by GC/MS techniques [see: D. J. Harvey, Biomed, Environ. Mass Spectrom (1989). 18(9), 719–23; D. J. Harvey, J. M. Tiffany, J. Chromatogr. (1984), 301(1), 173–87; K. A. Karlsson, B. E. Samuelsson, G. O. Steen, Chem. Phys. Lipids (1973), 11(1), 17–38].

2) Identification of Separated Fatty Alcohol Alkoxy Sulfate Components by MS/MS. The position and length of branching is also determinable by Ion Spray-MS/MS or FAB-MS/MS techniques on previously isolated fatty alcohol sulfate components.

The average total carbon atoms of the branched primary alkyl surfactant, herein can be calculated from the hydroxyl value of the precursor fatty alcohol mix or from the hydroxyl value of the alcohols recovered by extraction after hydrolysis of the alcohol sulfate mix according to common procedures, such as outlined in "Bailey's Industrial Oil and Fat Products", Volume 2, Fourth Edition, edited by Daniel Swemn, pp. 440–441.

Conventional Personal Cleansing Additive:

The conventional personal cleansing composition of the present invention additionally contains a conventional personal cleansing additive. The conventional personal cleansing additive are present from about 0.001% to about 49.9% by weight. Preferably, the conventional personal cleansing additive will be present from at least about 0.5%, more preferably, at least about 1%, even more preferably at least about 2%, by weight. Additionaly, the conventional personal cleansing additives can also be present at least about 5%, at least about 8% and at least about 10%, by weight but it is more preferable that the conventional personal cleansing additive be present in at least about 2% by weight. Furthermore, the conventional personal cleansing additive will be preferably present in the personal cleansing composition at preferably at less than about 45%, more preferably less than about 40%, even more preferably less than about 35%, even more preferably less than about 30%, even more preferably less than about 20%, by weight. This conventional personal cleansing additive is selected from the group comprising;

a) conditioning agent b) conventional personal care polymer;

c) antidandruff agent d) cosurfactant; and e) mixtures thereof.

These conventional personal cleansing additives are just some of the possible ingredients which can be conventionally added to personal cleansing compositions.

The conditioning agents, (a), useful in the present invention can be further selected from the group comprising 1) non-volatile hydrocarbons conditioning agents;

2) silicone conditioning agents; and 3) mixtures thereof.

The conventional personal care polymers, (b), useful in the present invention can be further selected from the group comprising i) deposition polymers;

ii) styling polymers and solvent;

iii) dispersed phase polymers; and iv) mixtures thereof.

a) Conditioning Agent

The personal cleansing compositions of the present invention comprise from about 0.005% to about 20%, preferably from about 0.01% to about 10%, more preferably from about 0.1% to about 5%, and even more preferably from about 0.5% to about 3% of dispersed particles of a nonvolatile hair or skin conditioning agent. Suitable hair or skin conditioning agents include nonvolatile silicone conditioning agents, non-volatile hydrocarbon conditioning agents, and mixtures thereof.

Insoluble conditioning agents which can be used in the present invention are of two different particle size ranges. The "smaller" particle conditioning agents require the use of a deposition polymer, while the "larger" particles do not require a deposition polymer, but the personal cleansing composition may optionally contain a deposition polymers for other reasons. The "smaller" particles have a mean particle size range below about 2 microns, preferably below about 1 micron, more preferably below about 0.5 microns, most preferably below about 0.3 microns. The particles can be below about 0.15 microns, and even below about 0.05 microns, but are preferably greater than about 0.01 microns. The "larger" particles have a mean particle size range from about 5 um to about 2000 um. For hair care applications, the average particles size is preferably from about 5 um to about 500 um, more preferably from about 10 um to about 200 um, even more preferably form about 15 um to about 100 um, and most preferably from 20 um to about 75 um. For skin care applications, the average particle size may preferably ranges from about 500 um to about 2000 um, more preferably from about 600 um to about 1500 um, even more preferably from about 800 um to about 1200 um.

As used herein, average particle size of the conditioning agent particles may be measured within the personal cleansing compositions by light scattering methods well known in the art for determining average particle size for emulsified liquids. One such method involves the use of a Horiba LA-910 particle size analyzer.

For more information and additional examples of conditioning agents see copending U.S. patent applications Ser. No. 08/733,046, filed on Oct. 16th, 1996 and U.S. patent application Ser. No. 08/738,156, filed on Oct. 25th, 1996. See also U.S. patent application Ser. No. 4,741,855. Al three of these references are incorporated herein by reference.

1) Nonvolatile Silicone Conditioning Agents Preferred conditioning agents useful herein include nonvolatile, dispersed silicone conditioning agents. By nonvolatile is meant that the silicone conditioning agent exhibits very low or no significant vapor pressure at ambient conditions, e.g., 1 atmosphere at 25° C. The nonvolatile silicone conditioning agent preferably has a boiling point at ambient pressure of above about 250° C., preferably of above about 260° C., and more preferably of above about 275° C. By dispersed is meant that the conditioning agent forms a separate, discontinuous phase from the aqueous carrier such as in the form of an emulsion or a suspension of droplets.

The nonvolatile silicone hair conditioning agents suitable for use herein preferably have a viscosity of from about 1,000 to about 2,000,000 centistokes at 25° C., more preferably from about 10,000 to about 1,800,000, and even more preferably from about 100,000 to about 1,500,000. The viscosity can be measured by means of a glass capillary viscometer as set forth in Dow Corning Corporate Test lo Method CTM0004, Jul. 20, 1970, which is incorporated by reference herein in its entirety. Suitable silicone fluids include polyalkyl siloxanes, polyaryl siloxanes, polyalkylaryl siloxanes, polyether siloxane copolymers, and mixtures thereof. Other nonvolatile silicones having hair conditioning properties can also be used.

The silicones herein also include polyalkyl or polyaryl siloxanes with the following structure:

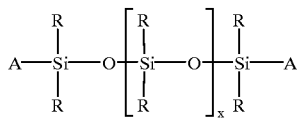

wherein R is alkyl or aryl, and x is an integer from about 7 to about 8,000. "A" represents groups which block the ends of the silicone chains. The alkyl or aryl groups substituted on the siloxane chain (R) or at the ends of the siloxane chains (A) can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable A groups include hydroxy, methyl, methoxy, ethoxy, propoxy, and aryloxy. The two R groups on the silicon atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicones are available, for example, from the General Electric Company in their ViscasilR and SF 96 series, and from Dow Coming in their Dow Corning 200 series.

Polyalkylaryl siloxane fluids can also be used and include, for example, polymethylphenylsiloxanes. These siloxanes are available, for example, from the General Electric Company as SF 1075 methyl phenyl fluid or from Dow Corning as 556 Cosmetic Grade Fluid.

Especially preferred, for enhancing the shine characteristics of hair, are highly arylated silicones, such as highly phenylated polyethyl silicone having refractive indices of about 1.46 or higher, especially about 1.52 or higher. When these high refractive index silicones are used, they should be mixed with a spreading agent, such as a surfactant or a silicone resin, as described below to decrease the surface tension and enhance the film forming ability of the material.

The silicones that can be used include, for example, a polypropylene oxide modified polydimethylsiloxane although ethylene oxide or mixtures of ethylene oxide and propylene oxide can also be used. The ethylene oxide and polypropylene oxide level should be surfficiently low so as not to interfere with the dispersibility characteristics of the silicone. These material are also known as dimethicone copolyols.

Other silicones include amino substituted materials. Suitable alkylamino substituted silicones include those represented by the following structure (II)

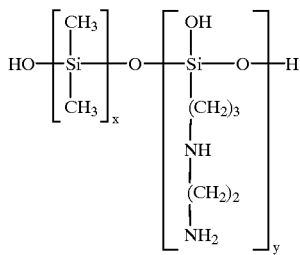

wherein x and y are integers which depend on the molecular weight, the average molecular weight being approximately between 5,000 and 10,000. This polymer is also known as "amodimethicone".

Suitable cationic silicone fluids include those represented by the formula (III)

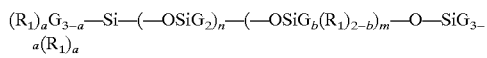

in which G is chosen from the group consisting of hydrogen, phenyl, OH, $C_1$–$C_8$ alkyl and preferably methyl; a denotes 0 or an integer from 1 to 3, and preferably equals 0; b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R_1$ is a monovalent radical of formula $CqH_{2q}L$ in which q is an integer from 2 to 8 and L is chosen from the groups —$N(R_2)CH_2$—$CH_2$—$N(R^2)_2$
—$N(R^2)_2$
—$N(R_2)_3A^-$
—$N(R_2)CH_2$—$CH_2$—$NR_2H_2A^-$ in which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

An especially preferred cationic silicone corresponding to formula (III) is the polymer known as "trimethylsilylamodimethicone", of formula (IV):

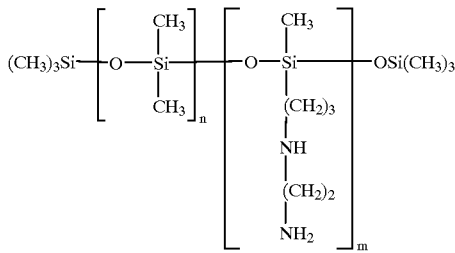

In this formula n and m are selected depending on the exact molecular weight of the compound desired.

Other silicone cationic polymers which can be used in the personal cleansing compositions are represented by the formula (V):

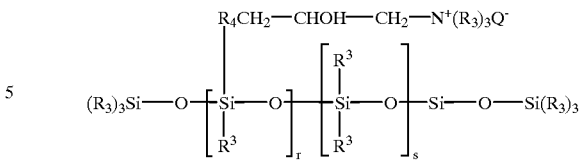

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56."

References disclosing suitable silicones include U.S. Pat. No. 2,826,551, to Geen; U.S. Pat. No. 3,964,500, to Drakoff, issued Jun. 22, 1976; U.S. Pat. No. 4,364,837, to Pader; and British Patent No. 849,433, to Woolston, all of which are incorporated herein by reference in their entirety. Also incorporated herein by reference in its entirety is "Silicon Compounds" distributed by Petrarch Systems, Inc., 1984. This reference provides an extensive, though not exclusive, listing of suitable silicones.

Another silicone hair conditioning material that can be especially useful is a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicones. This overlap is not intended as a limitation on any of these materials. Silicone gums are described by Petrarch, Id., and others including U.S. Pat. No. 4,152,416, to Spitzer et al., issued May 1, 1979 and Noll, Walter, *Chemistry and Technology of Silicones*, New York: Academic Press 1968. Also describing silicone gums are General Electric Silicone Rubber Product Data Sheets SE 30, SE 33, SE 54 and SE 76. All of these described references are incorporated herein by reference in their entirety. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Also useful are silicone resins, which are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a surfficient level of trifunctional and tetrafunctional siloxane monomer units, and hence, a surfficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art. Without being limited by theory, it is believed that the silicone resins can enhance deposition of other silicones on the hair and can enhance the glossiness of hair with high refractive index volumes.

Other useful silicone resins are silicone resin powders such as the material given the CTFA designation polymethylsilsequioxane, which is commercially available as Tospearl™ from Toshiba Silicones.

Background material on silicones, including sections discussing silicone fluids, gums, and resins, as well as the manufacture of silicones, can be found in Encyclopedia of Polymer Science and Engineering, Volume 15, Second Edition, pp 204–308, John Wiley & Sons, Inc., 1989, which is incorporated herein by reference in its entirety.

Silicone materials and silicone resins in particular, can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

2)Nonvolatile Hydrocarbon Conditioning Agents Other suitable hair conditioning agents suitable for use in the personal cleansing composition include nonvolatile organic conditioning agents. Suitable nonvolatile organic conditioning agents for use in the composition are those conditioning agents that are known or otherwise effective for use as hair or skin conditioning agent.

The nonvolatile hydrocarbons for use in the personal cleansing composition may be saturated or unsaturated, and may be straight, cyclic or branched chain. By nonvolatile is meant that the hydrocarbon conditioning agent exhibits very low or no significant vapor pressure at ambient conditions, e.g., 1 atmosphere at 25° C. The nonvolatile hydrocarbon agent preferably has a boiling point at ambient pressure of above about 250° C., preferably above about 260° C., and more preferably of above about 275° C. The nonvolatile hydrocarbons preferably have from about 12 to about 40 carbon atoms, more preferably from about 12 to about 30 carbon atoms, and most preferably from about 12 to about 22 carbon atoms. Also encompassed herein are polymeric hydrocarbons of alkenyl monomers, such as polymers of $C_2$–$C_{12}$ alkenyl monomers, including 1-alkenyl monomers such as polyalphaolefin monomers. These polymers can be straight or branched chain polymers. The straight chain polymers will typically be relatively short in length, having a total number of carbon atoms as described above in this paragraph. The branched chain polymers can have substantially higher chain lengths. Also useful herein are the various grades of mineral oils. Mineral oils are liquid mixtures of hydrocarbons that are obtained from petroleum.

Specific examples of suitable nonvolatile hydrocarbons include, but are not limited to, paraffin oil, mineral oil, dodecane, isododecane, hexadecane, isohexadecane, eicosene, isoeicosene, tridecane, triglyceride oils, tetradecane, polyoctene, polydecene, polydodecene, products of polymerization of mixtures of $C_{2-12}$ monomers, for example the polymer produced by the polymerization of polyoctene, polydecene and polydodecene, and mixtures thereof. Isododecane, isohexadeance, and isoeicosene are commercially available as Permethyl 99A, Permethyl 101A, and Permethyl 1082, from Presperse, South Plainfield, N.J. A copolymer of isobutene and normal butene is commercially available as Indopol H-100 from Amoco Chemicals. Preferred among these hydrocarbons are mineral oil, isododecane, isohexadecane, polybutene, polyisobutene, and mixtures thereof.

Optional Suspending Agent The personal cleansing compositions of the present invention may further comprise a suspending agent at concentrations effective for suspending the optional conditioning agent, or other water-insoluble material, in dispersed form in the personal cleansing compositions. Such concentrations range from about 0.1% to about 10%, preferably from about 0.5% to about 5.0%, by weight of the personal cleansing compositions.

Optional suspending agents include crystalline suspending agents that can be categorized as acyl derivatives, long chain amine oxides, or combinations thereof, concentrations of which range from about 0.3% to about 5.0%, preferably from about 0.5% to about 3.0%, by weight of the personal cleansing compositions. When used in the personal cleansing compositions, these suspending agents are present in crystalline form. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Nortlfield, Ill., USA).

Examples of suitable long chain amine oxides for use as suspending agents include alkyl ($C_{16}$–$C_{22}$) dimethyl amine oxides, e.g., stearyl dimethyl amine oxide Other suitable suspending agents include xanthan gum at concentrations ranging from about 0.3% to about 3%, preferably from about 0.4% to about 1.2%, by weight of the personal cleansing compositions. The use of xanthan gum as a suspending agent in silicone containing personal cleansing compositions is described, for example, in U.S. Pat. No. 4,788,006, which description is incorporated herein by reference. Combinations of long chain acyl derivatives and xanthan gum may also be used as a suspending agent in the personal cleansing compositions. Such combinations are described in U.S. Pat. No. 4,704,272, which description is incorporated herein by reference.

Other suitable suspending agents include carboxyvinyl polymers. Preferred among these polymers are the copolymers of acrylic acid crosslinked with polyallylsucrose as described in U.S. Pat. No. 2,798,053, which description is incorporated herein by reference. Examples of these polymers include Carbopol 934, 940, 941, and 956, available from B. F. Goodrich Company.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Other suitable suspending agents may be used in the personal cleansing compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydorxethylcellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

b) Conventional Personal Care Polymer:

The personal cleansing compositions of the present invention comprise from about 0.01% to about 20%, preferably from about 0.05% to about 10%, more preferably from about 0.1% to about 5%, and even more preferably from about 0.1% to about 3% of a conventional personal care polymer. Suitable conventional personal care polymers include:

i) deposition polymers;

ii) styling polymers and solvent;

iii) dispersed phase polymers; and iv) mixtures thereof.

i) Deposition Polymer

The personal cleansing compositions of the present invention can additionally comprise an organic deposition polymer as a deposition aid. It can be present at levels of from about 0.01 to about 5%, preferably from about 0.05 to about 1%, more preferably from about 0.08% to about 0.5% by weight. The polymer may be a homopolymer or be formed from two or more types of monomers. The molecular weight of the polymer will generally be between about 25,000 and about 10,000,000, preferably between about 100,000 and about 5,000,000, more preferably in the range between about 300,000 to about 3,000,000 and most preferably from about 500,000 to about 2,000,000. Preferably the deposition polymer is a cationic polymer and preferably will have cationic nitrogen containing groups such as quaternary ammonium or protonated amino groups, or a mixture thereof. It is preferred that when the deposition polymer is present there is additionally present in the composition a hair conditioning agent, antidandruff agent, styling polymer or mixtures thereof, all of which are defined hereafter. Alternatively the deposition polymer can be used independantly, that is on its own, in the personal cleansing composition.

See copending U.S. patent applications Ser. No. 08/852,166, filed on May 6$^{th}$, 1997; application Ser. No. 08/738,156 filed on Oct. 25th, 1996, all of which are incorporated herein by reference, for exemplification of deposition polymers.

The cationic charge density has been found to need to be at least 0.1 meq/g, preferably above 0.5 and most preferably above 0.8 or higher. The cationic charge density should not exceed 5 meq/g, it is preferably less than 3 and more preferably less than 2 meq/g. The charge density can be measured using the Kjeldahl method and should be within the above limits at the desired pH of use, which will in general be from about 3 to 9 and preferably between 4 and 8.

The concentration of the deposition polymer in the personal cleansing when it is a cationic polymer is preferably from about 0.025% to about 3%, more preferably from about 0.05% to about 2%, even more preferably from about 0.1% to about 1%, by weight of the personal cleansing composition.

Any anionic counterions can be use in association with the cationic polymers so long as the polymers remain soluble in water, in the personal cleansing composition, or in a coacervate phase of the personal cleansing composition, and so long as the counterions are physically and chemically compatible with the essential components of the personal cleansing composition or do not otherwise unduly impair product performance, stability or aesthetics. Non limiting examples of such counterions include halides (e.g., chlorine, fluorine, bromine, iodine), sulfate and methylsulfate.

The cationic nitrogen-containing moiety of the cationic polymer is generally present as a substituent on all, or more typically on some, of the monomer units thereof. Thus, the cationic polymer for use in the personal cleansing composition includes homopolymers, copolymers, terpolymers, and so forth, of quaternary ammonium or cationic amine-substituted monomer units, optionally in combination with non-cationic monomers referred to herein as spacer monomers. Non limiting examples of such polymers are described in the *CTFA Cosmetic Ingredient Dictionary*, 3rd edition, edited by Estrin, Crosley, and Haynes, (The Cosmetic, Toiletry, and Fragrance Association, Inc., Washington, D.C. (1982)), which description is incorporated herein by reference.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate; vinyl caprolactone and vinyl pyrrolidine. The alkyl and dialkyl substituted monomers preferably have C1–C7 alkyl groups, more preferably C1–C3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the personal cleansing. In general secondary and tertiary amines, especially tertiary, are preferred.

Amines substituted vinyl monomers and amines can be polymerized in the amine form and then converted to ammonium by quaternization.

Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoallyl methacrylate, triallyl methacryloxyalkyl ammonium salt, trialkyl acryloxyalkyl ammonium sale, diallyl quaternary ammonium salts, and vinyl quaternary ammonium monomers having cyclic cationic nitrogen-containg rings such as pyridinium, imidazolium, and quaternized pyirolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$ alkyls.

The cationic polymers hereof can comprise mixtures of monomer units derived from amine-and/or quaternary ammonium-substituted monomer and/or compatible spacer monomers.

Suitable cationic deposition polymers include, for example: copolymers of 1-vinyl-2-pyrrolidine and 1-vinyl-3-methyl-imidazolium salt (e.g., Chloride salt) (referred to in the industry by the Cosmetic, Toiletry, and Fragrance Association, "CTFA" as Polyquatemium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA and Polyquaternium-11) such as those commercially from ISP Corporation (Wayne, N.J., USA) under the GAFQUAT tradename (e.g., GAFQAT 755N); cationic diallyl quaternary ammonium-containing polymers including, for example, dimethyldiallyammonium chloride homopolymer and copolymers of acrylamide and dimethyldiallyammoniumn chloride, referred to in the industry (CTFA) as Polyquaternium 6 and Polyquaternium 7, respectively; and mineral acid salts of amino-alkyl esters of homo-and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives. Cationic polysaccharide polymer materials suitable for use herein include those of the formula:

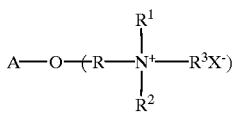

wherein: A is an anhydroglucose residual group, such as starch or cellulose anhydroglucose residual, R is an alkylene oxyalkiene, polyoxyalkylene, or hydroxyalkylene group, or combination thereof, $R^1$, $R^2$ and $R^3$ independently are alkyl, aryl, alkylaryl, arylalkyl, alkoxyalllyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N.J., USA) in their Polymer JR (trademark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other cationic polymers that can be used include cationic guar gum derivatives, such as guar hydroxypropyltrimonium chloride (commercially available from Celanese Corp. in their Jaguar trade mark series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein).

The deposition polymer does not have to be soluble in the personal cleansing composition. Preferably, however, the cationic polymer is either soluble in the personal cleansing composition, or in a complex coacervate phase in the personal cleansing composition formed by the cationic polymer and anionic material. Complex coacervates of the cationic polymer can be formed with anionic surfactants or with anionic polymers that can optionally be added to the composition hereof (e.g., sodium polystyrene sulfonate).

Coacervate formation is dependent upon a variety of criteria such as molecular weight, concentration, and ratio of interacting ionic materials, ionic strength (including modification of ionic strength, for example, by addition of salts), charge density of the cationic and anionic species, pH, and temperature. Coacervate systems and the effect of these parameters have been described, for example, by J. Caelles, et al., "Anionic and Cationic Compounds in Mixed Systems", *Cosmetics & Toiletries*, Vol. 106, April 1991, pp 49–54, C. J. van Oss, "Coacervation, Complex-Coacervation and Flocculation", *J. Dispersion Science and Technology*, Vol. 9 (5,6), 1988–89, pp 561–573, and D. J. Burgess, "Practical Analysis of Complex Coacervate Systems", *J. of Colloid and Interface Science*, Vol. 140, No. 1, November 1990, pp 227–238, which descriptions are incorporated herein by reference.

It is believe to be particularly advantageous for the cationic polymer to be present in the personal cleansing in a coacervate phase, or to form a coacervate phase upon application or rinsing of the personal cleansing to or from the hair. Complex coacervates are believed to more readily deposit on the hair. Thus, in general, it is preferred that the cationic polymer exist in the personal cleansing as a coacervate phase or form a coacervate phase upon dilution. If not already a coacervate in the personal cleansing, the cationic polymer will preferably exist in a complex coacervate form in the personal cleansing upon dilution with water to a water:personal cleansing composition rate ratio of about 20:1, more preferably at about 10:1, even more preferably at about 8:1.

Techniques for analysis of formation of complex coacervates are known in the art. For example, microscopic analyses of the personal cleansing compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phase dispersed in the composition.

Preferably the deposition polymer is selected from the group comprising cationic hydroxyalkyl cellulose ethers and cationic guar derivatives. Particularly preferred deposition polymers are Jaguar C13S, Jaguar C15, Jaguar C17 and Jaguar C16 and Jaguar C162. Other preferred cationic cellulose ethers include Polymer JR400, JR30M and JR125. Surfactant soluble Conditioning Oil The shampoo compositions of the present invention may additionally comprise a low viscosity, surfactant soluble conditioning oil which is solubilized in the surfactant component as an additional hair conditioning agent for use in combination with the cationic hair conditioning polymer described hereinbefore. The concentration of the low viscosity, surfactant soluble oil ranges from about 0.05% to about 3%, preferably from about 0.08% to about 1.5%, more preferably from about 0.1% to about 1%, by weight of the shampoo composition.

The low viscosity, surfactant soluble, conditioning oils are water insoluble, water dispersible, liquids selected from the group consisting of hydrocarbon oils and fatty esters, or combinations thereof, wherein the surfactant soluble conditioning oil has a viscosity of from about 1 to about 300 centipoise, preferably from about 1 to about 150 centipoise, more preferably from about 2 to about 50 centipoise, as measured at 40° C. according to ASTM D-445.

It has been found that these low viscosity surfactant soluble conditioning oils provide the shampoo composition with improved conditioning performance when used in combination with the deposition polymers described herein. These surfactant soluble conditioning oils are believed to be solubilized in the surfactant micelles of the shampoo composition. It is also believed that this solubilization into the surfactant micelles contributes to the improved hair conditioning performance of the shampoo compositions herein.

Suitable surfactant soluble conditioning oils for use in the shampoo composition include hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers thereof. Straight chain hydrocarbon oils preferably contain from about 12 to about 19 carbon atoms. Branched chain hydrocarbon oils, including hydrocarbon polymers, can and typically will contain more than 19 carbon atoms. Specific non limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and combinations thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, sold by Permethyl Corporation. Hydrocarbon polymers such as polybutene and polydecene, especially polybutene, can also be used.

Other surfactant soluble conditioning oils for use in the shampoo composition include a liquid polyolefin such as a liquid polyalphaolefin or a hydrogenated liquid polyalphaolefin. Polyolefins suitable for use in the shampoo composition herein are prepared by polymerization of olefenic monomers containing from about 4 to about 14 carbon atoms, preferably from about 6 to about 12 carbon atoms. Polyalphaolefins are preferred, and are prepared by polymerization of 1-alkene monomers having from about 4 to about 14 carbon atoms, preferably from about 6 to about 12 carbon atoms.

Non limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and combinations thereof. Also suitable for preparing the polyolefin liquids are olefin-containing refinery feedstocks or effluents. Preferred, however, are the hydrogenated alpha-olefin monomers having from about 4 to about 14 carbon atoms, or combinations thereof, examples of which include 1-hexene to 1-hexadecenes and combinations thereof, and preferably are 1-octene to 1-tetradecene or combinations thereof.

(ii) Styling Polymer

The personal cleansing compositions of the present invention may additionally contain a water-insoluble hair styling polymer, concentrations of which range from about 0.1% to about 10%, preferably from about 0.3% to about 7%, more preferably from about 0.5% to about 5%, by weight of the composition. These styling polymers provide the personal cleansing composition of the present invention with hair styling performance by providing a thin polymeric film on the hair after application from a personal cleansing composition. The polymeric film deposited on the hair has adhesive and cohesive strength, as is understood by those skilled in the art. It is essential that when a styling polymer is present in the personal cleansing compositions of the invention that a solvent, defined hereafter, is also present in the It is preferred that when a styling polymer is present a deposition polymer be also present. This combination improves deposition and retention of the styling polymer. Furthermore, it is preferred that when the personal cleansing composition contains a styling polymer it is preferred that a cationic spreading agent be present.

Many such polymers are known in the art, including water-insoluble organic polymers and water-insoluble silicone-grafted polymers, all of which are suitable for use in the personal cleansing composition herein provided that they also have the requisite features or characteristics described hereinafter. Such polymers can be made by conventional or otherwise known polymerization techniques well known in the art, an example of which includes free radical polymerization.

See copending U.S. patent application Ser. No. 08/738, 211, filed on Oct. 25th, 1996 which is incorporated herein by reference.

Examples of suitable organic and silicone grafted polymers for use in the personal cleansing composition of the present invention are described in greater detail hereinafter.

Organic styling polymer The styling polymers suitable for use in the personal cleansing composition of the present invention include organic styling polymers well known in the art. The organic styling polymers may be homopolymers, copolymers, terpolymers or other higher polymers, but must comprise one or more polymerizable hydrophobic monomers to thus render the resulting styling polymer hydrophobic and water-insoluble as defined herein. The styling polymers may therefore further comprise other water soluble, hydrophilic monomers provided that the resulting styling polymers have the requisite hydrophobicity and water insolubility.

As used herein, the term "hydrophobic monomer" refers to polymerizable organic monomers that can form with like monomers a water-insoluble homopolymer,. and the term "hydrophilic monomer" refers to polymerizable organic monomers that can form with like monomers a water-soluble homopolymer.

The organic styling polymers preferably have a weight average molecular weight of at least about 20,000, preferably greater than about 25,000, more preferably greater than about 30,000, most preferably greater than about 35,000. There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 2,000,000. Preferably, the weight average molecular weight will be between about 20,000 and about 2,000,000, more preferably between about 30,000 and about 1,000,000, and most preferably between about 40,000 and about 500,000.

The organic styling polymers also preferably have a glass transition temperature (Tg) or crystalline melting point (Tm) of at least about −20° C., preferably from about 20° C. to about 80° C., more preferably from about 20° C. to about 60° C. Styling polymers having these Tg or Tm values form styling films on hair that are not unduly sticky or tacky to the touch. As used herein, the abbreviation "Tg" refers to the glass transition temperature of the backbone of the polymer, and the abbreviation "Tm" refers to the crystalline melting point of the backbone, if such a transition exists for a given polymer. Preferably, both the Tg and the Tm, if any, are within the ranges recited hereinabove.

The organic styling polymers are carbon chains derived from polymerization of hydrophobic monomers such as ethylenically unsaturated monomers, cellulosic chains or other carbohydrate-derived polymeric chains. The backbone may comprise ether groups, ester groups, amide groups, urethanes, combinations thereof, and the like.

The organic styling polymers may further comprise one or more hydrophilic monomers in combination with the hydrophobic monomers described herein, provided that the resulting styling polymer has the requisite hydrophobic character and water-insolubility. Suitable hydrophilic monomers include, but are not limited to, acrylic acid, methacrylic acid, N,N-dimethylacrylamide, dimethyl aminoethyl methacrylate, quaternized dimethylaminloethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), salts of any acids and amines listed above, and mixtures thereof. Preferred hydrophilic monomers include acrylic acid, N,N-dimethyl acrylamide, dimethylaminoethyl methacrylate, quaternized dimethyl aminoethyl methacrylate, vinyl pyrrolidone, salts of acids and amines listed above, and combinations thereof.

Suitable hydrophobic monomers for use in the organic styling polymer include, but are not limited to, acrylic or methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-tri methyl-1-hexanol, 1-decanol, 1-dodecanol, 1-hexadecanol, 1-octa decanol, and the like, the alcohols having from about 1 to about 18 carbon atoms, preferably from about 1 to about 12 carbon atoms; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof. Preferred hydrophobic monomers include n-butyl methacrylate, isobutyl methacrylate, t-butyl acrylate, t-butyl methacrylate, 2-ethylhexyl methacrylate, methyl methacrylate, vinyl acetate, and mixtures thereof, more preferably t-butyl acrylate, t-butyl methacrylate, or combinations thereof.

The styling polymers for use in the personal cleansing composition preferably comprise from about 20% to 100%, more preferably from about 50% to about 100%, even more preferably from about 60% to about 100%, by weight of the hydrophobic monomers, and may further comprise from zero to about 80% by weight of hydrophilic monomers. The particular selection and combination of monomers for incorporation into the styling polymer will help determine its formulational properties. By appropriate selection and combination of, for example, hydrophilic and hydrophobic monomers, the styling polymer can be optimized for physical and chemical compatibility with the selected styling polymer solvent described hereinafter and other components of the personal cleansing composition. The selected monomer composition of the organic styling polymer must, however, render the styling polymer water-insoluble but may be soluble in the selected solvent described hereinafter. In this context, the organic styling polymer is soluble in the solvent if the organic polymer is solubilized in the solvent at 25° C. at the polymer and solvent concentrations of the personal cleansing formulation selected. However, a solution of the organic styling polymer and solvent may be heated to speed up solubility of the styling polymer in the solvent. Such styling polymer and solvent formulation, including the selection of monomers for use in the styling polymer, to achieve the desired solubility is well within the skill of one in the art.

Examples of preferred organic styling polymers include t-butyl acrylate/2-ethylhexyl acrylate copolymers having a weight/weight ratio of monomers of about 95/5, about 90/10, about 80/20, about 70/30, about 60/40, and about 50/50; t-butyl acrylate/2-ethylhexyl methacrylate copolymers having a weight/weight ratio of monomers of about 95/5, about 90/10, about 80/20, about 70/30, about 60/40, and about 50/50; t-butyl methacrylate/2thylhexyl acrylate copolymers having a weight/weight ratio of monomers of about 95/5, about 90/10, about 80/20, about 70/30, about 60/40, and about 50/50; t-butyl methacrylate/2-ethylhexyl methacrylate copolymers having a weight/weight ratio of monomers of about 95/5, about 90/10, about 80/20, about 70/30, about 60/40, and about 50/50; t-butyl ethacrylate/2-ethylhexyl methacrylate copolymers having a weight/weight ratio of monomers of about 95/5, about 90/10, about 80/20, about 70/30, about 60/40, and about 50/50; vinyl pyrrolidone/vinyl acetate copolymers having a weight/weight ratio of monomers of about 10/90, and about 5/95; and mixtures thereof.

Especially preferred polymers are t-butyl acrylate/2-ethylhexyl methacrylate copolymers having a weight/weight ratio of monomers of about 95/5, about 90/10, about 80/20, about 70/30, about 60/40, and about 50/50; t-butyl methacrylate/2-ethylhexyl methacrylate copolymers having a weight/weight ratio of monomers of about 95/5, about 90/10, about 80/20, about 70/30, about 60/40, and about 50/50; and mixtures thereof.

Examples of other suitable styling polymers are described in U.S. Pat. No. 5,120,531, to Wells et al., issued Jun. 9, 1992; U.S. Pat. No. 5,120,532, to Wells et al., issued Jun. 9, 1992; U.S. Pat. No. 5,104,642, to Wells et al., issued Apr. 14, 1992; U.S. Pat. No. 4,272,511, to Papantoniou et al., issued Jun. 9, 1981; U.S. Pat. No. 4,963,348, to Bolich et al., issued Oct. 16, 1990 and U.S. Pat. No. 4,196,190, to Gehman et al., issued Apr. 1, 1980, which descriptions are incorporated herein by reference.

Silicone-grafted styling iolymer Other suitable styling polymers for use in the personal cleansing composition of the present invention are silicone-grafted hair styling resins. These polymers may be used alone or in combination with the organic styling polymers described hereinbefore. Many such polymers suitable for use in the personal cleansing composition herein are known in the art. These polymers are characterized by polysiloxane moieties covalently bonded to and pendant from a polymeric carbon-based backbone.

The backbone of the silicone-grafted polymer is preferably a carbon chain derived from polymerization of ethylenically unsaturated monomers, but can also be cellulosic chains or other carbohydrate-derived polymeric chains to which polysiloxane moieties are pendant. The backbone can also include ether groups, ester groups, amide groups, urethane groups and the like. The polysiloxane moieties can be substituted on the polymer or can be made by co-polymerization of polysiloxane-containing polymerizable monomers (e.g. ethylenically unsaturated monomers, ethers, and/or epoxides) with non-polysiloxane-containing polymerizable monomers.

The silicone-grafted styling polymers for use in the personal cleansing composition comprise "silicone-containing" (or "polysiloxane-containing") monomers, which form the silicone macromer pendant from the backbone, and non-silicone-containing monomers, which form the organic backbone of the polymer. That is a siloxane monomer grafted to the hair styling polymer.

Preferred silicone-grafted polymers comprise an organic backbone, preferably a carbon backbone derived from ethylenically unsaturated monomers, such as a vinyl polymeric backbone, and a polysiloxane macromer (especially preferred are polydialkylsiloxane, most preferably polydimethylsiloxane) grafted to the backbone. The polysiloxane macromer should have a weight average molecular weight of at least about 500, preferably, from about 1,000 to about 100,000, more preferably from about 2,000 to about 50,000, most preferably about 5,000 to about 20,000. Organic backbones contemplated include those that are derived from polymerizable, ethylenically unsaturated monomers, including vinyl monomers, and other condensation monomers (e.g., those that polymerize to form polyamides and polyesters), ring-opening monomers (e.g., ethyl oxazoline and caprolactone), etc. Also contemplated are backbones based on cellulosic chains, ether-containing backbones, etc.

Preferred silicone grafted polymers for use in the personal cleansing composition comprise monomer units derived from: at least one free radically polymerizable ethylenically unsaturated monomer or monomers and at least one free radically polymerizable polysiloxane-containing ethylenically unsaturated monomer or monomers.

The silicone grafted polymers suitable for use in the personal cleansing composition generally comprise from about 1% to about 50%, by weight, of polysiloxane-containing monomer units and from about 50% to about 99% by weight, of non-polysiloxane-containing monomers. The non-polysiloxane-containing monomer units can be derived from the hydrophilic and/or hydrophobic monomer units described hereinbefore.

The styling polymer for use in the personal cleansing composition can therefore comprise combinations of the hydrophobic and/or polysiloxane-containing monomer units described herein, with or without hydrophilic comonomers as described herein, provided that the resulting styling polymer has the requisite characteristics as described herein.

Suitable polymerizable polysiloxane-containing monomers include, but are not limited to, those monomers that conform to the formula:

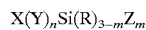

wherein X is an ethylenically unsaturated group copolymerizable with the hydrophobic monomers described herein, such as a vinyl group; Y is a divalent linking group; R is a hydrogen, hydroxyl, lower alkyl (e.g. $C_1$–$C_4$), aryl, alkaryl, alkoxy, or alkylamino; Z is a monovalent siloxane polymeric moiety having a number average molecular weight of at least about 500, which is essentially unreactive under copolymerization conditions, and is pendant from the vinyl polymeric backbone described above; n is 0 or 1; and m is an integer from 1 to 3. These polymerizable polysiloxane-containing monomers have a weight average molecular weight as described above.

A preferred polysiloxane-containing monomer conforms to the formula:

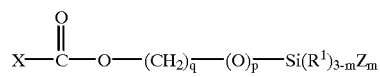

wherein m is 1, 2 or 3 (preferably m=1); p is 0 or 1; q is an integer from 2 to 6; $R^1$ is hydrogen, hydroxyl, lower alkyl, alkoxy, alkylamino, aryl, or alkaryl (preferably $R^1$ is alkyl); X conforms to the formula

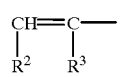

wherein $R^2$ is hydrogen or —COOH (preferably $R^2$ is hydrogen); $R^3$ is hydrogen, methyl or —CH$_2$COOH (preferably $R^3$ is methyl); Z conforms to the formula:

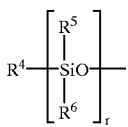

wherein $R^4$, $R^5$, and $R^6$ independently are lower alkyl, alkoxy, alkylamino, aryl, arylalkyl, hydrogen or hydroxyl (preferably $R^4$, $R^5$, and $R^6$ are alkyls); and r is an integer of about 5 or higher, preferably about 10 to about 1500 (most preferably r is from about 100 to about 250). Most preferably, $R^4$, $R^5$, and $R^6$ are methyl, p=0, and q=3.

Another preferred polysiloxane monomer conforms to either of the following formulas

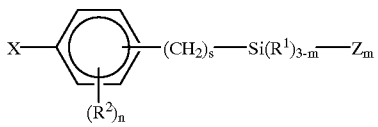

or

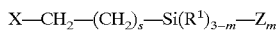

wherein: s is an integer from 0 to about 6, preferably 0, 1, or 2, more preferably 0 or 1; m is an integer from 1 to 3, preferably 1; $R^2$ is C1–C10 alkyl or C7–C10 alkylaryl, preferably C1–C6 alkyl or C7–C10 alkylaryl, more preferably C1–C2 alkyl; n is an integer from 0 to 4, preferably 0 or 1, more preferably 0.

The silicone grafted styling polymers suitable for use in the personal cleansing composition preferably comprise from about 50% to about 99%, more preferably from about 60% to about 98%, most preferably from about 75% to about 95%, by weight of the polymer, of non-silicone macromer-containing monomer units, e.g. the total hydrophobic and hydrophilic monomer units described herein, and from about 1% to about 50%, preferably from about 2% to about 40%, more preferably from about 5% to about 25%, of silicone macromer-containing monomer units, e.g. the polysiloxane-containing monomer units described herein. The level of hydrophilic monomer units can be from about 0% to about 70%, preferably from about 0% to about 50%, more preferably from about 0% to about 30%, most preferably from about 0% to about 15%; the level of hydrophobic monomer units, can be from 30% to about 99%, preferably from about 50% to about 98%, more preferably from about 70% to about 95%, most preferably from about 85% to about 95%.

Examples of some suitable silicone grafted polymers for use in the personal cleansing composition herein are listed below. Each listed polymer is followed by its monomer composition as weight part of monomer used in the synthesis:

(i) t-butylacrylatye/t-butyl-methacrylate/2-ethylhexyl-methacrylate/PDMS macromer-20,000 molecular weight macromer 31/27/32/10

(ii) t-butylmethacrylate/2-ethylhexyl-methacrylate/PDMS macromer-15,000 molecular weight macromer 75/10/15

(iii) t-butylmethacrylate/2-ethylhexyl-acrylate/PDMS macromer-10,000 molecular weight macromer 65/15/20

(iv) t-butylacrylate/2-ethylhexyl-acrylate/PDMS macromer-14,000 molecular weight macromer 77/11/12

(v) t-butylacrylate/2-ethylhexyl-methacrylate/PDMS macromer-13,000 molecular weight macromer 81/9/10

Examples of other suitable silicone grafted polymers for use in the personal cleansing composition of the present invention are described in EPO Application 90307528.1, published as EPO Application 0 408 311 A2 on Jan. 11, 1991, Hayama, et al.; U.S. Pat. No. 5,061,481, issued Oct. 29, 1991, Suzuki et al.; U.S. Pat. No. 5,106,609, Bolich et al., issued Apr. 21, 1992; U.S. Pat. No. 5,100,658, Bolich et al., issued Mar. 31, 1992; U.S. Pat. No. 5,100,657, Ansher-Jackson, et al., issued Mar. 31, 1992; U.S. Pat. No. 5,104,646, Bolich et al., issued Apr. 14, 1992; U.S. Ser. No. 07/758,319, Bolich et al, filed Aug. 27, 1991, U.S. Ser. No. 07/758,320, Torgerson et al., filed Aug. 27, 1991, which descriptions are incorporated herein by reference.

Solvent—The personal cleansing composition of the present invention must additionally comprise a volatile solvent for solubilizing the styling polymers, described hereinbefore, when such a styling polymer is present. The solvent helps disperse the styling polymer as water-insoluble fluid particles throughout the personal cleansing composition, wherein the dispersed particles comprise the styling polymer and the volatile solvent. Solvents suitable for this purpose include hydrocarbons, ethers, esters, amines, alkyl alcohols, volatile silicone derivatives and combinations thereof, many examples of which are well known in the art.

The volatile solvent must be water-insoluble or have a low water solubility. The selected styling polymer, however, must also be surfficiently soluble in the selected solvent to allow dispersion of the hair styling polymer and solvent combination as a separate, dispersed fluid phase in the personal cleansing composition.

The solvent suitable for use in the personal cleansing composition must also be a volatile material. In this context, the term volatile means that the solvent has a boiling point of less than about 300° C., preferably from about 90° C. to about 260° C., more preferably from about 100° C. to about 200° C. (at about one atmosphere of pressure).

The concentration of the volatile solvent in the personal cleansing composition must be surfficient to solubilize the hair styling polymer and disperse it as a separate fluid phase in the personal cleansing composition. Such concentrations generally range from about 0.10% to about 10%, preferably from about 0.5% to about 8%, most preferably from about 1% to about 6%, by weight of the personal cleansing composition, wherein the weight ratio of styling polymer to solvent is preferably from about 10:90 to about 70:30, more preferably from about 20:80 to about 65:35, even more preferably from about 30:70 to about 60:40. If the weight ratio of styling polymer to solvent is too low, the lathering performance of the personal. cleansing composition is negatively affected. If the ratio of polymer to solvent is too high, the composition becomes too viscous and causes difficulty in the dispersion of the styling polymer. The hair styling agents should have an average particle diameter in the final personal cleansing product of from about 0.05 to about 100 microns, preferably from about 0.2 micron to about 25 microns. Particle size can be measured according to methods known in the art, including, for example optical microscopy.

Preferred volatile solvents for use in the personal cleansing composition are the hydrocarbon solvents, especially branched chain hydrocarbon solvents. The hydrocarbon solvents may be linear or branched, saturated or unsaturated, hydrocarbons having from about 8 to about 18 carbon atoms, preferably from about to about 16 carbon atoms. Saturated hydrocarbons are preferred, as are branched hydrocarbons. Nonlimiting examples of some suitable linear hydrocarbons include decane, dodecane, decene, tridecene, and combinations thereof. Suitable branched hydrocarbons include isoparaffins, examples of which include commercially available isoparaffins from Exxon Chemical Company such as Isopar H and K ($C_{11}$–$C_{12}$ isoparaffins), and Isopar L ($C_{11}$–$C_{13}$ isoparaffins). Preferred branched hydrocarbons are isohexadecane, isododecane, 2,5-dimethyl decane, isotetradecane, and combinations thereof. Commercially available branched hydrocarbons include Permethyl 99A and 101A (available from Preperse, Inc., South Plainfield, N.J., USA).

Other suitable solvents include isopropanol, butyl alcohol, amyl alcohol, phenyl ethanol, benzyl alcohol, phenyl propanol, ethyl butyrate, isopropyl butyrate, diethyl phthalate, diethyl malonate, diethyl succinate, dimethyl malonate, dimethyl succinate, phenyl ethyl dimethyl carbinol, ethyl-6-acetoxyhexanoate, and methyl (2-pentanyl-3-oxy)cyclopentylacetate, and mixtures thereof. Preferred among such other suitable solvents are diethyl phthalate, diethyl malonate, diethyl succinate, dimethyl malonate, dimethyl succinate, phenylethyl dimethyl carbinol, ethyl-6-acetoxyhexanoate, and mixtures thereof.

Suitable ether solvents are the di($C_5$–$C_7$) alkyl ethers and diethers, especially the di($C_5$–$C_6$) alkyl ethers such as isoamyl ether, dipentyl ether and dihexyl ether.

Other suitable solvents for use in the personal cleansing composition the volatile silicon derivatives such as cyclic or linear polydialkylsiloxane, linear siloxy compounds or silane. The number of silicon atoms in the cyclic silicones is preferably from about 3 to about 7, more preferably about 3 to about 5.

The general formula for such silicones is:

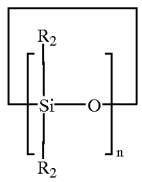

wherein $R_1$ and $R_2$ are independently selected from $C_1$ to $C_8$ alkyl, aryl or alkylaryl and wherein n=3–7. The linear polyorgano siloxanes have from about 2 to 7 silicon atoms and have the general formula:

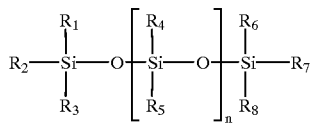

wherein $R_1$, $R_2$, $R_3$, $R_4$, $R_5$, $R_6$, $R_7$ and $R_8$ can independently be saturated or unsaturated $C_1$–$C_8$ alkyl, aryl, alkylaryl, hydroxyalkyl, amino alkyl or alkyl siloxy.

Linear siloxy compounds have the general formula:

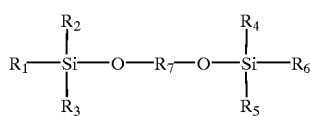

wherein $R_1$, $R_2$, $R_3$, $R_4$, $R_5$, and $R_6$ are independently selected from saturated or unsaturated $C_1$ to $C_7$ alkyl, aryl and alkyl aryl and $R_7$ is $C_1$ to $C_4$ alkylene.

Silane compounds have the general formula:

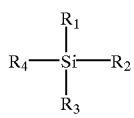

wherein $R_1$, $R_2$, $R_3$, and $R_4$ can independently be selected from $C_1$–$C_8$ alkyl, aryl, alkylaryl, hydroxyalkyl and alkylsiloxy.

Silicones of the above type, both cyclic and linear, are offered by Dow Corning Corporation, Dow Corning 344, 345 and 200 fluids, Union Carbide, Silicone 7202 and Silicone 7158, and Stauffer Chemical, SWS-03314.

The linear volatile silicones generally have viscosities of less than about 5 centistokes at 25° C. while the cyclic materials have viscosities less than about 10 centistokes. Examples of volatile silicones are described in Todd and Byers, "Volatile Silicone Fluids for Cosmetics", Cosmetics and Toiletries, Vol. 91, January, 1976, pp. 27–32, and also in Silicon Compounds, pages 253–295, distributed by Petrarch Chemicals, which descriptions are incorporated herein by reference.

Cationic Spreading Agent The personal cleansing compositions of the present invention may additionally comprise select cationic materials which act for use as spreading agents. The spreading agents for use in the composition are select quaternary ammonium or protonated amino compounds defined in greater detail hereinafter. These select spreading agents are useful to improve spreadability of the water-insoluble styling polymer on the body, for example on the hair. The concentration of the select spreading agents in the composition range from about 0.05% to about 5%, preferably from about 0.1% to about 2%, more preferably from about 0.2% to about 1%, by weight of the personal cleansing composition.

It has been found that the select spreading agents will improve spreadability of a water-insoluble styling polymer when used in the personal cleansing composition of the present invention. In particular, the improved insoluble solvent, water-insoluble styling polymer, and cationic deposition polymer, are especially effective at improving styling performance of the composition. The improved styling performance results from the improved spreading efficiency of water-insoluble styling polymer attributed to the use of the select spreading agent in the composition. onto hair. This improved spreading results in improved styling performance, or allows for formulation of the personal cleansing composition using reduced amounts of styling polymer or cationic deposition polymer.

The select spreading agents are quaternary ammonium or amino compounds having 2, 3 or 4 N-radicals which are substituted or unsubstituted hydrocarbon chains having from about 12 to about 30 carbon atoms, wherein the substituents lo includes nonionic hydrophilic moieties selected from alkoxy, polyoxallylene, alllylamido, hydroxyalkyl, alkylester moieties, and mixtures thereof. Suitable hydrophile-containing radicals include, for example, compounds having nonionic hydrophile moieties selected from the group consisting of ethoxy, propoxy, polyoxyethylene, polyoxypropylene, ethylamido, propylamido, hydroxymethyl, hydroxyethyl, hydroxypropyl, methylester, ethylester, propylester, or mixtures thereof. The select spreading agents are cationic and must be positively charged at the pH of the personal cleansing compositions. Generally, the pH of the personal cleansing composition will be less than about 10, typically from about 3 to about 9, preferably from about 4 to about 8.

Select cationic spreading agents for use in the composition include those corresponding to the to the formula:

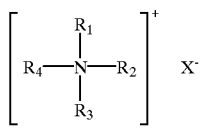

wherein $R_1$, and $R_2$ are independently a saturated or unsaturated, substituted or unsubstituted, linear or branched hydrocarbon chain having from about 12 to about 30 carbon atoms, preferably from about 18 to about 22 carbon atoms, and wherein the hydrocarbon chain can contain one or more hydrophilic moieties selected from the alkoxy, polyoxyalkylene, alkylamido, hydroxyalkyl, alkylester, and mixtures thereof; $R_3$ and $R^4$ are independently a hydrogen, or a saturated or unsaturated, substituted or unsubstituted, linear or branched hydrocarbon chain having from about 1 to about 30 carbon atoms, or a hydrocarbon having from about 1 to about 30 carbon atoms containing one or more aromatic, ester, ether, amido, amino moieties present as substitutents or as linkages in the chain, and wherein the hydrocarbon chain can contain one or more hydrophilic moieties selected from the alkoxy, polyoxyalkylene, alkylamido, hydroxyalkyl, alkylester, and mixtures thereof; and X is a soluble salt forming anion preferably selected from halogen (especially chlorine), acetate, phosphate, nitrate, sulfonate, and alkylsulfate radicals.

An example of a select spreading agent for use in the composition include those corresponding to the formula:

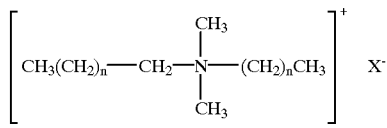

wherein n is from 10–28, preferably 16, and X is a water soluble salt forming anion (e.g., Cl, sulfate, etc.).

Other examples of select cationic spreading agents for use in the composition include those corresponding to the formula:

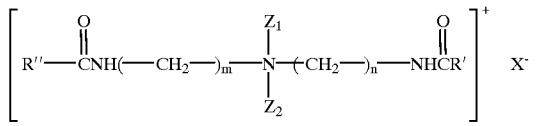

wherein $Z_1$ and $Z_2$ are independently saturated or unsaturated, substituted or unsubstituted, linear or branched hydrocarbons, and preferably $Z_1$ is an alkyl, more preferably methyl, and $Z_2$ is a short chain hydroxyalkyl, preferably hydroxymethyl or hydroxyethyl; n and m are independently integers from 1 to 4, inclusive, preferably from 2 to 3, inclusive, more preferably 2; R' and R" are independently substituted or unsubstituted hydrocarbons, preferably $C_{12}$–$C_{20}$ alkyl or alkenyl; and X is a soluble salt forming anion (e.g., Cl, sulfate, etc.).

Nonlimiting examples of suitable cationic spreading agents include ditallowdimethyl ammonium chloride, ditallowdimethyl ammonium methyl sulfate, dihexadecyl dimethyl ammonium chloride, di-(hydrogenated tallow) dimethyl ammonium chloride, dioctadecyl dimethyl ammonium chloride, dieicosyl dimethyl ammonium chloride, didocosyl dimethyl ammonium chloride, di-(hydrogenated tallow) dimethyl ammonium acetate, dihexadecyl dimethyl ammonium acetate, ditallow dipropyl ammonium phosphate, ditallow dimethyl ammonium nitrate, di-(coconutaalyl) dimethyl ammonium chloride, ditallowamidoethyl hydroxypropylmonium methosulfate (commercially available as Varisoft 238), dihydrogenated tallowamidoethyl hydroxyethylmonium methosulfate (commercially available as Varisoft 110), ditallowamidoethyl hydroxyethyhnonium methosulfate (commercially available as Varisoft 222), and di(partially hardened soyoylethyl) hydroxyethylmonium methosulfate (commercially available as Amiocare EQ-S). Ditallowdimethyl ammonium chloride, ditallowamidoethyl hydroxypropylmonium methosulfate, dihydrogenated tallowamidoethyl hydroxyethylmonium methosulfate, ditallowaridoethyl hydroxyethylmonium methosulfate, and di(partially hardened soyoylethyl) hydroxyethylmonium methosulfate are particularly preferred quaternary ammonium cationic surfactants useful herein.

Other suitable quaternary ammonium cationic surfactants are described in M.C. Publishing Co., *McCutcheion's Detergents & Emulsifiers*, (North American edition 1979); Schwartz, et al., *Surface Active Agents. Their Chemistry and Technology*, New York: Interscience Publishers, 1949; U.S. Pat. No. 3,155,591, to Hilfer, issued Nov. 3, 1964; U.S. Pat. No. 3,929,678 to Laughlin et al., issued Dec. 30, 1975; U.S. Pat. No. 3,959,461 to Bailey et al, issued May 25, 1976; and U.S. Pat. No. 4,387,090 to Bolich Jr., issued Jun. 7, 1983, which descriptions are incorporated herein by reference.

iii) Dispersed Phase Polymers

Another optional component of the present invention is a dispersed phase polymer. Suitable dispersed phase polymers include water soluble nonionic polymers and water soluble anionic polymers. Suitable nonionic polymers include cellulose ethers (e.g., hydroxybutyl methylcellulose, hydroxypropylcellulose, hydroxypropyl methylcellulose, ethylhydroxy ethylcellulose and hydroxyethylcellulose), propylene glycol alginates, polyacrylamide, poly(ethylene oxide), polyvinyl alcohol, polyvinylpyrrolidone, hydroxypropyl guar gum, locust bean gum, amylose, hydroxyethyl amylose, starch and starch derivatives and mixtures thereof. Preferred nonionic polymers include hydroxyethyl cellulose, polyethylene oxide, polyvinyl pyrrolidone, polyvinyl alcohol, polyacrylamide, hydroxypropyl cellulose, ethylhydroxyethyl cellulose, dextran, polypropyleneoxide and hydroxypropyl guar or mixtures thereof.

Suitable anionic water-soluble polymers include carboxymethyl cellulose, carrageenan, xanthum gum polystyrene sulfonate, gum agar, gum ghatti, gum karaya, pectins, alginate salts, as well as poly(acrylic acid) and acrylic or methacrylic acid derivatives such as the alkali metal and ammonium salts of acrylic acid, methacrylic acid. Mixtures of the above anionic water-soluble polymers may also be used.

These polymeric compositions may be homopolymers or they may be copolymers or terpolymers with other copolymerizing monomers known in the art. Examples of copolymerizing monomers known in the art include but are not limited to ethylene, propylene, isobutylene, styrene, polystyrene, alphamethylstyrene, vinyl acetate, vinyl formate, alkyl ethers, acrylonitrile, methacrylonitrile, vinyl chloride, vinylidene chloride, the alkyl acrylates, the alkylmethacrylates, the alkyl fumarates, the alkyl maleates, and other olefinic monomers copolymerizable therewith as long as the resulting polymers are water soluble and phase separate in the compositions of this invention. Copolymers of anionic and nonionic monomers such as acrylic acid and methacrylic acid with acrylamide, methacrylamide, the N-alkyl substituted amides, the N-aminoalkylamides, the corresponding N-alkylaminoallyl substituted amides, the aminoalkyl acrylates, the aminoalkyl methacrylamides, and the N-alkyl substituted aminoalkyl esters of either acrylic or methacrylic acids.

Preferred anionic polymers include polyacrylic acid; sodium carboxy methyl cellulose; polyacrylates; polymethyl acrylate; polysulphates such as polyvinyl sulfate, polystyrene sulfonate, polyphosphates, sodium dextran sulfate, alginate salts and pectate When combined with the aqueous surfactant system and phase separation initiator, described below, the water-soluble nonionic or anionic polymer separates to form aqueous droplets suspended in a continuous aqueous phase. The number average particle size of the polymer droplets can be from 0.1 microns to about 10,000 microns, preferably from about 1.0 micron to about 5000 microns, most preferably from about 5 microns to about 1000 microns.

Most preferred for use in the present invention are ethyl hydroxyethyl cellulose, hydroxyethyl cellulose, hydroxypropyl guar and polystyrene sulfonate.

The herein described polymers are preferably present at a concentration level of above about 0.1%, more preferably from about 0.15% to about 10%, most preferably from about 0.2% to about 2%. mixtures of the anionic and nonionic water-soluble polymers may also be used.

See also copending U.S. patent application Ser. No. 08/786,521, which is incorporated herein by reference.

The personal care compositions of the invention when a dispersed phase polymers is present preferably contain a phase separation initiator, defined herein after.

Phase Separation Initiators The compositions of the present invention may additionally contain a phase separation initiator. By the term "phase separation initiators", as used herein, means electrolytes, amphiphiles or mixtures thereof capable of inducing phase separation when combined with compositions comprising a surfactant system and a nonionic or anionic water-soluble polymer.

By the term "amphiphile" as used herein, means, generally, substances which contain both hydrophilic and hydrophobic (lipophilic) groups. Amphiphiles preferred for use in the present invention are those which generally do not form micelles or liquid crystal phases and include, but are not limited to: amides of fatty acids; fatty alcohols; fatty esters, glycol mono- and di- esters of fatty acids; glyceryl esters.

Amides, including alkanol amides, are the condensation products of fatty acids with primary and secondary amines or alkanolamines to yield products of the general formula:

wherein RCO is a fatty acid radical and R is $C_{8-20}$; X is an alkyl, aromatic or alkanol (CHR'CH$_2$OH wherein R' is H or $C_{1-6}$ alkyl); Y is H, alkyl, alkanol or X. Suitable amides include, but are not limited to , cocamide, lauramide, oleamide and stearamide. Suitable alkanolamides include, but are not limited to, cocamide DEA, cocamide MEA, cocamide SEPA, isostearamide DEA, isostearamide MEA, isostearamide MIPA, lanolinamide DEA, lauramide DEA, lauramide MEA, lauramide MIPA, linoleamide DEA, linoleamide MEA, linoleamide MIPA, myristamide DEA, myristamide MEA, myristamide MIPA, Oleamide DEA, Oleamide MEA, Oleamide MIPA, palmamide DEA, palmamide MEA, palmamide MIPA, palmitamide DEA, palmitamide MEA, palm kermelamide DEA, palm kernelamide MEA, palm kernelamide MIPA, peanutamide MEA, peanutamide MIPA, soyamide DEA, stearamide DEA, stearamide MEA, stearamide MIPA, tallamide DEA, tallowamide DEA, tallowamide MEA, undecylenamide DEA, undecylenamide MEA. The condensation reaction may be carried out with free fatty acids or with all types of esters of the fatty acids, such as fats and oils, and particularly methyl esters. The reaction conditions and the raw material sources determine the blend of materials in the end product and the nature of any impurities.

Fatty alcohols are higher molecular weight, nonvolatile, primary alcohols having the general formula:

$$RCH_2OH$$

wherein R is a $C_{8-20}$ alkyl. They can be produced from natural fats and oils by reduction of the fatty acid COOH—grouping to the hydroxyl function. Alternatively, identical or similarly structured fatty alcohols can be produced according to conventional synthetic methods known in the art. Suitable fatty alcohols include, but are not limited to, behenyl alcohol, $C_{9-11}$ alcohols, $C_{12-13}$ alcohols, $C_{12-15}$ alcohols, $C_{12-16}$ alcohols, $C_{14-15}$ alcohols, caprylic alcohol, cetearyl alcohol, coconut alcohol, decyl alcohol, isocetyl alcohol, isostearyl alcohol, lauryl alcohol, oleyl alcohol, palm kernel alcohol, stearyl alcohol, cetyl alcohol, tallow alcohol, tridecyl alcohol or myristyl alcohol.

Glyceryl esters comprise a subgroup of esters which are primarily fatty acid mono- and di-glycerides or triglycerides modified by reaction with other alcohols and the like. Preferred glyceryl esters are mono and diglycerides. Suitable glyceryl esters and derivatives thereof include, but are not limited to, acetylated hydrogenated tallow glyceride, glyceryl behenate, glyceryl caprate, glyceryl caprylate, glyceryl caprylate/caprate, glyceryl dilaurate, glyceryl dioleate, glyceryl erucate, glyceryl hydroxystearate, glyceryl isostearate, glyceryl lanolate, glyceryl laurate, glyceryl linoleate, glyceryl oleate, glyceryl stearate, glyceryl myristate, glyceryl distearate and mixtures thereof, Also useful as amphiphiles in the present invention are long chain glycol esters or mixtures thereof Included are ethylene glycol esters of fatty acids having from about 8 to about 22 carbon atoms. Fatty esters of the formula RCO—OR' also act as suitable amphiphiles in the compositions of the present invention, where one of R and R' is a $C_{8-22}$ alkyl and the other is a $C_{1-3}$ alkyl.

The amphiphiles of the present invention may also encompass a variety of surface active compounds such as nonionic and cationic surfactants. If incorporated into the compositions of the present invention, these surface active compounds become additional surfactants used as amphilphiles for the purpose of initiating phase separation and are separate and apart from the surfactants of the surfactant system and the alkyl glyceryl sulfonate surfactant of the present invention.

Amphiphiles preferred for use herein include cocamide MEA, cetyl alcohol and stearyl alcohol.

The amphiphiles of the present invention are preferably present in the personal cleansing compositions at levels of from 0 to about 4%. preferably from about 0.5% to about 2%.

Suitable electrolytes include mono-, di- and trivalent inorganic salts as well as organic salts. Surfactant salts themselves are not included in the present electrolyte definition but other salts are. Suitable salts include, but are not limited to, phosphates, sulfates, nitrates, citrates and halides. The counter ions of such salts can be, but are not limited to, sodium, potassium, ammonium, magnesium or other mono-, di and tri valent cation. Electrolytes most preferred for use in the compositions of the present invention include sodium chloride, ammonium chloride, sodium citrate, and magnesium sulfate. It is recognized that these salts may serve as thickening aids or buffering aids in addition to their role as a phase separation initiator. The amount of the electrolyte used will generally depend on the amount of the amphiphile incorporated, but may be used at concentration levels of from about 0.1% to about 4%, preferably from about 0.2% to about 2%.

The amount of phase separation initiator comprising the electrolyte and/or the amphiphile will vary with the type of surfactant and polymer, but is generally present at a level of from about 0.1% to about 5%, preferably from about 0.2% to about 3%.

In view of the essential nature and activity of the phase separation initiators described above, the compositions of the present invention are, preferably, substantially free of materials which would prevent the induction or formation of separate, liquid phases. The term "substantially free", as used here, means that the compositions of the present invention contain no more than about 0.5% of such materials, preferably less than 0.25%, more preferably zero. Such materials typically include ethylene glycol, propylene glycol, ethyl alcohol and the like.

The compositions of the present invention are also preferably substantially free of other ingredients which unduly minimize the formation of separate and distinct liquid phases, especially ingredients which do not provide a significant benefit to the present invention.

c) Antidandruff Agent

The personal cleansing compositions of the present invention can additionally comprise a safe and effective amount of an antidandruff agent. The antidandruff agent provides the personal cleansing compositions with antidandruff activity. The antidandruff agent is preferably a crystalline particulate that is insoluble in, and dispersed throughout, the personal cleansing compositions. Effective concentrations of such antidandruff agents generally range from about 0.1% to about 5%, more preferably from about 0.3% to about 5%, by weight of the personal cleansing compositions.

See also U.S. Pat. No. 4,948,576 to Verdicchio et al, and copending U.S. patent application Ser. No. 08/738,211, filed on Oct. 25th, 1996, Ser. No. 08/622,222, filed on Mar. 27th, 1996 and Ser. No. 08/975,210, Attorney docket No. 5937C, all of which are incorporated herein by reference.

The antidandruff agents which can be used in the personal cleansing compositions of the present invention are divided in to two categories, type (a) and type (b). Type (b) is limited antidandruff agents which are platelet pyridinethione salt crystals (defined hereinafter) and type (a) is any antidandruff agent which is not a platelet pyridinethione salt crystal. Mixtures of antidandruff agents, including one or more of type (a) and/or one or more of type (b), are within the scope of the present invention.

Type (a)—Type (a), as mentioned above includes any antidandruff agents, which is not a platelet pyridinethione salt crystal, such as, sulfur, octopirox, selenium sulfide, ketoconazole and pyridinethione salts. Selenium sulfide is a preferred particulate antidandruff agent for use in the personal cleansing compositions, effective concentrations of which range from about 0.1% to about 5.0%, preferably from about 0.3% to about 2.5%, more preferably from about 0.5% to about 1.5%, by weight of the personal cleansing compositions. Selenium sulfide is generally regarded as a compound having one mole of selenium and two moles of sulfur, although it may also be a cyclic structure, $Se_xS_y$, wherein x+y=8. Average particle diameters for the selenium sulfide (selenium disulfide) are less than 15 um, preferably less than 10 um, as measured by forward laser light scattering device, e.g., Malvern 3600 instrument. Selenium sulfide compounds are well known in the personal cleansing art and are described, for example in U.S. Pat. No. 2,694,668; U.S. Pat. No. 3,152,046; U.S. Pat. No. 4,089,945; and U.S. Pat. No. 4,885,107, which descriptions are incorporated herein by reference.

Pyridinethione antidandruff agents, especially 1-hydroxy-2-pyridinethione salts, are highly preferred particulate antidandruff agents for use in the personal cleansing compositions, concentrations of which range from about 0.1% to about 3%, preferably about 0.3% to about 2%, by weight of the personal cleansing compositions. Preferred pyridinethione salts are those formed from heavy metals such as zinc, tin, cadmium, magnesium, aluminum and zirconium. Zinc salts are most preferred, especially the zinc salt of 1-hydroxy-2-pyridinethione (zinc pyridinethione, ZPT). Other cations such as sodium may also be suitable.

Pyridinethione antidandruff agents are well known in the personal cleansing art, and are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982, which descriptions are incorporated herein by reference.

Sulfur may also be used as the particulate antidandruff agent in the personal cleansing compositions herein. Effective concentrations of the particulate sulfur are generally from about 1% to about 5%, more preferably from about 2% to about 5%, by weight of the compositions.

Octopirox and related salts and derivatives may also be used as the antidandruff agent in the personal cleansing compositions. Such antidandruff agents are soluble in the personal cleansing composition and, therefore, do not disperse throughout the composition as crystalline particulates as do the other antidandruff agents described hereinbefore. Other antidandruff agents such as azoles may also be used. Examples of azole antidandruff agents are: ketoconazole, itraconazole, fluconazole, miconazole, econazole.

Water soluble non-particulate antidandruff substances whose deposition and retention is enhanced by the water-soluble nitrogen containing polymers described herein include (i.e. deposition polymers)

(a) 1-hydroxy-2-pryidoner of the formula

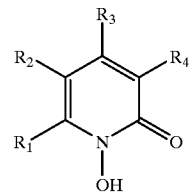

wherein $R_1$ is hydrogen, alkyl of 1 to 17 carbon atoms, cycloalkyl-alkyl of 1 to 4 alkyl carbon atoms, the cycloalkyl groups being optionally substituted by alkyl groups of 1 to 4 carbon atoms, aryl, aralkylof 1 to 4 alkyl carbon atoms, aryl-alkenyl of 2 to 4 alkenyl carbon atoms, aryloxy-alkyl or arylthio-alkyl of 1 to 4 alkyl carbon atoms, benzhydyl, phenylsulfonyl-alkyl of 1 to 4 alkyl carbon atoms, furyl or furyl-alkenyl of 2 to 4 alkenyl carbon atoms, the aryl groups being optionally substituted by alkyl of 1 to 4 carbon atoms, by alkoxyl of 1 to 4 carbon atoms, by nitrogen, or cyano halogen atoms. $R_2$ is hydrogen, alkyl of 1 to 4 carbon atoms, alkenyl or alkinyl of 2 to 4 carbon atoms, halogen atoms or benzyl. $R_3$ is hydrogen, alkyl of 1 to 4 carbon atoms or phenyl. $R_4$ is hydrogen, alkyl of 1 to 4 carbon atoms, alkenyl of 2 to 4 carbon atoms, methoxy-methyl, halogen or benzyl and/or salts thereof.

These compounds are disclosed and more fully described in U.S. Pat. No. 4,185,106 and such compounds are available commercially from Hoechst Akitengeselfschaft under the trade name Octopirox.

(b) magnesium sulfate adducts of 2,2'-dithiobis(pyridine-1-oxide) of the formula

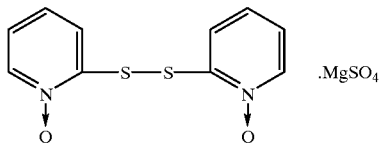

These compounds are available from Olin corporation under the trade name Omadine MDS.

It is preferred that an antidandruff agent be used in combination with a deposition polymer, where such a combination would result in improved deposition and retention of the antidandruff agent.

Additionally, the antidandruff agent can be a heavy metal magnesium or aluminium salts of 1-hydroxy-2-pyridinethione which has the following structural formula in tautomeric form, the sulfur being attached to the No. 2 position in the pyridine ring:

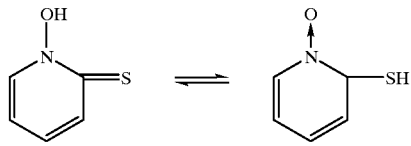

The metal salts represent substitution of the metal cation for the hydrogen of one of the tautomeric forms. Depending, of course, on the valence of the metal involved there may be more than one of the pyridinethione rings in the compound. Suitable heavy metals include zinc, tin, cadmium and zirconium.

Type (b)—The personal cleansing compositions of the invention can optionally contain a antidandruff agent which is a platelet pyridinethione salt crystal. When present, platelet pyridinethione salt crystals are predominantly flat platelets which have a mean sphericity less than about 0.65, preferably between about 0.20 and about 0.65 and a median size of at least about $2\mu$ diameter, expressed as the median equivalent diameter of a sphere of equal volume. It is preferred that the mean particle size be not greater than $15\mu$, measured on the same basis. The median diameters are on a mass basis with 50% of the mass of particles falling on either side of the value given.

The diameter of a sphere of equivalent volume for a particle can be determined by a varieties of sedimentation techniques which are based on Stokes' Law for the settling velocity of a partiyle in a fluid. Such techniques are described in Stockham, J. D. and Fochtman, E. G., *Particle Size Analysis*, Ann Arbour Science, 1978, incorporated herein by reference.

The sphericity of a particle is also described by Stockham and Fochtman at page 113 as $$\psi=(d_V/d_S)^2$$

where $d_V$ is the diameter of a sphere of equivalent volume, supra, and $d_S$ is the diameter of a sphere of equivalent area. In the present invention $$\text{the mean sphericity}=(\overline{\phantom{-}}d_V/\overline{\phantom{-}}d_S)^2 \text{ or}$$

surface areas of spheres having equivalent volume distribution divided by the actual surface area of particles as measured. See U.S. Pat. No. 4,379,753 to Bolich, Jr incorporated herein by reference.

Co-surfactants.

The surfactant system of the personal cleansing compositions of the present invention can comprise, in addition to the mid-chain branched surfactant, one or more detersive co-surfactants selected from the group consisting of anionic co-surfactant, nonionic co-surfactant, cationic co-surfactant, amphoteric co-surfactant, zwitterionic co-surfactants, and mixtures thereof. The personal cleansing composition in addition to the mid-chain branched surfactant, preferably comprise an anionic co-surfactant. The total amount of surfactant present in the personal cleansing composition (i.e., the mid-chain branched surfactant plus co-surfactant) is preferably at least about 5%, more preferably still at least about 8%, even more preferably at least about 10%, by weight. Furthermore, the total amount of surfactant (i.e., the mid-chain branched surfactant plus co-surfactant) present in the personal cleansing composition will be present at preferably less than about 45%, more preferably less than about 35%, even more preferably less than about 30%, even more preferably less than about 25%, even more preferably less than about 20%, most preferably less than about 15%, by weight.

Anionic Co-surfactant

The personal cleansing compositions preferably comprise an anionic co-surfactant, and preferably at concentrations of at least about 0.5%, more preferably, at least about 1%, even more preferably at least about 2%, even more preferably still at least about 5%, even more preferably still at least about 8%, most preferably at least about 10%, by weight. Furthermore, amount of anionic co-surfactant present in the personal cleansing composition will be present at preferably less than about 35%, more preferably less than about 30%, even more preferably less than about 25%, by weight of the composition. It is preferred that the total amount of anionic surfactant (i.e. anionic mid-chain branched plus anionic co-surfactant) present in the personal cleansing composition is preferably about 5% or greater, more preferrably 8% or greater, even more preferably about 10% or greater, even more preferably still about 12% or greater, by weight of the composition.

Anionic co-surfactants for use in the personal cleansing compositions include alkyl and alkyl ether sulfates. These materials have the respective formulae $ROSO_3M$ and $RO(C_2H_4O)_xSO_3M$, wherein R is alkyl or alkenyl of from about 8 to about 30 carbon atoms, x is 1 to 10, and M is a cation such as ammonium, alkanolamines, such as triethanolamine, monovalent metals, such as sodium and potassium, and polyvalent metal cations, such as magnesium, and calcium. The cation M, of the anionic co-surfactant should be chosen such that the anionic co-surfactant component is water soluble. Solubility will depend upon the particular anionic co-surfactants and cations chosen.

Preferably, R has from about 12 to about 18 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil or tallow, or can be synthetic. Lauryl alcohol and straight chain alcohols derived from coconut oil are preferred herein. Such alcohols are reacted with between about 0 and about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the personal cleansing compositions of the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic co-surfactants are the water-soluble salts of organic, sulfiric acid reaction products of the general formula [$R_1$—$SO_3$—M] where $R_1$ is selected from the group consisting of a straight or branched chain, saturated aliphatic hydrocarbon radical having from about 8 to about 24, preferably about 10 to about 18, carbon atoms; and M is a cation, as previously described, subject to the same limitations regarding polyvalent metal cations as previously discussed. Examples of such co-surfactants are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10-18}$ n-paraffins.

Still other suitable anionic co-surfactants are the reaction products of fatty acids esterified with isethionic acid and neutralized with sodium hydroxide where,

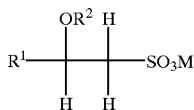

where $R^1$ is a straight chain alkyl group having from about 6 to about 20 carbon atoms, $R^2$ is a lower alkyl group having from about 1 (preferred) to about 3 carbon atoms, and M is a water-soluble cation as hereinbefore described.

Many other anionic co-surfactants suitable for use in the personal cleansing compositions are described in McCutcheon's, Emulsifiers and Detergents, 1989 Annual, published by M. C. Publishing Co., and in U.S. Pat. No. 3,929,678, which descriptions are incorporated herein by reference.

Preferred anionic co-suifactants for use in the personal cleansing compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauwyl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric and Zwitterionic Co-surfactants

The detersive co-surfactant of the personal cleansing compositions may comprise an amphoteric and/or zwitterionic co-surfactant. Concentrations of such co-surfactants will generally range from about 0.5% to about 20%, preferably from about 1% to about 10%, by weight of the personal cleansing compositions.

Amphoteric co-surfactants for use in the personal cleansing compositions include the derivatives of aliphatic secondary and tertiary amines in which the aliphatic radical is straight or branched and one of the aliphatic substituents contains from about 8 to about 18 carbon atoms and one contains an anionic water solubilizing group, e.g., carboxy, sulfonate, sulfate, phosphate, or phosphonate.

Zwitterionic co-surfactants for use in the personal cleansing compositions include the derivatives of aliphatic quaternary ammonium, phosphonium, and sulfonium compounds, in which the aliphatic radicals are straight or branched, and wherein one of the aliphatic substituents contains from about 8 to about 18 carbon atoms and one contains an anionic group, e.g., carboxy, sulfonate, sulfate, phosphate, or phosphonate. A general formula for these compounds is:

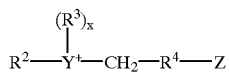

where $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of amphoteric and zwitterionic co-surfactants also include sultaines and amidosultaines. Sultaines and amidosultaines can be used as foam enhancing co-surfactants that are mild to the eye in partial replacement of anionic co-surfactants. Sultaines, including amidosultaines, include for example, cocodimethylpropylsultaine, stearyldimethylpropylsultaine, lauryl-bis-(2-hydroxyethyl) propylsultaine and the like; and the amidosultaines such as cocoamidodimethylpropylsultaine, stearylamidododimethylpropylsultaine, laurylamidobis-(2-hydroxyethyl) propylsultaine, and the like. Preferred are amidohydroxysultaines such as the $C_{12}$–$C_{18}$ hydrocarbyl amidopropyl hydroxysultaines, especially $C_{12}$–$C_{14}$ hydrocarbyl amido propyl hydroxysultaines, e.g., laurylamidopropyl hydroxysultaine and cocamidopropyl hydroxysultaine. Other sultaines are described in U.S. Pat. No. 3,950,417, which descriptions are incorporated herein by reference.

Other suitable amphoteric co-surfactants are the aminoalkanoates of the formula R—NH($CH_2$)$_n$COOM, the iminodiaLkanoates of the formula R—N[(CH$_2$)$_m$COOM]$_2$ and mixtures thereof; wherein n and m are numbers from 1 to 4, R is C$_8$–C$_{22}$ alkyl or alkenyl, and M is hydrogen, alkali metal, alline earth metal, ammonium or alkanolammonium.

Examples of suitable aminoalkanoates include n-alkylamino-propionates and n-alkyliminodipropionates, specific examples of which include N-lauryl-beta-amino propionic acid or salts thereof, and N-lauryl-beta-iminodipropionic acid or salts thereof, and mixtures thereof.

Other suitable amphoteric co-surfactants include those represented by the formula:

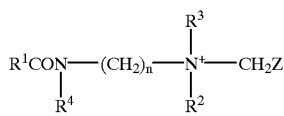

wherein R$^1$ is C$_8$–C$_{22}$ alkyl or alkenyl, preferably C$_{12}$–C$_{16}$, R$^2$ is hydrogen or CH$_2$CO$_2$M, R$^3$ is CH$_2$CH$_2$OH or CH$_2$CH$_2$OCH$_2$CH$_2$COOM, R$^4$ is hydrogen, CH$_2$CH$_2$OH, or CH$_2$CH$_2$OCH$_2$CH$_2$COOM, Z is CO$_2$M or CH$_2$CO$_2$M, n is 2 or 3, preferably 2, M is hydrogen or a cation, such as alkali metal (e.g., lithium, sodium, potassium), alkaline earth metal (beryllium, magnesium, calcium, strontium, barium), or ammonium. This type of co-surfactant is sometimes classified as an imidazoline-type amphoteric co-surfactant, although it should be recognized that it does not necessarily have to be derived, directly or indirectly, through an imidazoline intermediate.

Suitable materials of this type are marketed under the trade name MIRANOL and are understood to comprise a complex mixture of species, and can exist in protonated and non-protonated species depending upon pH with respect to species that can have a hydrogen at R$^2$. All such variations and species are meant to be encompassed by the above formula.

Examples of co-surfactants of the above formula are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Commercial amphoteric co-surfactants include those sold under the trade names MIRANOL C2M CONC. N.P., MIRANOL C2M CONC. O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTERIC MS-2 (Scher Chemicals).

Betaine co-surfactants (zwitterionic) suitable for use in the personal cleansing compositions are those represented by the formula:

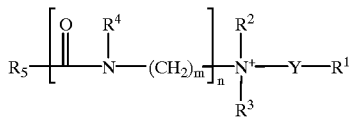

wherein:

R$_1$ is a member selected from the group consisting of

COOM and CH(OH)—CH$_2$SO$_3$M

R$_2$ is lower alkyl or hydroxyalkyl;

R$_3$ is lower alkyl or hydroxyalkyl;

R$_4$ is a member selected from the group consisting of hydrogen and lower alkyl;

R$_5$ is higher alkyl or alkenyl;

Y is lower alkyl, preferably methyl;

m is an integer from 2 to 7, preferably from 2 to 3;

n is the integer 1 or 0;

M is hydrogen or a cation, as previously described, such as an alkali metal, alkaline earth metal, or ammonium.

The term "lower alkyl" or "hydroxyalkyl" means straight or branch chained, saturated, aliphatic hydrocarbon radicals and substituted hydrocarbon radicals having from one to about three carbon atoms such as, for example, methyl, ethyl, propyl, isopropyl, hydroxypropyl, hydroxyethyl, and the like. The term "higher alkyl or alkenyl" means straight or branch chained saturated (i.e., "higher alkyl") and unsaturated (i.e., "higher alkenyl") aliphatic hydrocarbon radicals having from about eight to about 20 carbon atoms such as, for example, lauryl, cetyl, stearyl, oleyl, and the like. It should be understood that the term "higher alkyl or alkenyl" includes mixtures of radicals which may contain one or more intermediate linkages such as ether or polyether linkages or non-functional substitutents such as hydroxyl or halogen radicals wherein the radical remains of hydrophobic character.

Examples of co-surfactant betaines of the above formula wherein n is zero which are usefull herein include the alkylbetaines such as cocodimethylcarboxymethylbetaine, lauryldimethylcarboxymethylbetaine, lauryl dimethyl-alpha-carboxyethylbetaine, cetyldimethylcarboxymethylbetaine, lauryl-bis-(2-hydroxyethyl)carboxymethylbetaine, stearyl-bis-(2-hydroxypropyl)carboxymethylbetaine, oleyldimethyl-gamma-carboxypropylbetaine, lauryl-bis-(2-hydroxypropyl)alpha-carboxyethylbetaine, etc. The sulfobetaines may be represented by cocodimethylsulfopropylbetaine, stearyldimethylsulfopropylbetaine, lauryl-bis-(2-hydroxyethyl)sulfopropylbetaine, and the like.

Specific examples of amido betaines and amidosulfo betaines useful in the personal cleansing compositions include the amidocarboxybetaines, such as cocoamidodimethylcarboxymethylbetaine, laurylamidodimethylcarboxymethylbetaine, cetylamidodimethylcarboxymethylbetaine, laurylamido-bis-(2-hydroxyethyl)carboxymethylbetaine, cocoamido-bis-(2-hydroxyethyl)-carboxymethylbetaine, etc. The amido sulfobetaines may be represented by cocoamidodimethylsulfopropylbetaine, stearylamidodimethylsulfopropylbetaine, laurylamido-bis-(2-hydroxyethyl)-sulfopropylbetaine, and the like.

Nonionic Co-surfactant

The personal cleansing compositions of the present invention may comprise a nonionic co-surfactant as the detersive co-surfactant component therein. Nonionic co-surfactants include those compounds produced by condensation of alkylene oxide groups (hydrophilic in nature) with an organic hydrophobic compound, which may be aliphatic or alkyl aromatic in nature.

Concentrations of such co-surfactants will generally range from about 0.01% to about 20%, preferably from about 1% to about 10%, by weight of the personal cleansing compositions.

Preferred nonionic co-surfactants for use in the personal cleansing compositions include the following:

(1) polyethylene oxide condensates of alkyl phenols, e.g., the condensation products of alkyl phenols having an allyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol;

(2) those derived from the condensation of ethylene oxide with the product resulting from the reaction of propylene oxide and ethylene diamine products;

(3) condensation products of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms;

(4) long chain tertiary amine oxides of the formula $[R^1R^2R^3N \rightarrow O]$ where $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals;

(5) long chain tertiary phosphine oxides of the formula $[RR'R''P \rightarrow O]$ where R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R'' are each alkyl or monohydroxyalkyl groups containing from about 1 to about 3 carbon atoms;

(6) long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety;

(7) aillyl polysaccharide (APS) co-surfactants (e.g. alkyl polyglycosides), examples of which are described in U.S. Pat. No. 4,565,647, which description is incorporated herein by reference, and which discloses APS co-surfactants having a hydrophobic group with about 6 to about 30 carbon atoms and polysaccharide (e.g., polyglycoside) as the hydrophilic group; optionally, there can be a polyalkylene-xide group joining the hydrophobic and hydrophilic moieties; and the alkyl group (i.e., the hydrophobic moiety) can be saturated or unsaturated, branched or unbranched, and unsubstituted or substituted (e.g., with hydroxy or cyclic rings); and (8) polyethylene glycol (PEG) glyceryl fatty esters, such as those of the formula $R(O)OCH^2CH(OH)CH^2(OCH^2CH^2)_nOH$ wherein n is from about 5 to about 200, preferably from about 20 to about 100, and R is an aliphatic hydrocarbyl having from about 8 to about 20 carbon atoms.

Cationic Co-surfactants

Optional cationic co-surfactants for use as conditioning agents in the personal cleansing compositions will typically contain quaternary nitrogen moieties. Examples of suitable cationic co-surfactants are described in following documents, all of which are incorporated by reference herein in their entirety: M.C. Publishing Co., McCutcheon's, Detergents & Emulsifiers, (North American edition 1979); Schwartz, et al., Surface Active Agents, Their Chemistry and Technology, New York: Interscience Publishers, 1949; U.S. Pat. No. 3,155,591; U.S. Pat. No. 3,929,678; U.S. Pat. No. 3,959,461 and U.S. Pat. No. 4,387,090.

Concentrations of such co-surfactants will generally range from about 0.01% to about 20%, preferably from about 1% to about 10%, by weight of the personal cleansing compositions.

Examples of suitable cationic co-surfactants are those corresponding to the general formula:

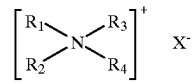

wherein $R_1$, $R_2$, $R_3$, and $R_4$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate nitrate, sulfate, and alkylsulfate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R_1$, $R_2$, $R_3$, and $R_4$ are independently selected from C1 to about C22 alkyl. Especially preferred are cationic materials containing two long alkyl chains and two short alkyl chains or those containing one long alkyl chain and three short alkyl chains. The long alkyl chains in the compounds described in the previous sentence have from about 12 to about 22 carbon atoms, preferably from about 16 to about 22 carbon atoms, and the short alkyl chains in the compounds described in the previous sentence have from 1 to about 3 carbon atoms, preferably from 1 to about 2 carbon atoms.

Aqueous Liquid Carrier

The personal cleansing compositions herein furter contain from about 50% to 99.899%, preferably from about 60% to about 95%, more preferably from about 70% to about 85%, by weight of an aqueous liquid carrier in which the other essential and optional compositions components are dissolved, dispersed or suspended.

One essential component of the aqueous liquid carrier is, of course, water. The aqueous liquid carrier, however, may contain other materials which are liquid, or which dissolve in the liquid carrier, at room temperature and which may also serve some other function besides that of a simple filler. Such materials can include, for example, hydrotropes and co-solvents.

a) Hydrotropes

The aqueous liquid carrier may comprise one or more materials which are hydrotropes. Hydrotropes suitable for use in the compositions herein include the $C_1$–$C_3$ alkyl aryl sulfonates, $C_6$–$C_{12}$ alkanols, $C_1$–$C_6$ carboxylic sulfates and sulfonates, urea, $C_1$–$C_6$ hydrocarboxylates, $C_1$–$C_4$ carboxylates, $C_2$–$C_4$ organic diacids and mixtures of these hydrotrope materials.

Suitable $C_1$–$C_3$ alkyl aryl sulfonates include sodium, potassium, calcium and ammonium xylene sulfonates; sodium, potassium, calcium and ammonium toluene sulfonates; sodium, potassium, calcium and ammonium cumene sulfonates; and sodium, potassium, calcium and ammonium substituted or unsubstituted naphthalene sulfonates and mixtures thereof.

Suitable $C_1$–$C_8$ carboxylic sulfate or sulfonate salts are any water soluble salts or organic compounds comprising 1 to 8 carbon atoms (exclusive of substituent groups), which are substituted with sulfate or sulfonate and have at least one carboxylic group. The substituted organic compound may be cyclic, acylic or aromatic, i.e. benzene derivatives. Preferred alkyl compounds have from 1 to 4 carbon atoms substituted with sulfate or sulfonate and have from 1 to 2 carboxylic groups. Examples of this type of hydrotrope include sulfosuccinate salts, sulfophthalic salts, sulfoacetic salts, m-sulfobenzoic acid salts and diester sulfosuccinates, preferably the sodium or potassium salts as disclosed in U.S. Pat. No. 3,915,903.

Suitable $C_1$–$C_4$ hydrocarboxylates and $C_1$–$C_4$ carboxylates for use herein include acetates and propionates and citrates. Suitable $C_2$–$C_4$ diacids for use herein include succinic, glutaric and adipic acids.

Other compounds which deliver hydrotropic effects suitable for use herein as a hydrotrope include $C_6$–$C_{12}$ alkanols and urea.

Preferred hydrotropes for use herein are sodium, potassium, calcium and ammonium cumene sulfonate; sodium, potassium, calcium and ammonium xylene sulfonate; sodium, potassium, calcium and ammonium toluene sulfonate and mixtures thereof Most preferred are sodium cumene sulfonate and sodium xylene sulfonate and mixtures thereof. These preferred hydrotrope materials can be present in the composition to the extent of from about 0.1% to 8% by weight.

b) Co-Solvents

A variety of water-miscible liquids such as lower alkanols, diols, other polyols, ethers, amines, and the like may be used as part of the aqueous liquid carrier. Particularly preferred are the $C_1$–$C_4$ alkanols. Such co-solvents can be present in the compositions herein to the extent of up to about 8%. These co-solvents are different to the solvents used in combination with styling polymers as the co-solvents dissolved, dispersed any or all of the components of the personal cleansing compositions. Whereas, the solvent is concerned with only dispersing, and preferably dissolving, the styling polymer.

Optional Components

The personal cleansing compositions of the present invention may further comprise one or more optional components known for use in shampoo, conditioning and other personal cleansing compositions, provided that the optional components are physically and chemically compatible with the essential component described herein, or do not otherwise unduly impair product stability, aesthetics or performance. Concentrations of such optional components typically range from about 0.001% to about 30% by weight of the personal cleansing compositions, when present.

Optional components include anti static agents, dyes, diluents, emollient oils (such as polyisobutylene, mineral oil, petrolatum and isocetyl stearyl stearate), pearlescent aids, foam boosters, pediculocides, pH adjusting agents, perfumes, preservatives, proteins, antioxidants; chelators and sequestrants; and aesthetic components such as fragrances, colorings, essential oils, skin sensates, astringents, skin soothing agents, skin healing agents and the like, nonlimiting examples of these aesthetic components include panthenol and derivatives (e.g. ethyl panthenol), pantothenic acid and its derivatives, clove oil, menthol, camphor, eucalyptus oil, eugenol, menthyl lactate, witch hazel distillate, allantoin, bisabalol, dipotassium glycyrrhizinate and the like, sunscreens, thickeners, vitamins and derivatives thereof (e.g., ascorbic acid, vitamin E, tocopheryl acetate, retinoic acid, retinol, retinoids, and the like), and viscosity adjusting agents. This list of optional components is not meant to be exclusive, and other optional components can be used.

EXAMPLES

The following examples illustrate the present invention. It will be appreciated that other modifications of the present invention within the skill of those in the personal cleansing formulation art can be undertaken without departing from the spirit and scope of this invention. All of the formulations exemplified hereinafter are prepared via conventional formulation and mixing methods unless specific methods are given.

All parts, percentages, and ratios herein are by weight unless otherwise specified. Some components may come from suppliers as dilute solutions. The levels given reflect the weight percent of the active material, unless otherwise specified. The excluded diluents and other materials are included as "Minors".

Example VIII

| Components | Weight % | |
| --- | --- | --- |
| | A | B |
| TEA C12–C14 Alkyl Sulfate | 10.00 | — |
| NH4 C12–C14 Alkyl (Ethoxy)3 Sulfate | — | 7.90 |
| Mid-chain Branched surfactant according to example IV | 5 | 7.90 |
| Cocamide MEA | 3.00 | 1.50 |
| Dimethicone DC-200* | 3.00 | 3.00 |
| Ethylene Glycol Distearate | 1.50 | 1.50 |
| Citric acid | 0.60 | 0.60 |
| Trisodium citrate | 0.30 | — |
| Q.S. Color, preservative, Perfume and water | q.s. to 100% | q.s. to 100% |

Example IX

The following are personal cleansing compositions of the present invention.

| Component | Weight % | |
| --- | --- | --- |
| | C | D |
| Ammonium Lauryl Sulfate | 2.5 | 8.5 |
| Ammonium Laureth (3) Sulfate | 8.5 | 8.5 |
| JAGUAR C-17[1] | 0.5 | 0.5 |
| BAS[2] | 6.0 | 2.0 |
| Coconut Monoethanol Amide | 1.0 | 1.0 |
| Ethylene Glycol Distearate | 2.0 | 2.0 |
| Isocetyl Stearoyl Stearate | 1.0 | 1.0 |
| Tricetyl Methyl Ammonium Chloride | 0.5 | 0.5 |
| Polydimethylsiloxane[3] | 2.0 | 2.0 |
| Cetyl Alcohol | 0.4 | 0.4 |
| Stearyl Alcohol | 0.2 | 0.2 |
| Perfume | 1.0 | 1.0 |

| Component | Weight % | |
|---|---|---|
| | C | D |
| Color Solution | 0.6 | 0.6 |
| Preservative | 0.4 | 0.4 |
| Water and Minors | q.s to 100% | q.s to 100% |

[1]Tradename for guar hydroxypropyltrimonium chloride, a cationic polymer available from Rhone-Poulenc (Cranbury, NJ, USA).
[2]The Mid-Chain Branched surfactants according to example III.
[3]A 40/60 weight ratio blend of polydimethylsiloxane gum (GE SE 76, available from General Electric Co., Silicone Products Div., Waterford, NY, USA) and polydimethylsiloxane fluid (about 350 centistokes).

The composition can provide excellent in-use hair cleaning and conditioning. As an alternative, the JAGUAR C-17 can be replaced with LUVIQUAT FC 370 (see Example III, footnote 1).

Example X

The following are personal cleansing compositions of the present invention.

| Component | Weight % | |
|---|---|---|
| | E | F |
| Ammonium Lauryl Sulfate | 4.2 | 2.2 |
| Ammonium Laureth (3) Sulfate | 9.2 | 9.2 |
| POLYMER LR 400[1] | 1.0 | 1.0 |
| BAS[2] | 4.0 | 6.0 |
| Coconut Monoethanol Amide | 1.0 | 1.0 |
| Ethylene Glycol Distearate | 2.0 | 2.0 |
| Light Mineral Oil | 1.0 | 1.0 |
| Tricetyl Methyl Ammonium Chloride | 0.5 | 0.5 |
| Polydimethylsiloxane[2] | 1.5 | 1.5 |
| Cetyl Alcohol | 0.4 | 0.4 |
| Stearyl Alcohol | 0.2 | 0.2 |
| Perfume | 1.2 | 1.2 |
| Color Solution | 0.6 | 0.6 |
| Preservative | 0.4 | 0.4 |
| Water and Minors | q.s. to 100% | q.s. to 100% |

[1]Cellulose, 2-[2-hydroxy-3-(trimethyl ammonio)propoxy] ethyl ether, chloride, a cationic polymer available from Amerchol Corp. (Edison, NJ, USA).
[2]The Mid-Chain Branched surfactants according to example V.
[3]A 40/60 weight ratio blend of polydimethylsiloxane gum (GE SE 76, available from General Electric Co., Silicone Products Div., Waterford, NY, USA) and polydimethylsiloxane fluid (about 350 centistokes).

The composition can provide excellent in-use hair cleaning and conditioning

Example XI

The following is an example of a personal cleansing composition of the present invention wherein the cationic polymer and anionic surfactant component form a complex coacervate phase.

| Component | Weight % G |
|---|---|
| Ammonium Laureth (3) Sulfate | 4.0 |
| LUVIQUAT FC 370[1] | 0.5 |
| BAS[2] | 13.5 |
| Coconut Monoethanol Amide | 1.0 |
| Ethylene Glycol Distearate | 2.0 |
| Light Mineral Oil | 0.5 |
| Tricetyl Methyl Ammonium Chloride | 0.5 |
| Polydimethylsiloxane[2] | 3.0 |
| Cetyl Alcohol | 0.4 |
| Stearyl Alcohol | 0.2 |
| Perfume | 1.0 |
| Color Solution | 0.6 |
| Preservative | 0.4 |
| Water and Minors | 73.8 |

[1]Tradename of BASF Wyandotte Corporation (Parsippany, NJ, USA) for copolymer of vinyl pyrrolidone and methyl vinyl imidazolium chloride.
[2]The Mid-Chain Branched surfactants according to example II.
[3]A 40/60 weight ratio blend of polydimethylsiloxane gum (GE SE 76, available from General Electric Co., Silicone Products Div., Waterford, NY, USA) and polydimethylsiloxane fluid (about 350 centistokes).

The composition can provide excellent in-use hair cleaning and conditioning. As an alternative, the LUVIQUAT FC 370 can be replaced with JAGUAR C-17 (see Example I, footnote 1).

Example XII

The following is an example of a personal cleansing composition of the present invention.

| Component | Weight % H |
|---|---|
| Cocoamidopropyl Betaine | 4.0 |
| Ammonium Laureth (3) Sulfate | 8.0 |
| Coconut Monoethanol Amide | 2.0 |
| Ethylene Glycol Distearate | 2.0 |
| Polymer JR-125[1] | 1.0 |
| BAS[2] | 4.0 |
| Isopropyl Isostearate | 1.0 |
| Tricetyl Methyl Ammonium Chloride | 0.5 |
| Polydimethylsiloxane[3] | 1.5 |
| Cetyl Alcohol | 0.4 |
| Stearyl Alcohol | 0.2 |
| Perfume | 1.0 |
| Color Solution | 0.6 |
| Preservative | 0.4 |
| Water and Minors | q.s. to 100% |

[1]Cellulose, 2-[2-hydroxy-3-(trimethyl ammonio)propoxy] ethyl ether, chloride, available from Amerchol Corp. (Edison, NJ, USA).
[2]The Mid-Chain Branched surfactants according to example I.
[3]VISCASIL 12,500 cS silicone fluid, available from General Electric (Waterford, NY, USA).

Example XIII

The following are personal cleansing compositions of the present invention.

| Component | Weight % | |
|---|---|---|
| | I | J |
| Ammonium Lauryl Sulfate | 8.5 | 2.0 |
| Ammonium Laureth (3) Sulfate | 4.0 | 4.0 |
| Polymer LM-200[1] | 1.0 | 1.0 |
| BAS[2] | 5.0 | 11.5 |
| Light Mineral Oil | 1.0 | 1.0 |
| Coconut Monoethanol Amide | 1.0 | 1.0 |
| Ethylene Glycol Distearate | 2.0 | 2.0 |

-continued

| Component | Weight % | |
|---|---|---|
| | I | J |
| Tricetyl Methyl Ammonium Chloride | 0.5 | 0.5 |
| Polydimethylsiloxane[3] | 3.0 | 3.0 |
| Cetyl Alcohol | 0.4 | 0.4 |
| Stearyl Alcohol | 0.2 | 0.2 |
| Perfume | 1.0 | 1.0 |
| Color Solution | 0.6 | 0.6 |
| Preservative | 0.4 | 0.4 |
| Water and Minors | q.s. to 100% | q.s. to 100% |

[1]Polyquaternium 24, a polymeric quaternary ammonium salt of hydroxyethyl cellulose reacted with lauryl dimethyl ammonium-substituted epoxide, available from Amerchol Corp. (Edison, NJ, USA).
[2]The Mid-Chain Branched surfactants according to example VII.
[3]A 40/60 weight ratio blend of polydimethylsiloxane gum (GE SE 76, available from General Electric Co., Silicone Products Div., Waterford, NY, USA) and polydimethylsiloxane fluid (about 350 centistokes).

Example XIV

The following is a personal cleansing composition of the present invention wherein the lo cationic polymer and anionic surfactant component form a complex coacervate phase.

| Component | Weight % K |
|---|---|
| Ammonium Laureth (3) Sulfate | 8.5 |
| GAFQUAT 755N[1] | 0.5 |
| FLEXAN 130[4] | 0.5 |
| Coconut Monoethanol Amide | 1.0 |
| Ethylene Glycol Distearate | 2.0 |
| BAS[2] | 8.5 |
| Isocetyl Stearoyl Stearate | 1.0 |
| Tricetyl Methyl Ammonium Chloride | 0.5 |
| Polydimethylsiloxane[3] | 2.0 |
| Cetyl Alcohol | 0.4 |
| Stearyl Alcohol | 0.2 |
| Perfume | 1.0 |
| Color Solution | 0.6 |
| Preservative | 0.4 |
| Water and Minors | q.s. to 100% |

[1]Copolymer of 1-vinyl-2-pyrrolidone and dimethylaminoethylmethacrylate, available from GAF Corp., Wayne, NJ, USA.
[2]The Mid-Chain Branched surfactants according to example VI.
[3]VISCASIL, 600,000 cS, from General Electric, Waterford, NY, USA.
[4]Sodium polystyrene sulfonate, an anionic polymer available from National Starch and Chemical Corp., Bridgewater, NJ, USA.

The composition can provide excellent in-use hair cleaning and conditioning. The example compositions hereof can be made by preparing a premix of the entire amount of silicone conditioning agent to be incorporated into the personal cleansing, along with sufficient ammonium sulfate and cetyl and stearyl alcohol such that the premix comprises about 30% silicone conditioning agent, about 69% surfactant, and about 1% of the alcohols. The premix ingredients are heated and stirred at 72° C. for about 10 minutes and the premix is then conventionally mixed with the remaining hol: (72° C.) ingredients. The composition is then pumped through a high shear mixer and cooled.

Example XV

The following examples, (L to Z), further describe and demonstrate embodiments within the scope of the present invention. The examples are given solely for the purpose of illustration and are not to be construed as limitations of the present invention, as many variations thereof are possible without departing from the spirit and scope of the invention. These exemplified embodiments of the shampoo compositions of the present invention provide cleansing of hair and improved hair conditioning performance. Ingredients are hereinafter identified by chemical, trade, or CTFA name.

Preparation The shampoo compositions of the present invention can be prepared by using conventional mixing and formulating techniques. The shampoo compositions illustrated hereinafter in Examples L to Z are prepared in the following manner.

About one-third to all of the total sulfate surfactant (added as a 25% solution) is added to a jacketed mix tank and heated to about 74° C. with slow agitation to form a surfactant solution. Cocamide MEA and fatty alcohol, as applicable, are added to the tank and allowed to disperse. Ethylene glycol distearate (EGDS), as applicable, is then added to the mixing vessel, and melted. After the EGDS is well dispersed (usually about 5 to 20 minutes) polyethylene glycol and the preservative, if used are added and mixed into the surfactant solution. This mixture is passed through a heat exchanger where it is cooled to about 35° C. and collected in a finishing tank. As a result of this cooling step, the ethylene glycol distearate crystallizes to form a crystalline network in the product. The remainder of the surfactant and other ingredients including the silicone emulsions are added to the finishing tank with ample agitation to insure a homogeneous mixture. A sufficient amount of the silicone emulsions are added to provide the desired level of dimethicone in the final product. Water dispersible polymers are typically dispersed in water as a 1% to 10% solution before addition to the final mix. Once all ingredients have been added, ammonium xylene sulfonate or additional sodium chloride can be added to the mixture to thin or thicken respectively to achieve a desired product viscosity. Preferred viscosities range from about 2500 to about 9000 cS at 25° C. (as measured by a Wells-Brookfield cone and plate viscometer at 15/s).

| Component | L | M | N | O | P |
|---|---|---|---|---|---|
| Ammonium BAS[1] | 2 | 4 | 4 | 5 | 4 |
| Ammonium BAES[2] | 8 | 6 | 12 | 10 | 12 |
| Cocamidopropylbetaine | 0 | 0 | 2.5 | 0 | 1 |
| Jaguar C17[8] | 0.05 | 0.05 | 0.05 | 0.30 | 0.15 |
| Cocamide MEA | 0.5 | 0.5 | 0.80 | 0.80 | 0 |
| Cetyl Alcohol | 0 | 0 | 0.42 | 0.42 | 0.42 |
| Stearyl Alcohol | 0 | 0 | 0.18 | 0.18 | 0.18 |
| Ethylene Glycol Distearate | 1.50 | 1.50 | 1.50 | 1.50 | 1.50 |
| EP Silicone[4] | 3.0 | 2.5 | 3.0 | 2.0 | 3.0 |
| Perfume Solution | 0.70 | 0.70 | 0.70 | 0.70 | 0.70 |
| DMDM Hydantoin | 0.37 | 0.37 | 0.37 | 0.37 | 0.37 |
| Color Solution (ppm) | 64 | 64 | 64 | 64 | 64 |
| Water and Minors | -----q.s. to 100%----- | | | | |

| Component | Q | R | S | T | U |
|---|---|---|---|---|---|
| Ammonium BAES[3] | 9.00 | 9.00 | 14.0 | 14.85 | 12.50 |
| Cocamidopropylbetaine | 1.70 | 1.70 | 2.70 | 1.85 | 4.20 |
| Polyquaternium-10[6] | 0.05 | 0.02 | 0.15 | 0.15 | 0.15 |
| Cocamide MEA | 0.80 | 0.80 | 0.80 | 0.80 | 0 |
| Cetyl Alcohol | 0 | 0 | 0.42 | 0.42 | 0.42 |
| Stearyl Alcohol | 0 | 0 | 0.18 | 0.18 | 0.18 |
| Ethylene Glycol Distearate | 1.50 | 1.50 | 1.50 | 1.50 | 1.50 |
| EP Silicone[7] | 3.0 | 2.5 | 3.0 | 2.0 | 3.0 |
| Perfume Solution | 0.70 | 0.70 | 0.70 | 0.70 | 0.70 |
| DMDM Hydantoin | 0.37 | 0.37 | 0.37 | 0.37 | 0.37 |
| Color Solution (ppm) | 64 | 64 | 64 | 64 | 64 |
| Water and Minors | -----q.s. to 100%----- | | | | |

-continued

| Component | V | W | X | Y | Z |
|---|---|---|---|---|---|
| Ammonium BAES[1] | 14.0 | 14.00 | 14.00 | 9.00 | 9.00 |
| Cocamidopropylbetaine | 2.70 | 2.70 | 2.70 | 1.70 | 1.70 |
| Polyquaternium-10[9] | 0. | 0.15 | 0.15 | 0.05 | 0.02 |
| Cocamide MEA | 0.80 | 0.80 | 0 | 0.80 | 0.80 |
| Cetyl Alcohol | 0 | 0.42 | 0 | 0 | 0 |
| Stearyl Alcohol | 0 | 0.18 | 0 | 0 | 0 |
| Ethylene Glycol Distearate | 0 | 0 | 0 | 1.50 | 1.50 |
| Carbopol 981[5] | 0.50 | 0.50 | 0.50 | 0 | 0 |
| EP Silicone[4] | 3.0 | 2.5 | 3.0 | 2.0 | 3.0 |
| Perfume Solution | 0.70 | 0.70 | 0.70 | 0.70 | 0.70 |
| DMDM Hydantoin | 0.37 | 0.37 | 0.37 | 0.37 | 0.37 |
| Color Solution (ppm) | 64 | 64 | 64 | 64 | 64 |
| Water and Minors | -----q.s. to 100%----- | | | | |

[1]The Mid-Chain Branched surfactant according to example V
[2]The Mid-Chain Branched surfactant according to example I.
[3]The Mid-Chain Branched surfactant according to example VI.
[4]EP Silicone is an experimental emulsion polymerized polydimethyl siloxane of about 97,000 csk with particle size of approximately 300 nm made via linear feedstock available from Dow Corning (2-1520; 13556-34).
[5]Carbopol 981 is a crosslinked polyacrylate available from B. F. Goodrich.
[6]Polyquaternium-10 is JR30M, a cationic cellulose derived polymer available from Amerchol.
[7]EP Silicone is an experimental emulsion polymerized polydimethyl siloxane of about 335,000 csk with particle size of approximately 500 nm made via linear feedstock available from Dow Corning (2-1520; PE106004).
[8]Jaguar C17 is a cationic polymer available from Rhone-Poulenc
[9]Polyquaternium-10 is JR400, a cationic cellulose derived polymer available from Amerchol.

Example XVI

A shampoo having the following formula is prepared

| Component | % weight |
|---|---|
| | AA |
| BAS* | 17 |
| Zinc Pyridinethione** | 2.0 |
| Coconut Monoethanolamide | 3.0 |
| Ethylene Glycol Distereate | 5.0 |
| Sodium Citrate | 0.5 |
| Citric Acid | 0.2 |
| Color solution | 0.1 |
| Perfume | 0.5 |
| Water | q.s. to 100.00% |

*The Mid-Chain Branched surfactant according to example III.
**The Zinc pyridinethione salt crystals prepared according to the method described in U.S. Pat. No. 4,379,753 to Bolich.

| Component | % weight |
|---|---|
| | BB |
| Triethanolamine alkyl sulfate | 10% |
| BAS* | 9 |
| Zinc Pyridinethione** | 2.0 |
| Coconut Monoethanolamide | 2.0 |
| Triethanolamine | 3.0 |
| Magnesium/Aluminium Silicate | 0.5 |
| Hydroxy Methyl Cellulose | 0.6 |
| Color solution | 0.1 |
| Perfume | 0.3 |
| Water | q.s. to 100.00% |

*The Mid-Chain Branched surfactant according to example IV.
**The Zinc pyridinethione salt crystals prepared according to the method described in U.S. Pat. No. 4,379,753 to Bolich.

| Component | % weight |
|---|---|
| | CC |
| Sodium Alkyl Glyceryl Sulfonate | 5% |
| BAS* | 15 |
| Zinc Pyridinethione** | 2.0 |
| Sodium Chloride | 5.0 |
| Sodium N-Lauryl Sarcosinate | 12.0 |
| N-Cocoyl Sarcosine Acid | 1.0 |
| Lauric Diethanolamide | 2.0 |
| Color solution | 0.12 |
| Perfume | 0.5 |
| Water | q.s. to 100.00% |

*The Mid-Chain Branched surfactant according to example V.
**The Zinc pyridinethione salt crystals prepared according to the method described in U.S. Pat. No. 4,379,753 to Bolich.

Example XVII

The compositions illustrated in Example XVII (DD to TT), illustrate specific embodiments of the shampoo compositions of the present invention, but are not intended to be limiting thereof Other modifications can be undertaken by the skilled artisan without departing from the spirit and scope of this invention. These exemplified embodiments of the shampoo compositions of the present invention provide excellent cleansing of hair and dandruff control.

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components.

| Component | DD | EE | FF | GG | HH |
|---|---|---|---|---|---|
| Ammonium Laureth Sulfate | 15.00 | 15.00 | 15.00 | 15.00 | 7.50 |
| BAS* | 5.00 | 5.00 | 5.00 | 5.00 | 2.50 |
| Sodium Lauroyl Sarcosinate | 1.50 | 1.50 | 1.50 | 1.50 | 0.75 |
| Ethylene Glycol Distearate | 1.50 | 1.50 | 1.50 | 1.50 | 1.50 |
| Zinc Pyrithione | 1.00 | 1.00 | 1.00 | — | 1.00 |
| Selenium Disulfide | — | — | — | 1.00 | — |
| Jaguar C17S | 0.10 | 0.05 | 0.50 | 0.10 | 0.10 |
| Fragrance | q.s. | q.s. | q.s. | q.s. | q.s. |
| Color | q.s. | q.s. | q.s. | q.s. | q.s. |
| pH adjustment (Mono/Di sodium Phosphate) | q.s. | q.s. | q.s. | q.s. | q.s. |
| viscosity adjustment (Sodium Chloride, | q.s. | q.s. | q.s. | q.s. | q.s. |
| preservative (DMDM Hydantoin); Water | q.s. | q.s. | q.s. | q.s. | q.s. |

*The Mid-Chain Branched surfactant according to example II

| Component | JJ | KK | LL | MM | NN |
|---|---|---|---|---|---|
| BAES* | 7.50 | 15.00 | 15.00 | 10.00 | 10.00 |
| BAS** | 2.50 | 5.00 | 5.00 | 2.50 | 2.50 |
| Cocamidopropyl Betaine | — | — | — | 2.50 | 2.50 |
| Sodium Lauroyl Sarcosinate | 0.75 | — | — | — | — |
| Ethylene Glycol Distearate | 1.50 | 1.50 | 1.50 | 1.50 | 1.50 |
| Ketoconazole | 1.00 | 1.00 | 1.00 | 1.00 | 1.00 |
| Jaguar C13S | — | 0.10 | — | 0.10 | — |
| Jaguar C17S | 0.05 | — | 0.10 | — | 0.10 |
| Fragrance | q.s. | q.s. | q.s. | q.s. | q.s. |
| Color | q.s. | q.s. | q.s. | q.s. | q.s. |
| pH adjustment (Mono/Di sodium Phosphate) | q.s. | q.s. | q.s. | q.s. | q.s. |
| Sodium Sulfate, PEG-600, Ammonium Xylene Sulfonate) | q.s. | q.s. | q.s. | q.s. | q.s. |
| preservative (DMDM Hydantoin) Water | q.s. | q.s. | q.s. | q.s. | q.s. |

*The Mid-Chain Branched surfactant according to example I.
**The Mid-Chain Branched surfactant according to example VII.

| Component | OO | PP | QQ | RR | SS | TT |
|---|---|---|---|---|---|---|
| Ammonium Laureth Sulfate | 0 | 15.00 | 0 | 15.00 | 15.00 | 0 |

-continued

| | | | | | | |
|---|---|---|---|---|---|---|
| BAS* | 5.00 | 5.00 | 5.00 | 5.00 | 5.00 | 5.00 |
| BAES** | 15.00 | 0 | 15.00 | 0 | 0 | 15.00 |
| Cocamidopropyl Betaine | 2.00 | — | — | — | — | — |
| Sodium Lauroyl Sarcosinate | — | 1.50 | 1.50 | — | — | — |
| Sodium Cocoyl Glutamate | — | — | — | — | — | 1.50 |
| Ethylene Glycol Distearate | 1.50 | 1.50 | 1.50 | 1.50 | 1.50 | 1.50 |
| Stearyl Alcohol | — | — | — | — | — | — |
| Zinc Pyrithione | 1.00 | 0.30 | 0.30 | 0.30 | 0.30 | 1.00 |
| Jaguar C13S | 0.20 | — | — | 0.10 | 0.05 | — |
| Jaguar C17S | — | 0.10 | 0.05 | — | — | 0.10 |
| Fragrance | q.s. | q.s. | q.s. | q.s. | q.s. | q.s. |
| Color | q.s. | q.s. | q.s. | q.s. | q.s. | q.s. |
| pH adjustment (Mono/Di sodium Phosphate) | q.s. | q.s. | q.s. | q.s. | q.s. | q.s. |
| viscosity adjustment (Sodium Chloride,) | q.s. | q.s. | q.s. | q.s. | q.s. | q.s. |
| preservative (DMDM Hydantoin) | q.s. | q.s. | q.s. | q.s. | q.s. | q.s. |
| Water | q.s. | q.s. | q.s. | q.s. | q.s. | q.s. |

*The Mid-Chain Branched surfactant according to example V.
**The Mid-Chain Branched surfactant according to example VI.

In preparing each of the compositions described in Examples DD to TT, about one-third of the surfactant (added as 25 wt % solution) is added to a jacketed mix tank and heated to about 74° C. with slow agitation to form a surfactant solution. Salts (sodium chloride) and pH modifiers (disodium phosphate, monosodium phosphate) are added to the tank and allowed to disperse. Ethylene glycol distearate (EGDS) is added to the mixing vessel and allowed to melt. After the EGDS is melted and dispersed (e.g., after about 5–20 minutes), preservative and additional viscosity modifier are added to the surfactant solution. The resulting mixture is passed through a heat exchanger where it is cooled to about 35° C. and collected in a finishing tank. As a result of this cooling step, the EGDS crystallizes to form a crystalline network in the product. The remainder of the surfactant and other components are added to the finishing tank with agitation to ensure a homogeneous mixture. Cationic guar polymer is dispersed in water as a 0.5–2.5% aqueous solution before addition to the final mix. Once all components have been added, viscosity and pH modifiers are added to the mixture to adjust product viscosity and pH to the extent desired.

Each exemplified composition provides excellent hair cleansing, lathering, antimicrobial agent deposition on the scalp and dandruff control.

| Component | Example XVIII | Example XIX | Example XX |
|---|---|---|---|
| BAES* | 14.00 | 14.00 | 14.00 |
| Cocamidopropyl Betaine | — | 2.50 | 2.50 |
| Cocoamphodiacetate | 2.50 | — | — |
| Cocamide MEA | 1.00 | 1.00 | 1.00 |
| Ethylene Glycol Distearate | 1.50 | 1.50 | 1.50 |
| Cetyl Alcohol | 0.42 | 0.42 | 0.42 |
| Stearyl Alcohol | 0.18 | 0.18 | 0.18 |
| Zinc Pyrithione | 1.00 | 1.00 | 1.00 |
| Jaguar C13S | 0.15 | 0.15 | — |
| Jaguar C17S | — | — | 0.15 |
| Fragrance | q.s. | q.s. | q.s. |
| Color | q.s. | q.s. | q.s. |
| pH adjustment (Mono/Di sodium Phosphate) | q.s. | q.s. | q.s. |
| viscosity adjustment (Sodium Chloride, | q.s. | q.s. | q.s. |
| preservative (DMDM Hydantoin); | q.s. | q.s. | q.s. |
| Water | | | |

*The Mid-Chain Branched surfactant according to example I.

In preparing each of the compositions described in Examples XVIII to XX, from 50% to 100% by weight of the detersive surfactants are added to a jacketed mix tank and heated to about 74° C. with slow agitation to form a surfactant solution. If used, pH modifiers (monosodium phosphate, disodium phosphate) are added to the tank and allowed to disperse. Ethylene glycol distearate (EGDS) and fatty alcohols (cetyl alcohol, stearyl alcohol) are then added to the mixing vessel and allowed to melt. After the EGDS is melted and dispersed (usually about 5–10 minutes), preservative (if used) is added and mixed into the surfactant solution. Additional viscosity modifier are added to the surfactant solution if necessary. The resulting mixture is passed through a heat exchanger where it is cooled to about 35° C. and collected in a finishing tank. As a result of this cooling step, the EGDS crystallizes to form a crystalline network in the product Any remaining surfactant and other components are added to the finishing tank with agitation to ensure a homogeneous mixture. Cationic guar polymer is dispersed in water as a 0.5–2.5% aqueous solution before addition to the final mix. Once all components have been added, viscosity and pH modifiers are added to the mixture to adjust product viscosity and pH to the extent desired.

Each exemplified composition provides excellent hair cleansing, lathering, antimicrobial agent deposition on the scalp, and dandruff control.

Example XXI

| Component | Weight % | | | | |
|---|---|---|---|---|---|
| | UU | VV | WW | XX | YY |
| BAS* | 2.0 | 2.0 | 3.0 | 2.0 | 3.0 |
| Cocamidopropyl Betaine FB | 6.0 | 6.0 | 9.0 | 6.0 | 9.0 |
| Alkyl Glyceryl Sulfonate | 10.0 | 10.0 | 6.0 | 10.0 | 6.0 |
| Mixture A | 3.0 | 6.0 | — | — | — |
| Mixture B | — | — | 3.0 | — | 6.0 |
| Mixture C | — | — | — | 3.0 | — |
| Dihydrogenated Tallowamidoethyl Hydroxyethylmonium Methosulfate (1) | 0.25 | 0.50 | — | 0.25 | — |
| Ditallowamidoethyl Hydroxypropylmonium Methosulfate (2) | — | — | 0.25 | — | 0.25 |
| Polyquaternium-16 (Luviquat 905) | — | — | — | 0.25 | — |
| Monosodium Phosphate | 0.1 | 0.1 | 0.1 | 0.1 | 0.1 |
| Disodium Phosphate | 0.2 | 0.2 | 0.2 | 0.2 | 0.2 |
| Glycol Distearate | 2.0 | 2.0 | 2.0 | 2.0 | 2.0 |
| Cocomonoethanol amide | 0.6 | 0.6 | 0.6 | 0.6 | 0.6 |
| Fragrance | 1.0 | 1.0 | 1.0 | 1.0 | 1.0 |
| Cetyl Alcohol | 0.42 | 0.42 | 0.42 | 0.42 | 0.60 |
| Stearyl Alcohol | 0.18 | 0.18 | 0.18 | 0.18 | — |
| PEG-150 Pentaerythrityl Tetrastearate | 0.1 | 0.1 | 0.1 | 0.1 | 0.1 |
| Polyquaternium 10 (JR30M) | 0.3 | — | — | 0.1 | — |
| Polyquaternium 10 (JR400) | — | 0.3 | — | — | — |
| Polyquaternium 10 (JR125) | — | — | 0.3 | — | 0.1 |
| Dimethicone | — | 0.3 | 0.3 | — | — |
| DMDM Hydantoin | 0.2 | 0.2 | 0.2 | 0.2 | 0.2 |
| Water | qs 100 | qs 100 | qs 100 | qs 100 | qs 100 |

*The Mid-Chain Branched surfactant according to example IV.
(1) Available under the tradename Varisoft 110 from Sherex Chemical Co. (Dublin, Ohio, USA)

Example XXI-continued (2) Available under the tradename Varisoft 238 from Sherex Chemical Co. (Dublin, Ohio, USA)

| Component | Weight % | | | | |
|---|---|---|---|---|---|
| | ZZ | AAA | BBB | CCC | DDD |
| BAES* | 4.0 | 5.0 | 6.0 | 3.0 | 4.0 |
| BAS** | 1.0 | 1.0 | 1.0 | 1.0 | 1.0 |
| Ammonium Laureth Sulfate | 5.5 | 4.5 | 3.5 | 3.5 | 4.5 |
| Sodium Lauroamphoacetate | 7.5 | 7.5 | 7.5 | 8.5 | 7.5 |
| Mixture A | 4.0 | 6.0 | — | — | 4.0 |
| Mixture B | — | — | 4.0 | — | — |
| Mixture C | — | — | — | 4.0 | — |
| Dihydrogenated Tallowamidoethyl Hydroxyethylmonium Methosulfate (1) | 1.0 | — | — | — | — |
| Ditallowamidoethyl Hydroxypropylmonium Methosulfate (2) | — | 0.75 | — | — | — |
| Ditallow Dimethyl Ammonium Chloride (3) | — | — | 1.0 | — | 1.0 |
| Ditallowamidoethyl Hydroxyethylmonium Methosulfate (4) | — | — | — | 0.75 | — |
| Polyquaternium-16 (Luviquat 905) | — | — | — | 0.25 | — |
| Monosodium Phosphate | 0.1 | 0.1 | 0.1 | 0.1 | 0.1 |
| Disodium Phosphate | 0.2 | 0.2 | 0.2 | 0.2 | 0.2 |
| Glycol Distearate | 2.0 | 2.0 | 2.0 | 2.0 | 2.0 |
| Cocomonoethanol amide | 0.6 | 0.6 | 0.6 | 0.6 | 0.6 |
| Fragrance | 1.0 | 0.8 | 1.0 | 1.0 | 1.0 |
| Cetyl Alcohol | 0.42 | 0.42 | 0.42 | 0.42 | 0.42 |
| Stearyl Alcohol | 0.18 | 0.18 | 0.18 | 0.18 | 0.18 |
| PEG-150 Pentaerythrityl Tetrastearate | 0.08 | 0.1 | 0.1 | 0.1 | 0.1 |
| Polyquaternium 10 (JR30M) | 0.3 | — | — | 0.1 | 0.3 |
| Polyquaternium 10 (JR400) | — | 0.3 | — | — | — |
| Polyquaternium 10 (JR125) | — | — | 0.3 | — | — |
| Dimethicone | — | 0.5 | 0.3 | — | — |
| DMDM Hydantoin | 0.2 | 0.2 | 0.2 | 0.2 | 0.2 |
| Water | qs 100 | qs 100 | qs 100 | qs 100 | qs 100 |

*The Mid-Chain Branched surfactant according to example I.
**The Mid-Chain Branched surfactant according to example IV.
(1) Available under the tradename Varisoft 110 from Sherex Chemical Co. (Dublin, Ohio, USA)
(2) Available under the tradename Varisoft 238 from Sherex Chemical Co. (Dublin, Ohio, USA)
(3) Available under the tradename Adogen 442-110P from Witco (Dublin, Ohio, USA)
(4) Available under the tradename Varisoft 222 from Sherex Chemical Co. (Dublin, Ohio, USA)

| Component | Weight % | | | | |
|---|---|---|---|---|---|
| | EEE | FFF | GGG | HHH | III |
| BAES* | 2.0 | 3.0 | 5.0 | 2.0 | 3.0 |
| BAS** | — | 1.0 | — | 1.0 | 1.0 |
| Ammonium Laureth Sulfate | 0 | 6.5 | 4.0 | 7.0 | 6.0 |
| Cocamidopropyl Betaine FB | 6.0 | — | 4.7 | — | — |
| Sodium Lauroamphoacetate | — | 7.5 | — | 7.5 | 7.5 |
| Alkyl Glyceryl Sulfonate | 10.0 | — | — | — | — |
| Mixture A | — | — | — | 4.0 | — |
| Mixture C | — | — | — | — | 4.0 |
| Mixture D | 6.0 | 4.0 | 8.0 | — | — |
| Dihydrogenated Tallowamidoethyl Hydroxyethylmonium Methosulfate (1) | 0.25 | — | — | 0.5 | — |
| Ditallow Dimethyl Ammonium Chloride (3) | — | 1.0 | — | — | — |
| Di(partially hardened soyoylethyl) Hydroxyethylmonium Methosulfate (5) | — | — | 0.75 | — | 1.0 |
| Polyquaternium-16 (Luviquat 905) | — | — | — | 0.25 | — |
| Monosodium Phosphate | 0.1 | 0.1 | 0.1 | 0.1 | 0.1 |
| Disodium Phosphate | 0.2 | 0.2 | 0.2 | 0.2 | 0.2 |
| Glycol Distearate | 2.0 | 2.0 | 2.0 | 2.0 | 2.0 |
| Cocomonoethanol amide | 0.6 | 0.6 | 0.6 | 0.6 | 0.6 |
| Fragrance | 1.0 | 1.0 | 1.0 | 1.0 | 1.0 |
| Cetyl Alcohol | 0.42 | 0.42 | 0.42 | 0.42 | 0.42 |
| Stearyl Alcohol | 0.18 | 0.13 | 0.18 | 0.18 | 0.18 |
| PEG-150 Pentaerythrityl Tetrastearate | 0.10 | 0.08 | 1.0 | 0.10 | 0.08 |
| Polyquaternium 10 (JR30M) | — | — | 0.3 | — | — |
| Polyquaternium 10 (JR400) | — | 0.3 | — | — | — |
| Polyquaternium 10 (JR125) | 0.3 | — | — | — | — |
| Guar Hydroxypropyltrimonium Chloride | — | — | — | 0.25 | 0.5 |
| Dimethicone | — | 0.5 | — | — | — |
| DMDM Hydantoin | 0.2 | 0.2 | 0.2 | 0.2 | 0.2 |
| Water | qs 100 | qs 100 | qs 100 | qs 100 | qs 100 |

*The Mid-Chain Branched surfactant according to example I.
**The Mid-Chain Branched surfactant according to example IV.
(1) Available under the tradename Varisoft 110 from Sherex Chemical Co. (Dublin, Ohio, USA)
(3) Available under the tradename Adogen 442-110P from Witco Corporation (Dublin, Ohio, USA)
(5) Available under the tradename Armocare EQ-S from Akzo-Nobel Chemicals Inc. (Chicago, Illinois, USA)

| | w/w ratio |
|---|---|
| Mixture A. | |
| Styling Polymer: t-butyl acrylate/2-ethylhexyl methacrylate (90/10 w/w) | 40 |
| Volatile Solvent: isododecane | 60 |
| Mixture B. | |
| Styling Polymer: t-butyl acrylate/2-ethylhexyl methacrylate (90/10 w/w) | 50 |
| Volatile Solvent: isododecane | 50 |
| Mixture C. | |
| Styling Polymer: t-butyl acrylate/2-ethylhexyl methacrylate/ PDMS macromer (81/9/10 w/w) | 40 |
| Volatile Solvent: isododecane | 60 |
| Mixture D. | |
| Styling Polymer: vinyl pyrrolidone/vinyl acetate (5/95 w/w) | 40 |
| Volatile Solvent: diethyl succinate | 60 |

Example XXII

The compositions of the present invention, in general, can be made by mixing together at elevated temperature, e.g., about 72° C. water and surfactants along with any solids (e.g., amphiphiles) that need to be melted, to speed mixing into the personal cleansing composition. Additional ingredients including the electrolytes can be added either to this hot premix or after cooling the premix. The nonionic or anionic polymers can be added as a water solution after cooling the premix. The ingredients are mixed thoroughly at the elevated temperature and then pumped through a high shear mill and then through a heat exchanger to cool them to ambient temperature. The silicone may be emulsified at room temperature in concentrated surfactant and then added to the cooled product. Alternately, for example, the silicone conditioning agent can be mixed with anionic surfactant and fatty alcohol, such as cetyl and stearyl alcohols, at elevated temperature, to form a premix containing dispersed silicone. The premix can then be added to and mixed with the remaining materials of the personal cleansing composition, pumped through a high shear mill, and cooled.

The personal cleansing compositions illustrated in Example XXII (JJJ to QQQ) illustrate specific embodiments of the personal cleansing compositions of the present invention, but are not intended to be limiting thereof Other modifications can be undertaken by the skilled artisan without departing from the spirit and scope of this invention. These exemplified embodiments of the personal cleansing compositions of the present invention provide cleansing of hair and/or skin and improved conditioning.

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components.

| Ingredients | JJJ | KKK | LLL | MMM | NNN |
|---|---|---|---|---|---|
| BAES* | 5.00 | — | — | — | — |
| BAS** | 5.00 | 7.50 | 7.50 | 7.50 | 7.50 |
| Sodium alkyl glycerol sulfonate | 2.50 | 2.50 | 2.50 | 2.50 | 2.50 |
| Cocoamidopropyl Betaine | — | — | — | — | — |
| Glycol Distearate | 2.00 | 1.50 | 2.00 | 2.00 | 2.00 |
| Cocomonoethanol amide | 0.60 | 0.85 | 0.85 | 0.85 | 0.85 |
| Cetyl Alcohol | 0.42 | 0.42 | 0.42 | 0.42 | 0.42 |
| Stearyl Alcohol | 0.18 | 0.18 | 0.18 | 0.18 | 0.18 |
| EDTA (ethylenediamine tetra acetic acid) | 0.10 | 0.10 | 0.10 | 0.10 | 0.10 |
| Monosodium phosphate | 0.10 | 0.10 | 0.10 | 0.10 | 0.10 |
| Disodium phosphate | 0.20 | 0.20 | 0.20 | 0.20 | 0.20 |
| Sodium Benzoate | 0.25 | 0.25 | 0.25 | 0.25 | 0.25 |
| Hydroxyethylcellulose[1] | 0.10 | 0.25 | — | — | — |
| Hydroxypropyl Guar[2] | — | — | 0.25 | — | — |
| Hydroxyethylethylcellulose[3] | — | — | — | 0.25 | — |
| Polystyrene Sulfonate | — | — | — | — | 0.25 |
| Tricetyl methylammonium chloride | 0.58 | — | — | — | — |
| Perfume | 0.60 | 0.60 | 0.60 | 0.60 | 0.60 |
| Dimethicone | 1.00 | 1.50 | 1.50 | 1.50 | 1.50 |
| Glydant | 0.20 | 0.20 | 0.20 | 0.20 | 0.20 |
| NaCl | 0.20 | 0.30 | 0.30 | 1.00 | 0.30 |
| Water and minors | -----q.s. to 100%----- | | | | |

*The Mid-Chain Branched surfactant according to example I.
**The Mid-Chain Branched surfactant according to example IV.

| Ingredients | OOO | PPP | QQQ |
|---|---|---|---|
| BAES* | — | 9.00 | 8.00 |
| BAS** | 6.00 | — | — |
| Sodium alkyl glycerol sulfonate | 1.00 | 2.50 | — |
| Cocoamidopropyl Betaine | — | 2.50 | — |
| Glycol Distearate | 1.50 | 1.50 | 2.00 |
| Cocomonoethanol amide | 0.85 | 0.85 | — |
| Cetyl Alcohol | 0.42 | 0.42 | 0.40 |
| Stearyl Alcohol | 0.18 | 0.18 | 0.18 |
| EDTA (ethylenediamine tetra acetic acid) | 0.10 | 0.10 | 0.10 |
| Monosodium phosphate | 0.10 | 0.10 | 0.10 |
| Disodium phosphate | 0.20 | 0.20 | 0.20 |
| Sodium Benzoate | 0.25 | 0.25 | 0.25 |
| Hydroxyethylcellulose[1] | 0.25 | 0.25 | 0.25 |
| Hydroxypropyl Guar[2] | — | — | — |
| Hydroxyethylethylcellulose[3] | — | — | — |
| Polystyrene Sulfonate | — | — | — |
| Tricetyl methylammonium chloride | — | — | — |
| Perfume | 0.60 | 0.60 | 0.60 |
| Dimethicone | 1.50 | 1.50 | — |
| Glydant | 0.20 | 0.20 | 0.20 |
| Sodium Lauroamphoacetate | — | — | 3.60 |
| Polyquaternium-10 | — | — | 0.20 |
| NaCl | 0.30 | 0.30 | — |
| Water and minors | -----q.s. to 100%----- | | |

*The Mid-Chain Branched surfactant according to example II.
**The Mid-Chain Branched surfactant according to example VII.
[1]Natrosol 250 HHR from Aqualon
[2]Jaguar HP 60 from Rhone-Poulenc
[3]Bermocoll E411 FQ from Akzo Nobel

What is claimed is:

1. A personal cleansing composition, comprising:
   i) from about 0.001% to 49.9% by weight of a conventional personal cleansing additive;
   ii) from about 0.1% to 49.999% by weight of a surfactant system comprising a branched surfactant mixture, said branched surfactant mixture comprising mid-chain branched and linear surfactant compounds, said linear compounds comprising 25% or less by weight of the branched surfactant mixture;

wherein the mid-chain branched surfactant compounds are of the formula:

$A^b$–B wherein:
   $A^b$ is a hydrophobic moiety having from about 10 to about 18 total carbons divided between a longest chain and at least one short chain, the longest chain being in the range of from about 9 to about 17 carbon atoms, there being one or more $C_1$–$C_3$ alkyl moieties branching from the longest chain, provided that at least one of the branching alkyl moieties is attached directly to a carbon of the longest linear carbon chain at a position within the range of position 3 carbon, counting from carbon #1 which is attached to the—B moiety, to position ω—2 carbon, wherein ω is the terminal carbon;

B is a hydrophilic moiety selected from the group consisting of $OSO_3M$, (EO/PO)mOH, (EO/PO)$mOSO_3M$ and mixtures thereof, wherein EO/PO are alkoxy moieties selected from the group consisting of ethoxy, propoxy, and mixtures thereof, wherein m is at least about 1 to about 30 and M is hydrogen or a salt forming cation;

provided that the average total number of carbon atoms in the $A^b$ moiety in the branched surfactant mixture is within the range of about 12 to 14.5; and (iii) from about 50% to about 99.899%, by weight of an aqueous liquid carrier.

2. The personal cleansing composition according to claim 1, wherein the conventional personal cleansing additive is selected from the group consisting of:
   a) conditioning agents;
   b) conventional personal care polymer;
   c) antidandruff agent;
   d) co-surfactant; and
   e) mixtures thereof.

3. The personal cleansing compositions according to claim 1 comprising alkyl chain, mid-chain branched surfactant compounds of the above formula wherein the $A^b$ moiety is a branched alkyl moiety having the formula:

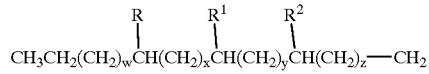

wherein the total number of carbon atoms in the branched alkyl moiety of this formula, including the R, $R^1$, and $R^2$ branching, is from 10 to 17; R, $R^1$, and $R^2$ are each independently selected from hydrogen and $C_1$–$C_3$ alkyl, preferably methyl, provided R, $R^1$, and $R^2$ are not all hydrogen and, when z is 0, at least R or $R^1$ is not hydrogen; w is an integer from 0 to 10; x is an integer from 0 to 10; y is an integer from 0 to 10; z is an integer from 0 to 10 and w+x+y+z is from 3 to 10.

4. The personal cleansing composition according to claim 1 wherein the $A^b$ moiety of the mid-chain branched surfactant compound is a branched alkyl moiety having a formula selected from the group consisting of:

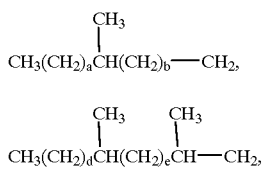

and mixtures thereof;

wherein a, b, d, and e are integers, a+b is from 6 to 13, d+e is from 4 to 11; and when a+b=6, a is an integer from 2 to 5 and b is an integer from 1 to 4;

when a+b=7, a is an integer from 2 to 6 and b is an integer from 1 to 5;

when a+b=8, a is an integer from 2 to 7 and b is an integer from 1 to 6;

when a+b=9, a is an integer from 2 to 8 and b is an integer from 1 to 7;

when a+b=10, a is an integer from 2 to 9 and b is an integer from 1 to 8;

when a+b=11, a is an integer from 2 to 10 and b is an integer from 1 to 9;

when a+b=12, a is an integer from 2 to 11 and b is an integer from 1 to 10;

when a+b=13, a is an integer from 2 to 12 and b is an integer from 1 to 11;

when d+e=4, d is an integer from 2 to 3 and e is an integer from 1 to 2;

when d+e=5, d is an integer from 2 to 4 and e is an integer from 1 to 3;

when d+e=6, d is an integer from 2 to 5 and e is an integer from 1 to 4;

when d+e=7, d is an integer from 2 to 6 and e is an integer from 1 to 5;

when d+e=8, d is an integer from 2 to 7 and e is an integer from 1 to 6;

when d+e=9, d is an integer from 2 to 8 and e is an integer from 1 to 7;

when d+e=10, d is an integer from 2 to 9 and e is an integer from 1 to 8; and when d+e=11, d is an integer from 2 to 10 and e is an integer from 1 to 9.

5. The personal cleansing composition according to claim 1, wherein the average total number of carbon atoms in the $A^b$ moiety in the branched surfactant mixture is within the range of from about 12 to about 14.

6. Antidandruff shampoo, comprising:

i) from about 0.1% to about 5% by weight of an antidandruff agent selected from the group consisting of type (a), type (b) and mixtures thereof;

ii) from about 0.1% to about 49.99% by weight of a surfactant system comprising a branched surfactant mixture, said branched surfactant mixture comprising mid-chain branched and linear surfactant compounds, said linear compounds comprising 25% or less by weight of the branched surfactant mixture;

wherein the mid-chain branched surfactant compounds are of the formula:

$A^b$-B wherein:

$A^b$ is a hydrophobic moiety having from about 10 to about 18 total carbons divided between a longest chain and at least one short chain, the longest chain being in the range of from about 9 to about 17 carbon atoms, there being one or more $C_1$–$C_3$ alkyl moieties branching from the longest chain, provided that at least one of the branching alkyl moieties is attached directly to a carbon of the longest linear carbon chain at a position within the range of position 3 carbon, counting from carbon #1 which is attached to the—B moiety, to position ω—2 carbon, wherein ω is the terminal carbon;

B is a hydrophilic moiety selected from the group consisting of $OSO_3M$, (EO/PO)mOH, (EO/PO)$mOSO_3M$ and mixtures thereof, wherein EO/PO are alkoxy moieties selected from the group consisting of ethoxy, propoxy, and mixtures thereof, wherein m is at least about 1 to about 30 and M is hydrogen or a salt forming cation;

provided that the average total number of carbon atoms in the $A^b$ moiety in the branched surfactant mixture is within the range of about 12 to 14.5; and (iii) from about 50% to about 99.89%, by weight of an aqueous liquid carrier.

7. The personal cleansing compositions according to claim 6 comprising alkyl chain, mid-chain branched surfactant compounds of the above formula wherein the $A^b$ moiety is a branched alkyl moiety having the formula:

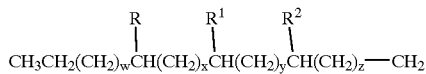

wherein the total number of carbon atoms in the branched alkyl moiety of this formula, including the R, $R^1$, and $R^2$ branching, is from 10 to 17; R, $R^1$, and $R^2$ are each independently selected from hydrogen and $C_1$–$C_3$ alkyl, preferably methyl, provided R, $R^1$, and $R^2$ are not all hydrogen and, when z is 0, at least R or $R^1$ is not hydrogen; w is an integer from 0 to 10; x is an integer from 0 to 10; y is an integer from 0 to 10; z is an integer from 0 to 10 and w+x+y+z is from 3 to 10.

8. The personal cleansing composition according to claim 6 wherein the $A^b$ moiety of the mid-chain branched surfactant compound is a branched alkyl moiety having a formula selected from the group consisting of:

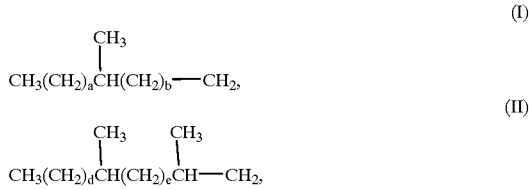

and mixtures thereof;

wherein a, b, d, and e are integers, a+b is from 6 to 13, d+e is from 4 to 11; and when a+b=6, a is an integer from 2 to 5 and b is an integer from 1 to 4;

when a+b=7, a is an integer from 2 to 6 and b is an integer from 1 to 5;

when a+b=8, a is an integer from 2 to 7 and b is an integer from 1 to 6;

when a+b=9, a is an integer from 2 to 8 and b is an integer from 1 to 7;

when a+b=10, a is an integer from 2 to 9 and b is an integer from 1 to 8;

when a+b=11, a is an integer from 2 to 10 and b is an integer from 1 to 9;

when a+b=12, a is an integer from 2 to 11 and b is an integer from 1 to 10;

when a+b=13, a is an integer from 2 to 12 and b is an integer from 1 to 11;

when d+e=4, d is an integer from 2 to 3 and e is an integer from 1 to 2;

when d+e=5, d is an integer from 2 to 4 and e is an integer from 1 to 3;

when d+e=6, d is an integer from 2 to 5 and e is an integer from 1 to 4;

when d+e=7, d is an integer from 2 to 6 and e is an integer from 1 to 5;

when d+e=8, d is an integer from 2 to 7 and e is an integer from 1 to 6;

when d+e=9, d is an integer from 2 to 8 and e is an integer from 1 to 7;

when d+e=10, d is an integer from 2 to 9 and e is an integer from 1 to 8; and when d+e=11, d is an integer from 2 to 10 and e is an integer from 1 to 9.

9. A personal conditioning composition, comprising:

i) from about 0.005% to about 20% by weight of a conditioning agent selected from the group consisting of nonvolatile hydrocarbon conditioning agents, nonvolatile silicone conditioning agents and mixtures thereof;

ii) from about 0.1% to about 49.99% by weight of a surfactant system comprising a branched surfactant mixture, said branched surfactant mixture comprising mid-chain branched and linear surfactant compounds, said linear compounds comprising 25% or less by weight of the branched surfactant mixture;

wherein the mid-chain branched surfactant compounds are of the formula:

$A^b$–B wherein:

$A^b$ is a hydrophobic moiety having from about 10 to about 18 total carbons divided between a longest chain and at least one short chain, the longest chain being in the range of from about 9 to about 17 carbon atoms, there being one or more $C_1$–$C_3$ alkyl moieties branching from the longest chain, provided that at least one of the branching alkyl moieties is attached directly to a carbon of the longest linear carbon chain at a position within the range of position 3 carbon, counting from carbon #1 which is attached to the—B moiety, to position ω—2 carbon, wherein ω is the terminal carbon; B is a hydrophilic moiety selected from the group consisting of $OSO_3M$, $(EO/PO)mOH$, $(EO/PO)mOSO_3M$ and mixtures thereof, wherein EO/PO are alkoxy moieties selected from the group consisting of ethoxy, propoxy, and mixtures thereof, wherein m is at least about 1 to about 30 and M is hydrogen or a salt forming cation;

provided that the average total number of carbon atoms in the $A^b$ moiety in the branched surfactant mixture is within he range of from about 12 to 14.5;

(iii) from about 50% to about 99.89%, by weight of an aqueous liquid carrier.

(iv) from about 0.1% to about 10%, by weight of a suspending agent.

10. The personal cleansing compositions according to claim 9 comprising alkyl chain, mid-chain branched surfactant compounds of the above formula wherein the $A^b$ moiety is a branched alkyl moiety having the formula:

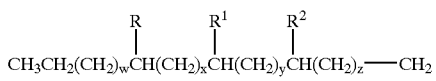

wherein the total number of carbon atoms in the branched alkyl moiety of this formula, including the R, $R^1$, and $R^2$ branching, is from 10 to 17; R, $R^1$, and $R^2$ are each independently selected from hydrogen and $C_1$–$C_3$ alkyl, preferably methyl, provided R, $R^1$, and $R^2$ are not all hydrogen and, when z is 0, at least R or $R^1$ is not hydrogen; w is an integer from 0 to 10; x is an integer from 0 to 10; y is an integer from 0 to 10; z is an integer from 0 to 10 and w+x+y+z is from 3 to 10.

11. The personal cleansing composition according to claim 9 wherein the $A^b$ moiety of the mid-chain branched surfactant compound is a branched alkyl moiety having a formula selected from the group consisting of:

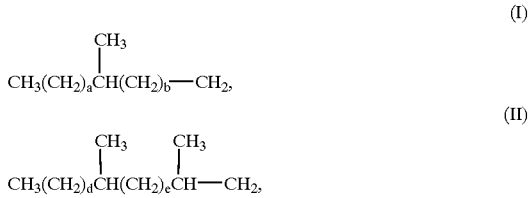

and mixtures thereof;

wherein a, b, d, and e are integers, a+b is from 6 to 13, d+e is from 4 to 11; and when a+b=6, a is an integer from 2 to 5 and b is an integer from 1 to 4;

when a+b=7, a is an integer from 2 to 6 and b is an integer from 1 to 5;

when a+b=8, a is an integer from 2 to 7 and b is an integer from 1 to 6;

when a+b=9, a is an integer from 2 to 8 and b is an integer from 1 to 7;

when a+b=10, a is an integer from 2 to 9 and b is an integer from 1 to 8;

when a+b=11, a is an integer from 2 to 10 and b is an integer from 1 to 9;

when a+b=12, a is an integer from 2 to 11 and b is an integer from 1 to 10;

when a+b=13, a is an integer from 2 to 12 and b is an integer from 1 to 11;

when d+e=4, d is an integer from 2 to 3 and e is an integer from 1 to 2;

when d+e=5, d is an integer from 2 to 4 and e is an integer from 1 to 3;

when d+e=6, d is an integer from 2 to 5 and e is an integer from 1 to 4;

when d+e=7, d is an integer from 2 to 6 and e is an integer from 1 to 5;

when d+e=8, d is an integer from 2 to 7 and e is an integer from 1 to 6;

when d+e=9, d is an integer from 2 to 8 and e is an integer from 1 to 7;

when d+e=10, d is an integer from 2 to 9 and e is an integer from 1 to 8; and when d+e=11, d is an integer from 2 to 10 and e is an integer from 1 to 9.

12. A personal cleansing composition, comprising:
i) from about 0.1% to about 10% by weight of a water insoluble hair styling polymer;
ii) from about 0.1% to about 49.99% by weight of a surfactant system comprising a branched surfactant mixture, said branched surfactant mixture comprising mid-chain branched and linear surfactant compounds, said linear compounds comprising 25% or less by weight of the branched surfactant mixture;
wherein the mid-chain branched surfactant compounds are of the formula:

$A^b$-B wherein:
$A^b$ is a hydrophobic moiety having from about 10 to about 18 total carbons divided between a longest chain and at least one short chain, the longest chain being in the range of from about 9 to about 17 carbon atoms, there being one or more $C_1$–$C_3$ alkyl moieties branching from the longest chain, provided that at least one of the branching alkyl moieties is attached directly to a carbon of the longest linear carbon chain at a position within the range of position 3 carbon, counting from carbon #1 which is attached to the—B moiety, to position ω—2 carbon, wherein ω is the terminal carbon;
B is a hydrophilic moiety selected from the group consisting of $OSO_3M$, (EO/PO)mOH, (EO/PO)m$OSO_3M$ and mixtures thereof, wherein EO/PO are alkoxy moieties selected from the group consisting of ethoxy, propoxy, and mixtures thereof, wherein m is at least about 1 to about 30 and M is hydrogen or a salt forming cation;
provided that the average total number of carbon atoms in the $A^b$ moiety in the branched sulfactant mixture is within the range of about 12 to 14.5;
(iii) from about 50% to about 99.89%, by weight of an aqueous liquid carrier and;
(iv) from about 0.1% to about 10% of a volatile water insoluble solvent.

13. A personal cleansing composition according to claim 12, wherein the composition further comprises a cationic spreading agent.

14. The personal cleansing compositions according to claim 12 comprising alkyl chain, mid-chain branched surfactant compounds of the above formula wherein the $A^b$ moiety is a branched alkyl moiety having the formula:

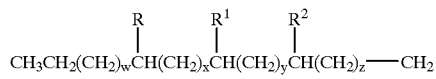

wherein the total number of carbon atoms in the branched alkyl moiety of this formula, including the R, $R^1$, and $R^2$ branching, is from 10 to 17; R, $R^1$ and $R^2$ are each independently selected from hydrogen and $C_1$–$C_3$ alkyl, preferably methyl, provided R, $R^1$, and $R^2$ are not all hydrogen and, when z is 0, at least R or $R^1$ is not hydrogen; w is an integer from 0 to 10; x is an integer from 0 to 10; y is an integer from 0 to 10; z is an integer from 0 to 10 and w+x+y+z is from 3 to 10.

15. The personal cleansing composition according to claim 12 wherein the $A^b$ moiety of the mid-chain branched surfactant compound is a branched alkyl moiety having a formula selected from the group consisting of:

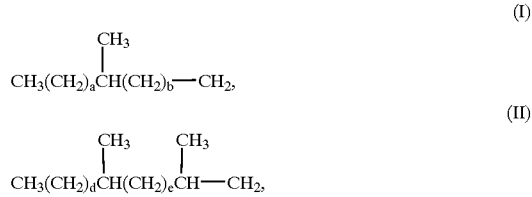

and mixtures thereof;
wherein a, b, d, and e are integers, a+b is from 6 to 13, d+e is from 4 to 11; and
when a+b=6, a is an integer from 2 to 5 and b is an integer from 1 to 4;
when a+b=7, a is an integer from 2 to 6 and b is an integer from 1 to 5;
when a+b=8, a is an integer from 2 to 7 and b is an integer from 1 to 6;
when a+b=9, a is an integer from 2 to 8 and b is an integer from 1 to 7;
when a+b=10, a is an integer from 2 to 9 and b is an integer from 1 to 8;
when a+b=11, a is an integer from 2 to 10 and b is an integer from 1 to 9;
when a+b=12, a is an integer from 2 to 11 and b is an integer from 1 to 10;
when a+b=13, a is an integer from 2 to 12 and b is an integer from 1 to 11;
when d+e=4, d is an integer from 2 to 3 and e is an integer from 1 to 2;
when d+e=5, d is an integer from 2 to 4 and e is an integer from 1 to 3;
when d+e=6, d is an integer from 2 to 5 and e is an integer from 1 to 4;
when d+e=7, d is an integer from 2 to 6 and e is an integer from 1 to 5;
when d+e=8, d is an integer from 2 to 7 and e is an integer from 1 to 6;
when d+e=9, d is an integer from 2 to 8 and e is an integer from 1 to 7;
when d+e=10, d is an integer from 2 to 9 and e is an integer from 1 to 8; and
when d+e=11, d is an integer from 2 to 10 and e is an integer from 1 to 9.

16. A personal cleansing composition, comprising:
i) from about 0.01% to about 5% by weight of a deposition polymer;
ii) from about 0.1% to about 49.99% by weight of a surfactant system comprising a branched surfactant mixture, said branched surfactant mixture comprising mid-chain branched and linear surfactant compounds, said linear compounds comprising 25% or less by weight of the branched surfactant mixture;
wherein the mid-chain branched surfactant compounds are of the formula:

$A^b$-B wherein:
A$^b$ is a hydrophobic moiety having from about 10 to about 18 total carbons divided between a longest chain and at least one short chain, the longest chain being in the range of from about 9 to about 17 carbon atoms, there being one or more $C_1$–$C_3$ alkyl moieties branching from the longest chain, provided that at least one of the branching alkyl moieties is attached directly to a carbon of the longest linear carbon chain at a position within the range of position 3 carbon, counting from carbon #1 which is attached to the—B moiety, to position ω—2 carbon, wherein ω is the terminal carbon;

B is a hydrophilic moiety selected from the group consisting of $OSO_3M$, (EO/PO)mOH, (EO/PO)$mOSO_3M$ and mixtures thereof, wherein EO/PO are alkoxy moieties selected from the group consisting of ethoxy, propoxy, and mixtures thereof, wherein m is at least about 1 to about 30 and M is hydrogen or a salt forming cation;

provided that the average total number of carbon atoms in the A$^b$ moiety in the branched surfactant mixture is within the range of about 12 to 14.5; and (iii) from about 50% to about 99.89%, by weight of an aqueous liquid carrier.

17. The personal cleansing compositions according to claim 16 comprising alkyl chain, mid-chain branched surfactant compounds of the above formula wherein the A$^b$ moiety is a branched alkyl moiety having the formula:

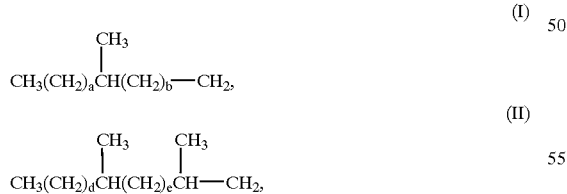

wherein the total number of carbon atoms in the branched alkyl moiety of this formula, including the R, R$^1$, and R$^2$ branching, is from 10 to 17; R, R$^1$, and R$^2$ are each independently selected from hydrogen and $C_1$–$C_3$ alkyl, preferably methyl, provided R, R$^1$, and R$^2$ are not all hydrogen and, when z is 0, at least R or R$^1$ is not hydrogen; w is an integer from 0 to 10; x is an integer from 0 to 10; y is an integer from 0 to 10; z is an integer from 0 to 10 and w+x+y+z is from 3 to 10.

18. The personal cleansing composition according to claim 16 wherein the A$^b$ moiety of the mid-chain branched surfactant compound is a branched alkyl moiety having a formula selected from the group consisting of:

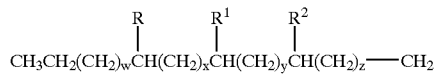

(I)

(II)

and mixtures thereof;
wherein a, b, d, and e are integers, a+b is from 6 to 13, d+e is from 4 to 11; and
when a+b=6, a is an integer from 2 to 5 and b is an integer from 1 to 4;
when a+b=7, a is an integer from 2 to 6 and b is an integer from 1 to 5;
when a+b=8, a is an integer from 2 to 7 and b is an integer from 1 to 6;
when a+b=9, a is an integer from 2 to 8 and b is an integer from 1 to 7;
when a+b=10, a is an integer from 2 to 9 and b is an integer from 1 to 8;
when a+b=11, a is an integer from 2 to 10 and b is an integer from 1 to 9;
when a+b=12, a is an integer from 2 to 11 and b is an integer from 1 to 10;
when a+b=13, a is an integer from 2 to 12 and b is an integer from 1 to 11;
when d+e=4, d is an integer from 2 to 3 and e is an integer from 1 to 2;
when d+e=5, d is an integer from 2 to 4 and e is an integer from 1 to 3;
when d+e=6, d is an integer from 2 to 5 and e is an integer from 1 to 4;
when d+e=7, d is an integer from 2 to 6 and e is an integer from 1 to 5;
when d+e=8, d is an integer from 2 to 7 and e is an integer from 1 to 6;
when d+e=9, d is an integer from 2 to 8 and e is an integer from 1 to 7;
when d+e=10, d is an integer from 2 to 9 and e is an integer from 1 to 8; and
when d+e=11, d is an integer from 2 to 10 and e is an integer from 1 to 9.

19. The personal cleansing composition according to claim 16, wherein the average total number of carbon atoms in the A$^b$ moiety in the branched surfactant mixture is within the range of from about 12 to about 14.

20. A personal cleansing composition, comprising:
i) from about 0.1% to about 10% by weight of a dispersed phase polymer;
ii) from about 0.1% to about 49.99% by weight of a surfactant system comprising a branched surfactant mixture, said branched surfactant mixture comprising mid-chain branched and linear surfactant compounds, said linear compounds comprising 25% or less by weight of the branched surfactant mixture;
wherein the mid-chain branched surfactant compounds are of the formula:

A$^b$–B wherein:
A$^b$ is a hydrophobic moiety having from about 10 to about 18 total carbons divided between a longest chain and at least one short chain, the longest chain being in the range of from about 9 to about 17 carbon atoms, there being one or more $C_1$–$C_3$ alkyl moieties branching from the longest chain, provided that at least one of the branching alkyl moieties is attached directly to a carbon of the longest linear carbon chain at a position within the range of position 3 carbon, counting from carbon #1 which is attached to the—B moiety, to position ω—2 carbon, wherein ω is the terminal carbon;

B is a hydrophilic moiety selected from the group consisting of $OSO_3M$, (EO/PO)mOH, (EO/PO)$mOSO_3M$ and mixtures thereof, wherein EO/PO are alkoxy moieties selected from the group consisting of ethoxy, propoxy, and mixtures thereof, wherein m is at least about 1 to about 30 and M is hydrogen or a salt forming cation;

provided that the average total number of carbon atoms in the A$^b$ moiety in the branched surfactant mixture is within the range of about 12 to 14.5; and (iii) from about 50% to about 99.89%, by weight of an aqueous liquid carrier.

21. The personal cleansing compositions according to claim 20 comprising alkyl chain, mid-chain branched surfactant compounds of the above formula wherein the $A^b$ moiety is a branched alkyl moiety having the formula:

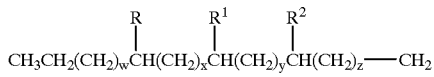

wherein the total number of carbon atoms in the branched alkyl moiety of this formula, including the R, $R^1$, and $R^2$ branching, is from 10 to 17; R, $R^1$, and $R^2$ are each independently selected from hydrogen and $C_1$–$C_3$ alkyl, preferably methyl, provided R, $R^1$, and $R^2$ are not all hydrogen and, when z is 0, at least R or $R^1$ is not hydrogen; w is an integer from 0 to 10; x is an integer from 0 to 10; y is an integer from 0 to 10; z is an integer from 0 to 10 and w+x+y+z is from 3 to 10.

22. The personal cleansing composition according to claim 20 wherein the $A^b$ moiety of the mid-chain branched surfactant compound is a branched alkyl moiety having a formula selected from the group consisting of:

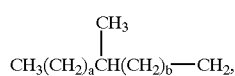 (I)

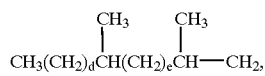 (II)

and mixtures thereof;

wherein a, b, d, and e are integers, a+b is from 6 to 13, d+e is from 4 to 11; and when a+b=6, a is an integer from 2 to 5 and b is an integer from 1 to 4;

when a+b=7, a is an integer from 2 to 6 and b is an integer from 1 to 5;

when a+b=8, a is an integer from 2 to 7 and b is an integer from 1 to 6;

when a+b=9, a is an integer from 2 to 8 and b is an integer from 1 to 7;

when a+b=10, a is an integer from 2 to 9 and b is an integer from 1 to 8;

when a+b=11, a is an integer from 2 to 10 and b is an integer from 1 to 9;

when a+b=12, a is an integer from 2 to 11 and b is an integer from 1 to 10;

when a+b=13, a is an integer from 2 to 12 and b is an integer from 1 to 11;

when d+e=4, d is an integer from 2 to 3 and e is an integer from 1 to 2;

when d+e=5, d is an integer from 2 to 4 and e is an integer from 1 to 3;

when d+e=6, d is an integer from 2 to 5 and e is an integer from 1 to 4;

when d+e=7, d is an integer from 2 to 6 and e is an integer from 1 to 5;

when d+e=8, d is an integer from 2 to 7 and e is an integer from 1 to 6;

when d+e=9, d is an integer from 2 to 8 and e is an integer from 1 to 7;

when d+e=10, d is an integer from 2 to 9 and e is an integer from 1 to 8; and when d+e=11, d is an integer from 2 to 10 and e is an integer from 1 to 9.

23. A method of treating hair, said method comprises administering a safe and effective amount of the composition according to claim 1 to hair in need of treatment.

24. A method of treating hair, said method comprises administering a safe and effective amount of the composition according to claim 6 to hair in need of treatment.

25. A method of treating hair, said method comprises administering a safe and effective amount of the composition according to claim 9 to hair in need of treatment.

26. A method of treating skin, said method comprises administering a safe and effective amount of the composition according to claim 1 to skin in need of treatment.

27. A method of cleaning hair and skin, said method comprises administering a safe and effective amount of the composition according to claim 1 to hair and skin in need of treatment.

28. A method of cleaning hair and skin, said method comprises administering a safe and effective amount of the composition according to claim 12 to hair and skin in need of treatment.

* * * * *